US009804145B2

(12) United States Patent
Kapelushnik et al.

(10) Patent No.: US 9,804,145 B2
(45) Date of Patent: Oct. 31, 2017

(54) INFRARED ANALYSIS OF BENIGN TUMORS

(71) Applicant: TODOS MEDICAL LTD., Ben Gurion Airport (IL)

(72) Inventors: Joseph Kapelushnik, Moshav Neve Ilan (IL); Shaul Mordechai, Omer (IL); Ilana Nathan, Omer (IL); Udi Zelig, Kibbutz Nir Yitzhak (IL); Rami Zigdon, Ra'anana (IL)

(73) Assignee: TODOS MEDICAL LTD., Airport City (IL)

( * ) Notice: Subject to any disclaimer, the term of this patent is extended or adjusted under 35 U.S.C. 154(b) by 0 days.

(21) Appl. No.: 14/894,128

(22) PCT Filed: Nov. 14, 2013

(86) PCT No.: PCT/IL2013/050945
§ 371 (c)(1),
(2) Date: Nov. 25, 2015

(87) PCT Pub. No.: WO2014/191980
PCT Pub. Date: Dec. 4, 2014

(65) Prior Publication Data
US 2016/0153958 A1    Jun. 2, 2016

Related U.S. Application Data

(60) Provisional application No. 61/827,933, filed on May 28, 2013.

(51) Int. Cl.
*G01N 33/48* (2006.01)
*G01N 33/483* (2006.01)
(Continued)

(52) U.S. Cl.
CPC ....... *G01N 33/4833* (2013.01); *G01N 21/359* (2013.01); *G01N 21/3563* (2013.01);
(Continued)

(58) Field of Classification Search
CPC .................................................. G01N 33/4833
See application file for complete search history.

(56) References Cited

U.S. PATENT DOCUMENTS

| 4,832,483 A | 5/1989 | Verma |
| 4,912,050 A | 3/1990 | Fossel |

(Continued)

FOREIGN PATENT DOCUMENTS

| WO | 92/14134 | 8/1992 |
| WO | 96/00892 | 1/1996 |

(Continued)

OTHER PUBLICATIONS

U.S. Appl. No. 61/350,073, filed Jun. 1, 2010.
(Continued)

*Primary Examiner* — David Porta
*Assistant Examiner* — Hugh H Maupin
(74) *Attorney, Agent, or Firm* — Sughrue Mion, PLLC

(57) ABSTRACT

A method is provided comprising, obtaining an infrared (IR) spectrum of a Peripheral Blood Mononuclear Cells (PBMC) sample of a subject by analyzing the sample by infrared spectroscopy; analyzing the infrared spectrum using a processor (22), and based on the analyzing using the processor, using an output device (24), generating an output indicative of the presence of a benign tumor of the subject. Other applications are also described.

16 Claims, 69 Drawing Sheets

(51) Int. Cl.
  *G01N 21/3577* (2014.01)
  *G01N 21/3563* (2014.01)
  *G01N 21/359* (2014.01)
  *G01N 21/35* (2014.01)

(52) U.S. Cl.
  CPC . *G01N 21/3577* (2013.01); *G01N 2021/3595* (2013.01); *G01N 2201/12* (2013.01)

(56) References Cited

U.S. PATENT DOCUMENTS

| | | | |
|---|---|---|---|
| 5,197,470 | A | 3/1993 | Helfer et al. |
| 5,261,410 | A * | 11/1993 | Alfano ............... A61B 5/0075 250/339.12 |
| 5,697,373 | A | 12/1997 | Richards-Kortum et al. |
| 5,733,739 | A | 3/1998 | Zakim et al. |
| 5,734,587 | A | 3/1998 | Backhaus et al. |
| 5,945,674 | A | 8/1999 | Dukor |
| 5,945,675 | A | 8/1999 | Malins |
| 6,251,616 | B1 | 6/2001 | Barbera-Guillem |
| 6,274,871 | B1 | 8/2001 | Dukor et al. |
| 6,642,012 | B1 | 11/2003 | Ashdown |
| 6,841,388 | B2 | 1/2005 | Dukor et al. |
| 7,524,681 | B2 | 4/2009 | Wolf et al. |
| 7,611,839 | B2 | 11/2009 | Twine |
| 8,173,433 | B2 | 5/2012 | Folkman et al. |
| 9,606,057 | B2 | 3/2017 | Kapelushnik et al. |
| 2001/0000150 | A1 | 4/2001 | Malins |
| 2002/0027649 | A1 | 3/2002 | Chudner |
| 2002/0164810 | A1 | 11/2002 | Dukor et al. |
| 2004/0073011 | A1 | 4/2004 | Hagay et al. |
| 2004/0110221 | A1 | 6/2004 | Twine et al. |
| 2004/0186383 | A1 | 9/2004 | Rava et al. |
| 2005/0017179 | A1 | 1/2005 | Mordechai et al. |
| 2006/0194211 | A1 | 8/2006 | Burczynski |
| 2007/0003921 | A1 | 1/2007 | Andrus |
| 2007/0282190 | A1 * | 12/2007 | Dekel ............... A61B 1/041 600/407 |
| 2009/0004682 | A1 | 1/2009 | Kitamura et al. |
| 2009/0175819 | A1 | 7/2009 | Priest et al. |
| 2010/0021039 | A1 | 1/2010 | Ortyn et al. |
| 2010/0185064 | A1 | 7/2010 | Bandic et al. |
| 2010/0210023 | A1 | 8/2010 | Wong et al. |
| 2010/0273191 | A1 | 10/2010 | Arber |
| 2011/0028808 | A1 | 2/2011 | Kuratsune et al. |
| 2011/0182881 | A1 | 7/2011 | Chin et al. |
| 2013/0137134 | A1 * | 5/2013 | Mordechai ............ G01N 21/35 435/34 |
| 2013/0143258 | A1 | 6/2013 | Kapelushnik et al. |
| 2014/0087397 | A1 | 3/2014 | Romick-Rosendale et al. |
| 2014/0166884 | A1 | 6/2014 | Kapelushnik et al. |

FOREIGN PATENT DOCUMENTS

| | | |
|---|---|---|
| WO | 2009/074988 | 6/2009 |
| WO | 2011/121588 | 10/2011 |
| WO | 2011/151825 | 12/2011 |
| WO | 2012/153326 | 11/2012 |

OTHER PUBLICATIONS

An International Search Report and a Written Opinion both dated Nov. 29, 2011, which issued during the prosecution of Applicant's PCT/IL2011/000426.
An International Preliminary Report on Patentability dated Dec. 4, 2012, which issued during the prosecution of Applicant's PCT/IL2011/000426.
An International Search Report and a Written Opinion both dated Aug. 3, 2011, which issued during the prosecution of Applicant's PCT/IL2011/000282.
An International Search Report and a Written Opinion both dated Aug. 31, 2012, which issued during the prosecution of Applicant's PCT/IL2012/000187.
An International Preliminary Report on Patentability dated Nov. 12, 2013, which issued during the prosecution of Applicant's PCT/IL2012/000187.
Agatha G., et al., Fatty acid composition of lymphocyte membrane phospholipids in children with acute leukemia. Cancer Lett. Nov. 28, 2001;173(2):139-44.
Arakawa H., et al., Silver (I) complexes with DNA and RNA studied by Fourier transform infrared spectroscopy and capillary electrophoresis. Biophys J. Sep. 2001;81(3):1580-7.
Argov S., et al., Diagnostic potential of Fourier-transfona infrared microspectroscopy and advanced computational methods in colon cancer patients. J Biomed Opt. Apr. 2002;7(2):248-54.
Argov S, Sahu RK, Bernshtain E, Salman A, Shohat G, Zelig U, Mordechai S. Inflammatory bowel diseases as an intermediate stage between normal and cancer: a FTIR-microspectroscopy approach.
Backhaus J., et al., Diagnosis of breast cancer with infrared spectroscopy from serum sample. Vibrational Spectroscopy 52(2010) 173-177.
Beyer M., and Schulze J. L., Regulatory T cells in cancer. Blood. Aug. 1, 2006;108(3):804-11.
Bogomolny E., et al., Early spectral changes of cellular malignant transformation using Fourier transformation infrared microspectroscopy. 2007. J Biomed Opt.12:024003.
Boydston-White ST., et al., 1999, Infrared spectroscopy of human tissue V infrared spectroscopic studies of myeloid leukemia (ML-1) cells at different phases of cell cycle. Biospectroscopy 5:219-227.
Coates RJ, et al., Diagnostic markers for ovarian cancer screening: not ready for routine clinical use. Clin Cancer Res. Nov. 15, 2008;14(22):7575-6.
Curiel TJ., et al., Specific recruitment of regulatory T cells in ovarian carcinoma fosters immune privilege and predicts reduced survival. Nat Med. Sep. 2004;10(9):942-9.
Diem M., et al., A decade of Vibrational micro-spectroscopy of human cells and tissue (1994-2004). Analyst 129,88-885 (2004).
Duffy MJ. Role of tumor markers in patients with solid cancers: A critical review. Eur J Intern Med. May 2007;18(3):175-184.
Fabian H., et al., Diagnosing benign and malignant lesions in breast tissue sections by using IR-microspectroscopy. Biochim Biophys Acta. Jul. 2006;1758(7):874-82.
Gazi E., et al., Biomolecular profiling of metastatic prostate cancer cells in bone marrow tissue using FTIR microspectroscopy: a pilot study. Anal Bioanal Chem. Mar. 2007;387(5):1621-31.
Gottfried EL., Lipids of human leukocytes: relation to celltype. J Lipid Res. Jul. 1967;8(4):321-7.
Graser A., et al., Comparison of CT colonography, colonoscopy, sigmoidoscopy and faecal occult blood tests for the detection of advanced adenoma in an average risk population. Gut. Feb. 2009;58(2):241-8.
Handy B. The Clinical Utility of Tumor Markers. LabMedicine. Feb. 2009; 40, 99-103.
Hammody Z., et al., Distinction of malignant melanoma and epidermis using IR micro-spectroscopy and statistical methods. Analyst. Mar. 2008;133(3):372-8.
Hildebrand J., et al., Neutral glycolipids in leukemic and nonleukemic leukocytes. J Lipid Res. May 1971;12(3):361-6.
Inbar M., et al., Cholesterol as a bioregulator in the development and inhibition of leukemia. Proc Natl Acad Sci U S A. Oct. 1974;71(10):4229-31.
Inbar M., et al., Fluidity difference of membrane lipids in human normal and leukemic lymphocytes as controlled by serum components. Cancer Res. Sep. 1977;37(9):3037-41.
Kanika Singh., et al., Spectroscopic techniques as a diagnostic tool for early detection of osteoporosis. Journal of Mechanical Science and Technology vol. 24, No. 8, 1661-1668.
Khanmohammadi M., et al., Diagnosis of basal cell carcinoma by infrared spectroscopy of whole blood samples applying soft independent modeling class analogy. J Cancer Res Clin Oncol. Dec. 2007;133(12):1001-10. Epub Aug. 2, 2007.
Kiviniemi MT., et al., Decision making about cancer screening: an assessment of the state of the science and a suggested research agenda from the ASPO Behavioral Oncology and Cancer Communication Special Interest Group. Cancer Epidemiol Biomarkers Prev. Nov. 2009;18(11):3133-7.

(56) References Cited

OTHER PUBLICATIONS

Krafft C., et al., Identification of primary tumors of brain metastases by SIMCA classification of IR spectroscopic images. Biochim Biophys Acta. Jul. 2006;1758(7):883-91.
Kriat M., et al., Analysis of plasma lipids by NMR spectroscopy: application to modifications induced by malignant tumors. J Lipid Res. Jun. 1993;34(6):1009-19.
Leong PP., et al., Phenotyping of lymphocytes expressing regulatory and effector markers in infiltrating ductal carcinoma of the breast. Immunol Lett. Feb. 15, 2006;102(2):229-36.
Liu KZ., et al., Bimolecular characterization of leucocytes by infrared spectroscopy. Br J Haematol. Mar. 2007;136 (5):713-22.
Liu KZ., et al., Tumor regulatory T cells potently abrogate antitumor immunity. J Immunol. May 15, 2009;182(10):6160-7.
Liyanage UK., et al., Prevalence of regulatory T cells is increased in peripheral blood and tumor microenvironment of patients with pancreas or breast adenocarcinoma. J Immunol. Sep. 1, 2002;169(5):2756-61.
Lyman DJ., et al., Fourier transform infrared attenuated total reflection analysis of human hair: comparison of hair from breast cancer patients with hair from healthy subjects. Appl Spectrosc. Jan. 2005;59(1):26-32.
Mitchell PS., et al., Circulating microRNAs as stable blood-based markers for cancer detection. PNAS Jul. 29, 2008 vol. 105 No. 30 10513-10518.
Cazzaniga G, Biondi A. Molecular monitoring of childhood acute lymphoblastic leukemia using antigen receptor gene rearrangements and quantitative polymerase chain reaction technology. Haematologica. Mar. 2005;90(3):382-90.
Mordechai S., et al., Possible common biomarkers from FTIR microspectroscopy of cervical cancer and melanoma. J Microsc. Jul. 2004;215(Pt 1):86-91.
Naumann D. FT-infrared and FT-Raman spectroscopy in bio-medical research, Appl. Spectrosc. Rev. 36, 239-298 (2001).
Pavlou MP, Diamandis EP. The cancer cell secretome: a good source for discovering biomarkers? J Proteomics. Sep. 10, 2010;73(10):1896-906.
Petibois C., et al., Plasma protein contents determined by Fourier-transform infrared spectrometry. Clin Chem. Apr. 2001;47(4):730-8.
Petibois C., et al., Analytical performances of FT-IR spectrometry and imaging for concentration measurements within biological fluids, cells, and tissues. Analyst. May 2006;131(5):640-7.
Campana D. Molecular determinants of treatment response in acute lymphoblastic leukemia. Hematology Am Soc Hematol Educ Program. 2008:366-73.
Petter CH., et al., Development and application of Fourier-transform infrared chemical imaging of tumour in human tissue. Curr Med Chem. 2009;16(3):318-26.
Ransohoff DF. Rules of evidence for cancer molecular-marker discovery and validation. Nat Rev Cancer. Apr. 2004;4(4):309-14.
Sahu RK., et al., Detection of abnormal proliferation in histologically 'normal' colonic biopsies using FTIR-microspectroscopy. Scand J Gastroenterol. Jun. 2004;39(6):557-66.
Sahu RK., et al., Can Fourier transform infrared spectroscopy at higher wavenumbers (mid IR) shed light on biomarkers for carcinogenesis in tissues? J Biomed Opt. Sep.-Oct. 2005;10(5):054017.
Sahu RK., et al., Continuous monitoring of WBC (biochemistry) in an adult leukemia patient using advanced FTIR-spectroscopy. Leuk Res. Jun. 2006;30(6):687-93.
Sasada T., et al., CD4+CD25+ regulatory T cells in patients with gastrointestinal malignancies: possible involvement of regulatory T cells in disease progression. Cancer. Sep. 1, 2003;98(5):1089-99.
Saslow D., et al., American Cancer Society Breast Cancer Advisory Group. American Cancer Society guidelines for breast screening with MRI as an adjunct to mammography. CA Cancer J Clin. Mar.-Apr. 2007;57(2):75-89. Erratum in: CA Cancer J Clin. May-Jun. 2007;57(3):185.
Shaw RA., et al., Multianalyte serum analysis using mid-infrared spectroscopy. Ann Clin Biochem. Sep. 1998;35 ( Pt 5):624-32.
Shimokawara I., et al., Identification of lymphocyte subpopulations in human breast cancer tissue and its significance: an immunoperoxidase study with anti-human T- and B-cell sera. Cancer. Apr. 1, 1982;49(7):1456-64.
Smith RA., et al., Cancer screening in the United States, 2010: a review of current American Cancer Society guidelines and issues in cancer screening. CA Cancer J Clin. Mar.-Apr. 2010;60(2):99-119.
Spiegel, R J., et al., 1982. Plasma lipids alterations in leukemia and lymphoma. Am. J. Med. 72: 775-781.
Tokuno K., et al., Increased prevalence of regulatory T-cells in the peripheral blood of patients with gastrointestinal cancer. Anticancer Res. May 2009;29(5):1527-32.
Toyran N., et al., Selenium alters the lipid content and protein profile of rat heart: an FTIR microspectroscopy study. Arch. Biochem.Biophys. 2007 458:184-193.
Whitehead RH., et al., T and B lymphocytes in breast cancer stage relationship and abrogation of T-lymphocyte depression by enzyme treatment in vitro. Lancet. Feb. 14, 1976;1(7955):330-3.
Whitford P., et al., Flow cytometric analysis of tumour infiltrating lymphocytes in breast cancer. Br J Cancer. Dec. 1990;62(6):971-5.
Wieczorek G., et al., Quantitative DNA methylation analysis of FOXP3 as a new method for counting regulatory T cells in peripheral blood and solid tissue. Cancer Res. Jan. 15, 2009;69(2):599-608.
Wolf AM., et al., Increase of regulatory T cells in the peripheral blood of cancer patients. Clin Cancer Res. Feb. 2003;9(2):606-12.
Zelig U., et al., Diagnosis of cell death by means of infrared spectroscopy. Biophys J Oct. 7, 2009;79:2107-14.
Zhang SL, et al., Vibrational Spectra and Experimental Assignments of Thymine and Nine of its Isotopomers J. Phys. Chem. A. 102 (1998), p. 461.
An Office Action dated Aug. 19, 2013, which issued during the prosecution of U.S. Appl. No. 13/638,367.
Ramesh et al. Novel Methodology for the Follow-Up of Acute Lympblastic Leukemia Using FTIR Microspectroscopy; Journal of Biochemical and Biophysical Methods, vol. 51 (2002) pp. 251-261.
Mohlenhoff et al.Mie-Type Scattering and Non-Beer-Lambert absorption behavior of human cells in infrared microspectroscopy.
Bogomolny et al. "Monitoring of viral cancer progression using FTIR microscopy: A comparative study of intact cells and tissues."
Visintin, Irene, et al.: "Diagnostic Markers for Early Detection of Ovarian Cancer", Clin Cancer Res 2008; 14:1065-1072, DOE10. 1158/1078-0432.CCR-07-1569, Published online Feb. 7, 2008.
Hengartner, M. O. The biochemistry of apoptosis. Nature. 2000, 407: 770-776.
Andrus PG. Cancer monitoring by FTIR spectroscopy. Technol Cancer Res Treat. Apr. 2006;5(2):157-67.
Lavie Y, et al., Changes in membrane microdomains and caveolae constituents in multidrug-resistant cancer cells. Lipids. 1999;34 Suppl:S57-63.
Vrooman LM, Silverman LB. Childhood acute lymphoblastic leukemia: update on prognostic factors. Curr Opin Pediatr. Feb. 2009;21(1):1-8.
Krishna CM., et al., Combined Fourier transform infrared and Raman spectroscopic approach for identification of multidrug resistance phenotype in cancer cell lines. Biopolymers. Aug. 5, 2006;82(5):462-70.
Basso G, et al., Risk of relapse of childhood acute lymphoblastic leukemia is predicted by flow cytometric measurement of residual disease on day 15 bone marrow. J Clin Oncol. Nov. 1, 2009;27(31):5168-74.
Pui CH, Evans WE. Treatment of acute lymphoblastic leukemia. N Engl J Med 2006; 354: 166-78.
Tucci F, Aricò M. Treatment of pediatric acute lymphoblastic leukemia. Haematologica. Aug. 2008;93(8):1124-8.
Castillo L. A Randomized Trial of the I-BFM-SG for the Management of Childhood non-B Acute Lymphoblastic Leukemia. ALL IC-BFM 2002.
U.S. Appl. No. 61/318,395, filed Mar. 29, 2010.

(56) References Cited

OTHER PUBLICATIONS

Smith M, et al., Uniform approach to risk classification and treatment assignment for children with acutelymphoblastic leukemia. J Clin Oncol. Jan. 1996;14(1):18-24. PubMed PMID: 8558195.
Mehrotra et al., Analysis of ovarian tumor pathology by Fourier Transform Infrared Spectroscopy, Journal of Ovarian Research, 2010, vol. 3, No. 27, p. 1-6.
Devi et al., FTIR Spectroscopic Analysis of Normal and Cancerous Human Breast Tissues between 450 Cm-1 and 1100 Cm-1 using Trend Analysis, International Journal of ChemTech Research, Sep. 2010, vol. 2, No. 3, pp. 1426 to 1433.
Schultz et al., Study of Chronic Lymphocytic Leukemia Cells by FT-IR Spectroscopy and Cluster Analysis, Pergamon, Leukemia Research, 1996, vol. 20, No. 8, pp. 649 to 655.
Big Medicine Encyclopedia. Ed. Petrovskiy, vol. 12, 1980, 13 pages total.
An English translation of RU 2 352 256.
An English translation of a communication, issued by the Russian Patent Office in corresponding Russian Application No. 2012157998.
International Search Report with Written Opinion dated Apr. 23, 2014, issued by the International Searching Authority in corresponding International Application No. PCT/IL13/050945.
European Search Report dated Oct. 10, 2014, which issued during the prosecution of Applicant's European App No. 12782256.7.
Khanmohammadi et al., Chemometrics assisted investigation of variations in infrared spectra of blood samples obtained from women with breast cancer: a new approach for cancer diagnosis, Eur J Cancer Care, 2010, vol. 19, pp. 352 to 359.
Krishna et al, Characterisation of uterine sarcoma cell lines exhibiting MDR phenotype by vibrational spectroscopy, Biochimica et Biophysica Acta (BBA), Elsevier, 2005, General Subjects vol. 1726, Issue 2, pp. 160 to 167.
Khanmohammadi et al., Cancer Diagnosis by Discrimination between Normal and Malignant Human Blood Samples Using Attenuated Total Reflectance-Fourier Transform Infrared Spectroscopy, Informa Healthcare, Cancer Investigation, 2007, vol. 25, pp. 397 to 404.
Bosschaart et al., "A literature review and novel theoretical approach on the optical properties of whole blood", Lasers Med Sci, 2014, vol. 29, pp. 453-479.
Meinke et al., "Optical propertied of platelets and blood plasma and their influence on the optical behavior of whole blood in the visible to near infrared wavelength range", J Biomed Opt, Jan.-Feb. 2007, vol. 12, No. 1, pp. 014024 (Abstract).
An Office Action dated Jun. 8, 2015, which issued during the prosecution of U.S. Appl. No. 14/116,506.
Wood et al. Fourier Transform Infrared Spectroscopy As a Method for Monitoring the Molecular Dynamics of Lymphocyte Activation; Applied Spectroscopy, vol. 54, No. 3 (2000) pp. 353-359.
Applicant response dated Jan. 20, 2015, to Office Action dated Sep. 18, 2014, which issued during the prosecution of U.S. Appl. No. 13/701,262.
Interview Summary Report dated Jan. 26, 2015, which issued during the prosecution of U.S. Appl. No. 13/701,262.
Interview Summary Report dated Jan. 22, 2014, which issued during the prosecution of U.S. Appl. No. 13/701,262.
Interview Summary Report dated Sep. 4, 2015, which issued during the prosecution of U.S. Appl. No. 13/701,262.
Applicant response dated Sep. 8, 2015, to Office Action dated Mar. 6, 2015, which issued during the prosecution of U.S. Appl. No. 13/701,262.
An Office Action dated Mar. 6, 2015, which issued during the prosecution of U.S. Appl. No. 13/701,262.
An Office Action dated Nov. 2, 2015, which issued during the prosecution of U.S. Appl. No. 13/701,262.
An Office Action dated Oct. 16, 2013, which issued during the prosecution of U.S. Appl. No. 13/701,262.
An Office Action dated Sep. 18, 2014, which issued during the prosecution of U.S. Appl. No. 13/701,262.
An Office Action dated Feb. 24, 2014, which issued during the prosecution of U.S. Appl. No. 13/701,262.
U.S. Appl. No. 61/484,753, filed May 11, 2011.
Applicant response dated Aug. 25, 2014, to Office Action dated Feb. 24, 2014, which issued during the prosecution of U.S. Appl. No. 13/701,262.
Applicant response dated Jan. 16, 2014, to Office Action dated Oct. 16, 2013, which issued during the prosecution of U.S. Appl. No. 13/701,262.
U.S. Appl. No. 61/827,933, filed May 28, 2013.
Ela Ostrovsky et al: "Detection of Cancer Using Advanced Computerized Analysis of Infrared Spectra of Peripheral Blood", IEEE Transactions on Biomedical Engineering, IEEE Service Center, Piscataway, NJ, USA, vol. 60, No. 2, Feb. 1, 2013.
Notice of Allowance dated Feb. 1, 2017, which issued during the prosecution of U.S. Appl. No. 13/701,262.
Udi Zelig et al: "Pre-screening and follow-up of childhood acute leukemia using biochemical infrared analysis of peripheral blood mononuclear cells", Biochimica et Biophysica Acta (BBA)—General Subjects, Elsevier, Amsterdam, NL, vol. 1810, No. 9, Jun. 15, 2011.
Sylwia Olsztynska-Janus et al: "Spectroscopic techniques in the study of human tissues and their components. Part I: IR spectroscopy", Acta of Bioengineering and Biomechanics Review Article, vol. 14, Jan. 1, 2012.
Notice of Allowance dated Feb. 8, 2017, which issued during the prosecution of U.S. Appl. No. 13/701,262.
An Office Action dated May 12, 2016, which issued during the prosecution of U.S. Appl. No. 13/701,262.
An Office Action dated Feb. 12, 2016, which issued during the prosecution of U.S. Appl. No. 14/116,506.
An Office Action dated Sep. 13, 2016, which issued during the prosecution of U.S. Appl. No. 14/116,506.
European Search Report dated Jan. 26, 2017, which issued during the prosecution of Applicant's European App No. 13885931.9.
Interview Summary Report dated Mar. 7, 2017, which issued during the prosecution of U.S. Appl. No. 14/116,506.
Bitar, Renata Andrade et al.: "Biochemical analysis of human breat tissues using FT-Raman spectroscopy," Laboratory of Biomedical Vibrational Spectroscopy, 2006.
Gao, Tiyu et al.: "Human breast carcionmal tissues display distinctive FTIR spectra: Implication for the histological characterization of carcinomas", Department of Chemistry, Peking University, Beijing 100871, China, Feb. 17, 1999.
Applicant response dated Nov. 14, 2016, to Office Action dated May 12, 2016, which issued during the prosecution of U.S. Appl. No. 13/701,262.

\* cited by examiner

PBMC: HEALTHY (14) VS. BENIGN (15)
SENSITIVITY: 73%
SPECIFICITY: 79%

PLASMA: HEALTHY (13) VS. BENIGN (15)
SENSITIVITY: 53%
SPECIFICITY: 92%

BREAST - LEAVE ONE OUT CROSS VALIDATION

I. HEALTHY VS. BENIGN

| | | |
|---|---|---|
| F1- PLASMA | 768.0119 | 761.2623 |
| F2- PLASMA | 1054.871 | 1013.409 |
| F1- PBMC | 1026.426 | 961.8228 |
| F2- PBMC | 1171.061 | 1116.582 |

COMBINED PBMC AND PLASMA: HEALTHY (12) VS. BENIGN (15)
SENSFIITIVITY: 93%
SPECIFICITY: 100%

PBMC: BENIGN (15) VS. CANCER (29)
SENSITIVITY: 72%  OR
SPECIFICITY: 80%

SENSITIVITY: 90%
SPECIFICITY: 67%

PLASMA: BENIGN (15) VS. CANCER (29)
SENSITIVITY: 60%
SPECIFICITY: 100%

OR

SENSITIVITY: 92%
SPECIFICITY: 73%

ROC CURVE
AUC: 0.8344

II. BENIGN VS. CANCER

F1 - PLASMA        1652.696        1659.446

F2 - PLASMA        761.2623        768.0119

F1 - PBMC          1547.595        1540.845

F2 - PBMC          1010.034        1023.534

COMBAINED PBMC AND PLASMA:   BENIGN (15) VS. CANCER (25)
SENSITIVITY: 76%                          OR
SPECIFICITY: 87%

SENSITIVITY: 96%
SPECIFICITY: 73%

ROC CURVE
AUC: 0.8592

BREAST CANCER
12 HEALTHY; 15 BENIGN; 25 CANCER;

LEAVE ONE OUT CROSS VALIDATION
COMBAIND PLASNA & PBMC FEATURES
CLASSIFIER: QDA

I. B1 HEALTHY + BENIGN (27) VS. CANCER (25)
TOTAL 3 FEATURES

HIGH SENSITIVITY

|  | #HLT; #CNC | SENSITIVITY[%] | SPECIFICITY[%] |
|---|---|---|---|
| TRAINING | # 27; # 25 | 92 | 77.8 |
| VALIDATION (LOOCV) | #27; #25 | 92 | 74.1 |

| | | MAMMOGRAPHY/US/PATHOLOGY | | | |
|---|---|---|---|---|---|
| | | HEALTHY | BEN | HGD | CANCER |
| TBIA | HEALTHY | 10 | 12 | 0 | 5 |
| | CANSER | 4 | 3 | 1 | 23 |
| | SENSITIVITY/SPECIFICITY | 71% | 80% | 100% | 82% |

PBMC: BENIGN (13) VS. CANCER (32)
SENSITIVITY: 94%
SPECIFICITY: 54%

PLASMA: BENIGN (12) VS. CANCER (28)
SENSITIVITY: 93%
SPECIFICITY: 58%

COLON - LEAVE ONE OUT CROSS VALIDATION
I. BENIGN VS. CANCER

| | | |
|---|---|---|
| F1 - PLASMA | 1114.172 | 1174.436 |
| F2 - PLASMA | 1034.14 | 1052.461 |
| F1 - PBMC | 713.5327 | 760.7802 |
| F2 - PBMC | 1484.919 | 1490.223 |

COMBINED PBMC AND PLASMA: BENIGN (11) VS. CANCER (27)
SENSITIVITY: 96%
SPECIFICITY: 82%

PLASMA: HEALTHY (14) VS. BENIGN (12)
SENSITIVITY: 83%          OR          SENSITIVITY: 67%
SPECIFICITY: 79%                       SPECIFICITY: 86%

II. HEALTHY VS. BENIGN

F1 - PLASMA     1379.336     1400.067

F1 - PBMC       706.7831     811.8845

F2 - PBMC       870.2206     879.863

COMBINED PBMC & PLASMA:   HEALTHY (14) VS. BENIGN (11)
SENSITIVITY: 91%          OR
SPECIFICITY: 79%

SENSITIVITY: 73%
SPECIFICITY: 93%

COLON CANCER
14 HEALTHY + 11 BENIGN VS. 27 CANCER;

LEAVE ONE OUT CROSS VALIDATION
PLASMA FEATURES ONLY
CLASSIFIER: QDA

C1- HEALTHY (14) + BENIGN (11) VS. CANCER (27)

|  | SENSITIVITY[%] | SPECIFICITY[%] |
|---|---|---|
| VALIDATION (LOOCV) | 92.86 | 80.77 |

COLON CANCER
14 HEALTHY VS. 11 BENIGN + 27 CANCER;

LEAVE ONE OUT CROSS VALIDATION
COMBINED PLASNA & PBMC FEATURES
CLASSIFIER: QDA

I. C1- HEALTHY (14) VS. BENIGN + CANCER (38)
    TOTAL 2 FEATURES

FIG. 7H (CONT.)

HIGH SPECIFICITY

|  | #HLT; #CNC | SENSITIVITY[%] | SPECIFICITY[%] |
|---|---|---|---|
| TRAINING | # 14; # 38 | 73.7 | 92.9 |
| VALIDATION (LOOCV) | #14; #38 | 73.7 | 92.9 |

HIGH SENSITIVITY

|  | #HLT; #CNC | SENSITIVITY[%] | SPECIFICITY[%] |
|---|---|---|---|
| TRAINING | # 14; # 38 | 86.8 | 64.3 |
| VALIDATION (LOOCV) | #14; #38 | 89.5 | 71.4 |

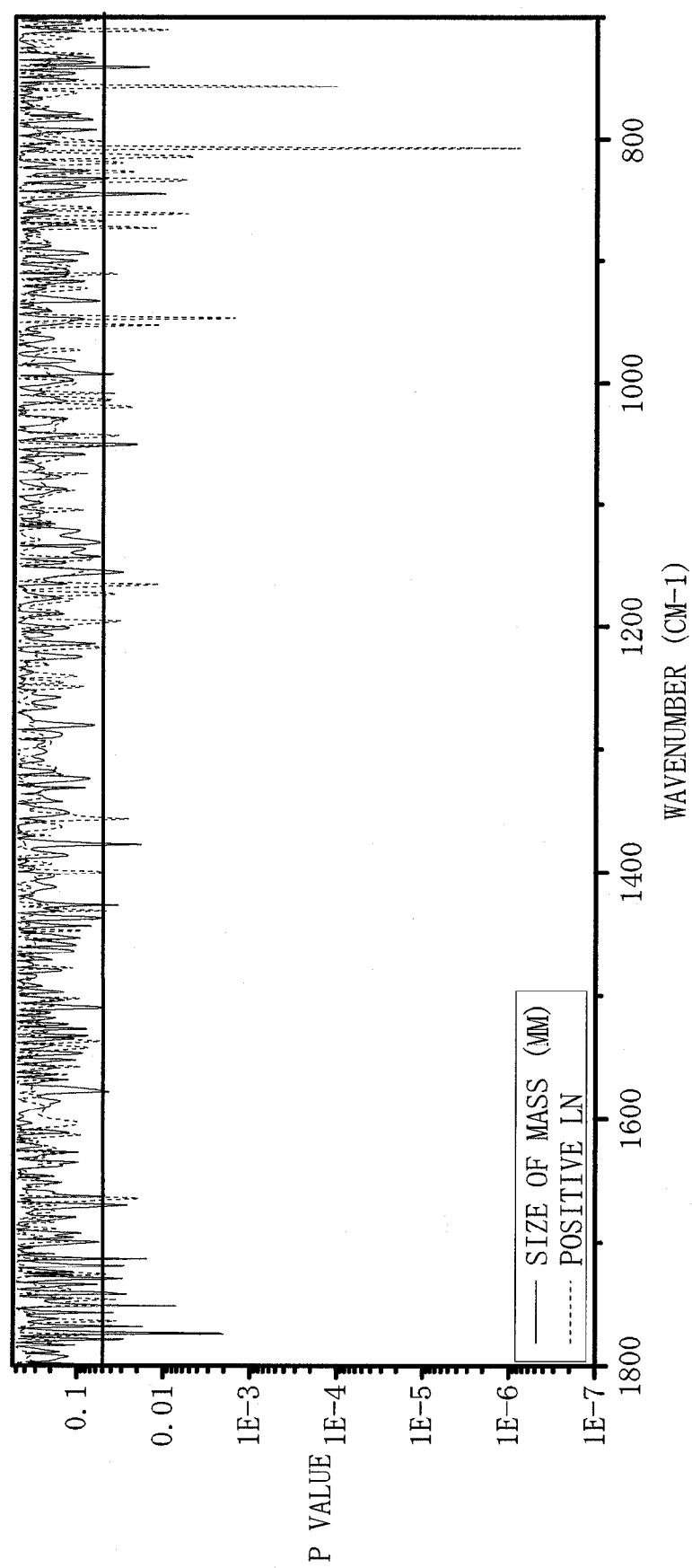

PBMC: HEALTHY (53) VS. CANCER (128)
SENSITIVITY: 43.5%
SPECIFICITY: 96.5%

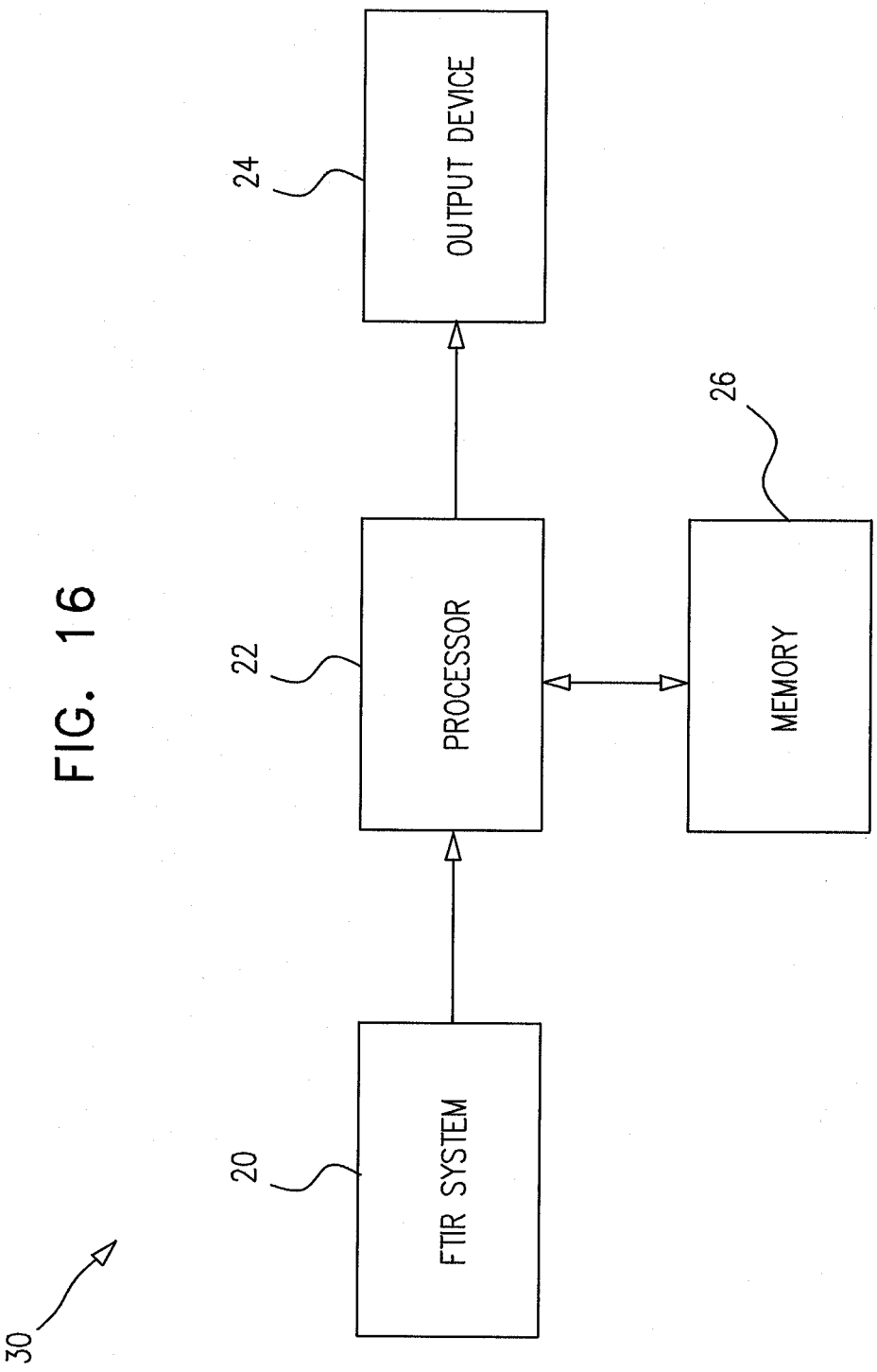

US 9,804,145 B2

INFRARED ANALYSIS OF BENIGN TUMORS

CROSS-REFERENCES TO RELATED APPLICATIONS

The present application is a U.S. National Phase of International Application No. PCT/IL2013/050945 filed Nov. 14, 2013, which claims the benefit of U.S. Provisional Patent Application No. 61/827,933, filed May 28, 2013, in which both applications are incorporated herein by reference.

FIELD OF EMBODIMENTS OF THE INVENTION

Embodiments of the present invention relate generally to diagnosis of tumors, and particularly to methods for differential diagnosis of benign and malignant solid tumors.

BACKGROUND

Infrared spectroscopy is a technique based on the absorption or reflection of infrared radiation by chemical substances, each chemical substance having unique absorption spectra. Fourier Transform Infrared (FTIR) spectroscopy is used to identify biochemical compounds and examine the biochemical composition of a biological sample. Typically, FTIR spectra are composed of several absorption bands each corresponding to specific functional groups related to cellular components such as lipids, proteins, carbohydrates and nucleic acids. Processes such as carcinogenesis may trigger global changes in cancer cell biochemistry, resulting in differences in the absorption spectra when analyzed by FTIR spectroscopy techniques. Therefore, FTIR spectroscopy is commonly used to distinguish between normal and abnormal tissue by analyzing the changes in absorption bands of macromolecules such as lipids, proteins, carbohydrates and nucleic acids. Additionally, FTIR spectroscopy may be utilized for evaluation of cell death mode, cell cycle progression and the degree of maturation of hematopoietic cells.

Analysis of certain markers (e.g., certain proteins, peptides, RNA molecules) in a patient's circulation may be useful in detection and/or monitoring of cancer. For example, studies have shown that analysis of a patient's blood plasma for certain oncofetal antigens, enzymes and/or miRNA molecules may assist in diagnosis and prognosis of certain types of cancer. FTIR spectroscopy is used for analysis of various compounds in blood plasma such as total proteins, creatinine, amino acids, fatty acids, albumin, glucose, fibrinogen, lactate, triglycerides, glycerol, urea, cholesterol, apolipoprotein and immunoglobulin.

SUMMARY OF EMBODIMENTS OF THE INVENTION

In some applications of the present invention, a method and system are provided for the differential diagnosis of pre-malignant, malignant, and benign tumors. Accordingly, some applications of the present invention allow distinguishing between subjects suffering from a pre-malignant or a malignant condition and subjects with a benign, non-malignant tumor.

Some applications of the present invention provide a method comprising obtaining an infrared (IR) spectrum of a Peripheral Blood Mononuclear Cells (PBMC) sample of a subject by analyzing the sample by infrared spectroscopy; and based on the infrared spectrum, generating an output indicative of the presence of a benign tumor of the subject.

Additionally or alternatively, some applications of the present invention provide a method comprising obtaining an infrared (IR) spectrum of a plasma sample of a subject by analyzing the sample by infrared spectroscopy; and based on the infrared spectrum, generating an output indicative of the presence of a benign tumor of the subject.

Typically, analysis by infrared (IR) spectroscopy, e.g., FTIR spectroscopy and microspectroscopy (FTIR MSP), of global biochemical properties of blood-derived mononuclear cells or plasma can indicate the presence of a malignant and pre-malignant condition or a benign tumor. In accordance with some applications of the present invention, experiments were carried out in which PBMC or plasma samples from a plurality of subjects having either benign solid tumors or malignant and pre-malignant solid tumors (for example, but not limited to, tumors in breast tissue, gynecological tissues or gastrointestinal tract tissue) were analyzed by FTIR microspectroscopy techniques. Subsequently, the FTIR spectra (absorption and/or reflection) of the PBMC or plasma samples of the subjects with benign tumors were compared to the FTIR spectra of PBMC or plasma samples obtained from the cancer patients and to the FTIR spectra of PBMC or plasma samples obtained from a control group. The control group comprised healthy subjects who did not have identified pre-malignant, malignant or benign tumors.

The inventors have identified that the PBMC or plasma samples obtained from patients suffering from a pre-malignant or malignant solid tumor produce FTIR spectra that differ from those of the control group who do not suffer from a malignant solid tumor, allowing distinguishing between the cancer patients and controls. Furthermore, the inventors have identified that the PBMC or plasma samples obtained from subjects with a benign tumor produce FTIR spectra that differ from those of the cancer patients and those of the control group, allowing distinguishing between subjects with benign tumors, cancer patients and healthy individuals. Thus, some applications of the present invention can be used to diagnose cancer patients suffering from solid tumors and to distinguish a subject with a benign tumor from a cancer patient and a healthy subject. The distinction by FTIR spectroscopy between controls and subjects suffering from either benign or pre-malignant and malignant tumors is typically performed based on analysis of PBMC and blood plasma samples and not of the actual tumor cells, allowing broad population screening if appropriate, and reducing the need in many cases for performing a tissue biopsy.

For some applications, a data processor analyzes the IR spectrum, e.g., the FTIR spectrum, of the PBMC or plasma sample of the subject. Information from the data processor is typically fed into an output unit that generates a result indicative of the presence of a benign tumor and/or a pre-malignant or malignant condition, based on the infrared (IR) spectrum. Additionally, the data processor is typically configured to calculate a second derivative of the infrared (IR) spectrum of the PBMC sample and, based on the second derivative of the infrared (IR) spectrum, to generate an output indicative of the presence of a benign, pre-malignant or malignant tumor.

For some applications, analysis by IR spectroscopy, e.g., FTIR spectroscopy, of the biochemistry of PBMC, plasma or any other blood-derived cells is used for the screening of large populations, aiding in the early detection of solid tumors. Additionally or alternatively, applications of the present invention are used for diagnosing pre-malignant or malignant tumors which may require urgent treatment, in contrast to a benign tumor which typically does not require urgent (or any) medical intervention. FTIR spectroscopy (and microspectroscopy) is typically a simple, reagent-free and rapid method suitable for use as a screening test for large populations. Early detection of cancer generally enables early intervention and treatment, contributing to a reduced mortality rate.

For some applications, the data obtained from both the PBMC samples and the blood plasma samples is further analyzed by suitable methods known in the art, e.g., Artificial Neural Network and/or Cluster Analysis, and/or Principal Component Analysis, and/or Linear Discriminant Analysis (LDA) and/or Non Linear Discriminant Analysis and/or other appropriate classification models. Typically, combining analysis of the PBMC and plasma data provides analysis results which present high sensitivity and specificity of about 71% and 95%, respectively.

There is therefore provided in accordance with some applications of the present invention a method including:

obtaining an infrared (IR) spectrum of a Peripheral Blood Mononuclear Cells (PBMC) sample of a subject by analyzing the sample by infrared spectroscopy; and based on the infrared spectrum, generating an output indicative of the presence of a benign tumor of the subject.

For some applications, the method further includes obtaining an infrared (IR) spectrum of a plasma sample of the subject by analyzing the plasma sample by infrared spectroscopy, generating the output includes generating the output indicative of the presence of the benign tumor of the subject in response to the infrared spectroscopic analyzing of the PBMC sample and the plasma sample.

For some applications, generating the output includes indicating via the output that the tumor is not a malignant tumor.

For some applications, generating the output includes indicating via the output that the tumor is not a pre-malignant condition.

For some applications, generating the output includes indicating via the output that the tumor is not a pre-malignant condition and is not a malignant tumor.

For some applications, generating the output includes indicating that the output is differentially indicative of the presence of the benign tumor rather than the absence of a tumor.

For some applications, the benign tumor includes a benign tumor in tissue selected from the group consisting of: breast tissue and gastrointestinal tract tissue, and generating the output includes generating an output indicative of the presence of a benign tumor in the selected tissue.

For some applications, analyzing includes assessing a characteristic of the sample at at least one wavenumber selected from the group consisting of: 837.4±4 cm-1, 1027.9±4 cm-1, 1182.6±4 cm-1, 1213.0±4 cm-1, 1278.1±4 cm-1, 1544.2±4 cm-1, 1011.0±4 cm-1, 1071.7, 1141.7±4 cm-1, 1158.0±4 cm-1, 1181.7±4 cm-1, and 1502.3±4 cm-1, the selected tissue includes the breast tissue, and generating includes generating an output indicative of the presence of a benign tumor in the breast tissue.

For some applications, analyzing includes assessing the characteristic at at least two wavenumbers selected from the group.

For some applications, analyzing includes assessing the characteristic at at least three wavenumbers selected from the group.

For some applications, analyzing includes assessing a characteristic of the sample at at least one wavenumber selected from the group consisting of: 837.4±4 cm-1, 1027.9±4 cm-1, 1182.6±4 cm-1, 1213.0±4 cm-1, 1278.1±4 cm-1, and 1544.2±4 cm-1, and generating the output includes indicating that the output is differentially indicative of the presence of the benign tumor rather than the absence of a tumor.

For some applications, analyzing includes assessing a characteristic of the sample at at least one wavenumber selected from the group consisting of: 1011.0±4 cm-1, 1071.7, 1141.7±4 cm-1, 1158.0±4 cm-1, 1181.7±4 cm-1, and 1502.3±4 cm-1, and generating the output includes indicating that the output is differentially indicative of the presence of the benign tumor rather than a malignant tumor.

For some applications, analyzing includes assessing a characteristic of the sample at at least one wavenumber selected from the group consisting of: 785.4±4 cm-1, 811.9±4 cm-1, 879.9±4 cm-1, 1253.0±4 cm-1, 1485.4±4 cm-1, and 1526.9±4 cm-1, 760.8±4 cm-1, 870.7±4 cm-1, 1371.1±4 cm-1, 1485.9±4 cm-1, 1526.9±4 cm-1, and 1627.1±4 cm-1, the selected tissue includes the gastrointestinal tract tissue, and generating includes generating an output indicative of the presence of a benign tumor in the gastrointestinal tract tissue.

For some applications, analyzing includes assessing the characteristic at at least two wavenumbers selected from the group.

For some applications, analyzing includes assessing the characteristic at at least three wavenumbers selected from the group.

For some applications, analyzing includes assessing a characteristic of the sample at at least one wavenumber selected from the group consisting of: 785.4±4 cm-1, 811.9±4 cm-1, 879.9±4 cm-1, 1253.0±4 cm-1, 1485.4±4 cm-1, and 1526.9±4 cm-1, and generating the output includes indicating that the output is differentially indicative of the presence of the benign tumor rather than the absence of a tumor.

For some applications, analyzing includes assessing a characteristic of the sample at at least one wavenumber selected from the group consisting of: 760.8±4 cm-1, 870.7±4 cm-1, 1371.1±4 cm-1, 1485.9±4 cm-1, 1526.9±4 cm-1, and 1627.1±4 cm-1, and generating the output includes indicating that the output is differentially indicative of the presence of the benign tumor rather than a malignant tumor.

For some applications, analyzing the sample includes obtaining a second derivative of the infrared (1R) spectrum of the sample.

There is further provided in accordance with some applications a method including:

obtaining an infrared (IR) spectrum of a plasma blood sample of a subject by analyzing the sample by infrared spectroscopy; and based on the infrared spectrum, generating an output indicative of the presence of a benign tumor of the subject.

For some applications, generating the output includes indicating via the output that the tumor is not a malignant tumor.

For some applications, generating the output includes indicating via the output that the tumor is not a pre-malignant condition.

For some applications, generating the output includes indicating via the output that the tumor is not a pre-malignant condition and is not a malignant tumor.

For some applications, generating the output includes indicating that the output is differentially indicative of the presence of the benign tumor rather than the absence of a tumor.

For some applications, the benign tumor includes a benign tumor in tissue selected from the group consisting of: breast tissue and gastrointestinal tract tissue, and generating the output includes generating an output indicative of the presence of a benign tumor in the selected tissue.

For some applications, analyzing includes assessing a characteristic of the sample at at least one wavenumber selected from the group consisting of: 761.3±4 cm-1, 1117.5±4 cm-1, 1152.3±4 cm-1, 1310.9±4 cm-1, 1388.0±4 cm-1, and 1453.6±4 cm-1, 761.7±4 cm-1, 1020.2±4 cm-1, 1249.2±4 cm-1, 1560.1±4 cm-1, 1647.9±4 cm-1, and 1736.1±4 cm-1, the selected tissue includes the breast tissue, and generating includes generating an output indicative of the presence of a benign tumor in the breast tissue.

For some applications, analyzing includes assessing the characteristic at at least two wavenumbers selected from the group.

For some applications, analyzing includes assessing the characteristic at at least three wavenumbers selected from the group.

For some applications, analyzing includes assessing a characteristic of the sample at at least one wavenumber selected from the group consisting of: 761.3±4 cm-1, 1117.5±4 cm-1, 1152.3±4 cm-1, 1310.9±4 cm-1, 1388.0±4 cm-1, and 1453.6±4 cm-1, and generating the output includes indicating that the output is differentially indicative of the presence of the benign tumor rather than the absence of a tumor.

For some applications, analyzing includes assessing a characteristic of the sample at at least one wavenumber selected from the group consisting of: 761.7±4 cm-1, 1020.2±4 cm-1, 1249.2±4 cm-1, 1560.1±4 cm-1, 1647.9±4 cm-1, and 1736.1±4 cm-1, and generating the output includes indicating that the output is differentially indicative of the presence of the benign tumor rather than a malignant tumor.

For some applications, analyzing includes assessing a characteristic of the sample at at least one wavenumber selected from the group consisting of: 780.1±4 cm-1, 872.6±4 cm-1, 1142.1±4 cm-1, 1378.9±4 cm-1, 1399.6±4 cm-1, and 1622.8±4 cm-1, 948.3±4 cm-1, 1034.6±4 cm-1, 1110.3±4 cm-1, 1153.2±4 cm-1, 1340.3±4 cm-1, and 1378.4±4 cm-1, the selected tissue includes the gastrointestinal tract tissue, and generating includes generating an output indicative of the presence of a benign tumor in the gastrointestinal tract tissue.

For some applications, analyzing includes assessing the characteristic at at least two wavenumbers selected from the group.

For some applications, analyzing includes assessing the characteristic at at least three wavenumbers selected from the group.

For some applications, analyzing includes assessing a characteristic of the sample at at least one wavenumber selected from the group consisting of: 780.1±4 cm-1, 872.6±4 cm-1, 1142.1±4 cm-1, 1378.9±4 cm-1, 1399.6±4 cm-1, and 1622.8±4 cm-1, and generating the output includes indicating that the output is differentially indicative of the presence of the benign tumor rather than the absence of a tumor.

For some applications, analyzing includes assessing a characteristic of the sample at at least one wavenumber selected from the group consisting of: 948.3±4 cm-1, 1034.6±4 cm-1, 1110.3±4 cm-1, 1153.2±4 cm-1, 1340.3±4 cm-1, and 1378.4±4 cm-1, and generating the output includes indicating that the output is differentially indicative of the presence of the benign tumor rather than a malignant tumor.

For some applications, analyzing the sample includes obtaining a second derivative of the infrared (IR) spectrum of the sample.

There is additionally provided in accordance with some applications a method including:

obtaining an infrared (IR) spectrum of a Peripheral Blood Mononuclear Cells (PBMC) sample by analyzing the sample by infrared spectroscopy; and based on the infrared spectrum, generating an output indicative of the presence of a solid tumor in gynecological tissue of a subject.

For some applications, the solid tumor in gynecological tissue includes a solid tumor in tissue selected from the group consisting of: ovarian tissue, endometrial tissue, and cervical tissue, and generating the output includes generating an output indicative of the presence of a solid tumor in tissue selected from the group.

For some applications, the solid tumor is a sarcoma.

There is still provided in accordance with some applications a method including:

obtaining an infrared (IR) spectrum of a blood plasma sample by analyzing the sample by infrared spectroscopy; and based on the infrared spectrum, generating an output indicative of the presence of a solid tumor in gynecological tissue of a subject.

For some applications, the solid tumor in gynecological tissue includes a solid tumor in tissue selected from the group consisting of: ovarian tissue, endometrial tissue, and cervical tissue, and generating the output includes generating an output indicative of the presence of a solid tumor in tissue selected from the group.

For some applications, the solid tumor is a sarcoma.

There is still further provided in accordance with some applications a method including:

obtaining an infrared (IR) spectrum of a Peripheral Blood Mononuclear Cells (PBMC) sample of a subject and an infrared (IR) spectrum of a plasma sample of the subject by analyzing the sample by infrared spectroscopy; and based on the infrared spectrum, generating an output indicative of the presence of a solid malignant tumor of the subject, generating the output includes generating the output indicative of the presence of the tumor of the subject in response to the infrared spectroscopic analyzing of the PBMC sample and the plasma sample.

There is further provided in accordance with some applications a method including:

obtaining an infrared (IR) spectrum of a population of Peripheral Blood Mononuclear Cells (PBMC) from a subject exhibiting a clinical parameter that may trigger a false positive diagnosis of a malignant condition, by analyzing the cells by infrared spectroscopy; and based on the infrared (IR) spectrum, generating an output that is differentially indicative of the presence of a malignant condition versus the presence of a clinical parameter that may trigger a false positive diagnosis.

For some applications, the subject exhibiting a clinical parameter that may trigger a false positive diagnosis of a malignant condition includes a pregnant woman, and generating an output includes generating an output that is differentially indicative of the presence of a malignant condition versus the presence of a pregnancy.

There is yet further provided in accordance with some applications a method including:

obtaining an infrared (IR) spectrum of a blood plasma sample from a subject exhibiting a clinical parameter that may trigger a false positive diagnosis of a malignant condition, by analyzing the sample by infrared spectroscopy; and based on the infrared (IR) spectrum, generating an output that is differentially indicative of the presence of a malignant condition versus the presence of a clinical parameter that may trigger a false positive diagnosis.

For some applications, the subject exhibiting a clinical parameter that may trigger a false positive diagnosis of a malignant condition includes a pregnant woman, and generating an output includes generating an output that is differentially indicative of the presence of a malignant condition versus the presence of a pregnancy.

There is further provided in accordance with some applications a method including:

obtaining an infrared (IR) spectrum of a Peripheral Blood Mononuclear Cells (PBMC) sample of a subject by analyzing the sample by infrared spectroscopy;

analyzing the infrared spectrum using a processor; and based on the analyzing using the processor, using an output device, generating an output indicative of the presence of a benign tumor of the subject.

There is further provided in accordance with some applications a method including:

obtaining an infrared (IR) spectrum of a plasma blood sample of a subject by analyzing the sample by infrared spectroscopy;

analyzing the infrared spectrum using a processor; and based on the analyzing using the processor, using an output device, generating an output indicative of the presence of a benign tumor of the subject.

There is further provided in accordance with some applications a method including:

obtaining an infrared (IR) spectrum of a Peripheral Blood Mononuclear Cells (PBMC) sample from a subject, by analyzing the sample by infrared spectroscopy;

analyzing the infrared spectrum, using a processor; and based on the analyzing using the processor, using an output device, generating an output indicative of the presence of a solid tumor in gynecological tissue of the subject.

There is further provided in accordance with some applications a method including:

obtaining an infrared (IR) spectrum of a blood plasma sample of a subject by analyzing the sample by infrared spectroscopy;

analyzing the infrared spectrum using a processor; and based on the analyzing using the processor, using an output device, generating an output indicative of the presence of a solid tumor in gynecological tissue of the subject.

There is further provided in accordance with some applications a method including:

obtaining an infrared (IR) spectrum of a Peripheral Blood Mononuclear Cells (PBMC) sample of a subject and an infrared (IR) spectrum of a plasma sample of the subject by analyzing the sample by infrared spectroscopy;

analyzing the infrared spectrum using a processor; and based on the analyzing using the processor, using an output device, generating an output indicative of the presence of a solid malignant tumor of the subject, wherein generating the output comprises generating the output indicative of the presence of the tumor of the subject in response to the infrared spectroscopic analyzing of the PBMC sample and the plasma sample.

There is further provided a method for diagnosis of a solid tumor, the method including:

obtaining an infrared (IR) spectrum of a population of Peripheral Blood Mononuclear Cells (PBMC) from a subject exhibiting a clinical parameter that may trigger a false positive diagnosis of a malignant condition, by analyzing the cells by infrared spectroscopy;

analyzing the infrared spectrum using a processor; and based on the analyzing using the processor, using an output device, generating an output that is differentially indicative of the presence of a malignant condition versus the presence of a clinical parameter that may trigger a false positive diagnosis.

There is further provided a method for diagnosis of a solid tumor, the method including:

obtaining an infrared (IR) spectrum of a blood plasma sample from a subject exhibiting a clinical parameter that may trigger a false positive diagnosis of a malignant condition, by analyzing the sample by infrared spectroscopy;

analyzing the infrared spectrum using a processor; and based on the analyzing using the processor, using an output device, generating an output that is differentially indicative of the presence of a malignant condition versus the presence of a clinical parameter that may trigger a false positive diagnosis.

There is further provided in accordance with some applications a computer program product for administering processing of a body of data, the product including a computer-readable medium having program instructions embodied therein, which instructions, when read by a computer, cause the computer to:

obtain an infrared (IR) spectrum of a blood plasma sample by analyzing the blood plasma sample by infrared spectroscopy; and based on the infrared spectrum, generate an output indicative of the presence of a benign tumor.

There is further provided in accordance with some applications computer program product for administering processing of a body of data, the product including a computer-readable medium having program instructions embodied therein, which instructions, when read by a computer, cause the computer to:

obtain an infrared (IR) spectrum of a Peripheral Blood Mononuclear Cells (PBMC) sample by analyzing the blood sample by infrared spectroscopy; and based on the infrared spectrum, generate an output indicative of the presence of a benign tumor.

There is further provided in accordance with some applications system for diagnosing a benign tumor, including:

a processor, configured to analyze an infrared (IR) spectrum of a blood plasma sample of a subject; and an output device, configured to generate an output indicative of the presence of a benign tumor, based on the infrared (IR) spectrum.

There is further provided in accordance with some applications a system for diagnosing a benign tumor, including:

a processor, configured to analyze an infrared (IR) spectrum of a Peripheral Blood Mononuclear Cells (PBMC) sample of a subject; and an output device, configured to generate an output indicative of the presence of a benign tumor, based on the infrared (IR) spectrum.

The present invention will be more fully understood from the following detailed description of embodiments thereof, taken together with the drawings, in which:

BRIEF DESCRIPTION OF THE DRAWINGS

FIGS. 8A-D are graphs representing analysis of clinical information of colorectal cancer patients, for PBMC samples and plasma samples obtained from the colorectal cancer patients in accordance with some applications of the present invention;

FIG. 16 is a block diagram of a system for differential diagnosis of benign and malignant solid tumors, in accordance with some applications of the present invention.

DETAILED DESCRIPTION OF THE EMBODIMENTS

Figure 1A:
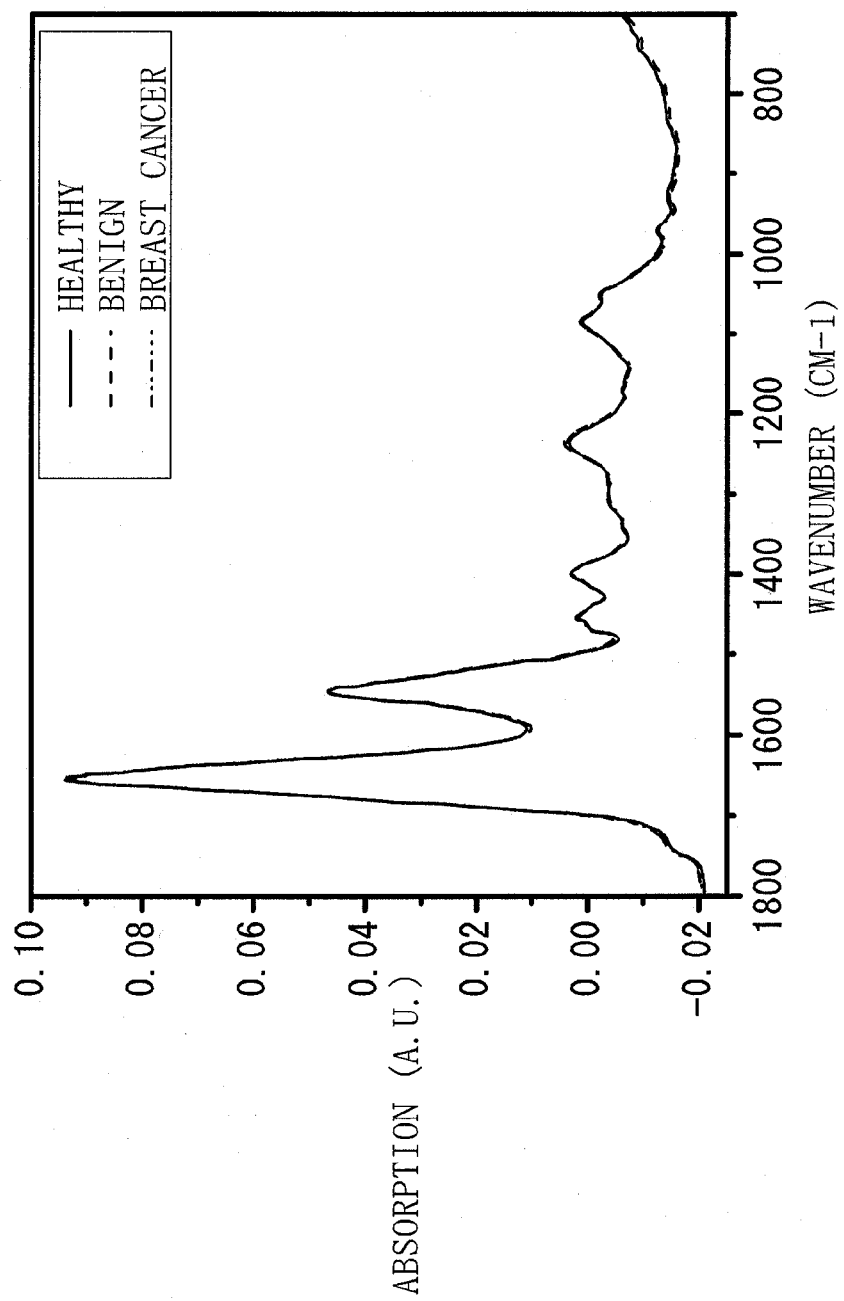
FIGS. 1A-D are graphs representing FTIR absorption spectra, the second derivative of the absorption spectra, and analysis thereof, based on PBMC samples from breast cancer patients, subjects with benign breast tumors, and controls, derived in accordance with some applications of the present invention.

Some applications of the present invention comprise apparatus and methods for performing differential diagnosis of benign and malignant solid tumors by FTIR microspectroscopy (MSP) techniques. In accordance with some applications of the present invention, FTIR microspectroscopy is used to differentially diagnose a solid tumor and a benign tumor based on biochemical properties of a blood and/or plasma sample of a subject. Some applications of the present invention comprise obtaining a blood sample from a subject and analyzing PBMC and/or plasma from the sample by FTIR-MSP techniques for the detection of a malignant or a benign solid tumor. Typically, blood plasma and/or a PBMC sample of a patient having a benign solid tumor is identified as exhibiting FTIR spectra that are different from FTIR spectra produced by blood plasma/PBMC from a subject who has a malignant solid tumor. Additionally, blood plasma and/or a PBMC sample of a patient suffering from a benign solid tumor is identified as exhibiting FTIR spectra that are different from FTIR spectra produced by blood plasma/PBMC from a subject who does not suffer from a malignant or benign solid tumor (for some applications the control group may include subjects suffering from a pathology that is not a solid tumor). Accordingly, some applications of the present invention provide a useful method for diagnosing a cancer patient and distinguishing between a cancer patient and a subject with a benign tumor.

METHODS USED IN SOME EMBODIMENTS OF THE PRESENT INVENTION

A series of protocols are described hereinbelow which may be used separately or in combination, as appropriate, in accordance with applications of the present invention. It is to be appreciated that numerical values are provided by way of illustration and not limitation. Typically, but not necessarily, each value shown is an example selected from a range of values that is within 20% of the value shown. Similarly, although certain steps are described with a high level of specificity, a person of ordinary skill in the art will appreciate that other steps may be performed, mutatis mutandis.

In accordance with some applications of the present invention, the following methods were applied:

Obtaining Patient and Control Populations

All studies were approved by the local Ethics Committee of the Edith Wolfson Medical Center, Holon, Israel, and Beilinson Hospital, Israel. Studies were conducted in accordance with the Declaration of Helsinki. Qualified personnel obtained informed consent from each individual participating in this study.

A first patient population included subjects diagnosed with solid tumors in breast and gastrointestinal tissue as set forth in the following Table A:

TABLE A

|  |  | Breast tissue | | | Gastrointestinal tissue (colorectal) | | |
|---|---|---|---|---|---|---|---|
|  |  | Control | Benign | Cancer | Control | Benign | Cancer |
| Number of subjects. |  | 15 | 15 | 29 | 15 | 14 | 35 |
| Mean age ± SD |  | 42 ± 14 | 46 ± 21 | 60 ± 13 | 55 ± 16 | 71 ± 10 | 67 ± 14 |
| Gender | Male | — | — | — | 8 | 7 | 19 |
|  | Female | 15 | 15 | 29 | 7 | 7 | 16 |
| Disease stage | Pre-malignant | — | — | 0 | — | — | 6 |
|  | I | — | — | 11 | — | — | 6 |
|  | II | — | — | 13 | — | — | 13 |
|  | III | — | — | 2 | — | — | 8 |
|  | IV | — | — | 0 | — | — | 2 |

The diagnosis of cancer was determined by clinical, surgical, histological, and pathologic diagnosis. The pathologic stage of the tumor was determined according to tumor-node-metastasis (TNM) classification, as described in "TNM Classification of Malignant Tumours", by Sobin L H. et al., 7th Edition, New York: John Wiley, 2009. Clinical details for breast and colorectal cancer patient is presented in FIG. 4A.

A control group (n=15) included healthy volunteers.

A second patient population included subjects diagnosed with solid tumors in gynecological tissue as set forth in the following Table B:

TABLE B

|  |  | Control | Breast | Gastro-intestinal | Lung | Other |
|---|---|---|---|---|---|---|
| Mean age ± SD |  | 52 ± 14 | 59 ± 12 | 66 ± 13 | 59 ± 8 | 47 ± 15 |
| Gender | Male | 18 | 0 | 27 | 9 | 3 |
|  | Female | 37 | 42 | 24 | 2 | 2 |
| Disease stage | Pre | 0 | 0 | 6 | 0 | 0 |
|  | I | 0 | 11 | 3 | 0 | 1 |
|  | II | 0 | 17 | 13 | 1 | 0 |
|  | III | 0 | 4 | 11 | 3 | 1 |
|  | IV | 0 | 1 | 8 | 7 | 0 |

The diagnosis of cancer was determined by clinical, surgical, histological, and pathologic diagnosis. The pathologic stage of the tumor was determined according to tumor-node-metastasis (TNM) classification, as described in "TNM Classification of Malignant Tumours", by Sobin L H. et al., 7th Edition, New York: John Wiley, 2009.

A control group (n=28) included healthy volunteers.

An additional control group consisted of pregnant women (n=11).

Collection of Blood Samples 1-2 ml of peripheral blood was collected in 5 ml EDTA blood collection tubes (BD Vacutainer® Tubes, BD Vacutainer, Toronto) from patients and controls using standardized phlebotomy procedures. Samples were processed within two hours of collection.

Extraction of Peripheral Blood Mononuclear Cells (PBMC)

Platelet-depleted residual leukocytes obtained from cancer patients and healthy controls were applied to Histopaque 1077 gradients (Sigma Chemical Co., St. Louis, Mo., USA) following manufacturer's protocol to obtain PBMC.

The cells were aspirated from the interface, washed twice with isotonic saline (0.9% NaCl solution) at 500 g for 7 minutes, and resuspended in 10 ul fresh isotonic saline. The cells were diluted with saline to different concentrations (respectively, by 1×, 2×, 3×, 5× and 6×), and 0.4 ul from each concentration was deposited on zinc selenide (ZnSe) slides to form a uniform layer of dried cells. It is noted that any other suitable slide may be used, e.g., reflection measurements may be carried out using a gold slide. The slides were then air dried for 0.5 h under laminar flow at a temperature of 30±4 C to remove water. The dried cells were then assessed by FTIR microscopy.

Isolation of Plasma from Peripheral Blood Samples

Blood from cancer patients and healthy controls was diluted 1:1 in isotonic saline (0.9% NaCl solution). The diluted blood was applied carefully to Histopaque 1077 gradients (Sigma Chemical Co., St. Louis, Mo., USA) in 15 ml collection tubes, and centrifuged at 400 g for 30 min. To discard platelets and cell debris, the plasma was transferred to 1.5 ml eppendorf tubes and centrifuged at 6000 g for 10 min. Then, 500 ul of the mid section of the plasma was transferred to a new eppendorf tube, and 0.8 ul of plasma was deposited on a zinc selenide (ZnSe) slide. It is noted that any other suitable slide may be used, e.g., reflection measurements may be carried out using a gold slide. The slide was air dried for 0.5 h under laminar flow at a temperature of 30±4 C to remove water. The dried plasma was then subjected to FTIR microscopy.

FTIR-Microspectroscopy

Fourier Transform Infrared Microspectroscopy (FTIR-MSP) and Data Acquisition Measurements were performed using the FTIR microscope Nicolet Centaurus with a liquid-nitrogen-cooled mercury-cadmium-telluride (MCT) detector, coupled to the FTIR spectrometer Nicolet iS10, using OMNIC software (Nicolet, Madison, Wis.). To achieve high signal-to-noise ratio (SNR), 128 coadded scans were collected in each measurement in the wavenumber region 700 to 4000 cm-1. The measurement site was circular, with a diameter of 100 um and spectral resolution of 4 cm-1 (0.482 cm-1 data spacing). To reduce plasma sample thickness variation and achieve proper comparison between different samples, the following procedures were adopted:
1. Each sample was measured at least five times at different spots.
2. Analog to Digital Converter (ADC) rates were empirically chosen between 2000 to 3000 counts/sec (providing measurement areas with similar material density).
3. The obtained spectra were baseline corrected using the rubber band method, with 64 consecutive points, and normalized using vector normalization in OPUS software as described in an article entitled "Early spectral changes of cellular malignant transformation using Fourier transformation infrared microspectroscopy", by Bogomolny et al., 2007. J Biomed Opt. 12:024003.

In order to obtain precise absorption values at a given wavenumber with minimal background interference, the second derivative spectra were used to determine concentrations of bio-molecules of interest. This method is susceptible to changes in FWHM (full width at half maximum) of the IR bands. However, in the case of biological samples, all samples (plasma) from the same type are composed of similar basic components, which give relatively broad bands. Thus, it is possible to generally neglect the changes in band FWHM, as described in an article entitled "Selenium alters the lipid content and protein profile of rat heart: An FTIR microspectroscopy study", by Toyran et al., Arch. Biochem. Biophys. 2007 458:184-193.

Spectra Processing and Statistical Analysis

The IR spectrum reflects biochemical data of the measured sample. To distinguish between cancer and control groups, specific sections from the selected interval of the spectra were selected as determined by the T-test. The differences were considered significant at P<0.05. Data reduction was implemented by Principal Component Analysis (PCA). If each one of the wave numbers is considered as a direction, then the PCA technique searched for new directions in the data that have largest variance and subsequently projected the data onto a new multi-dimensional space. Following the PCA, Fisher's Linear Discriminant Analysis (FLDA) was performed to classify between the cancer and control groups. Leave-One-Out Cross-Validation (LOOCV), which is a common method in FTIR spectral analysis, was used to evaluate the classifier performance. The data were verified by additional unsupervised analytical methods such as cluster analysis using Ward's method and Euclidean distances to further verify the analysis (STATISTICA, StatSoft, Tulsa, Okla.).

EXPERIMENTAL DATA

The experiments described hereinbelow were performed by the inventors in accordance with applications of the present invention and using the techniques described hereinabove.

The experiments presented hereinbelow with reference to Examples 1-4 demonstrate that in accordance with some applications of the present invention, analysis of PBMC samples and/or plasma samples by FTIR-MSP techniques can be used for differential diagnosis of benign and malignant solid tumors based on the FTIR-MSP spectral pattern at selected wavenumbers.

Example 1

In a set of experiments, differential diagnosis of benign breast tumors and malignant breast tumors was performed based on a FTIR-MSP spectral pattern at selected wavenumbers of PBMC samples.

In accordance with applications of the present invention, PBMC samples from 15 healthy controls were analyzed by FTIR-MSP, and a typical FTIR-MSP spectral pattern was established for control PBMC. Additionally, PBMC samples from 29 breast cancer patients were subjected to FTIR-MSP analysis and compared to the control FTIR-MSP spectral pattern. Additionally, PBMC samples from 15 subjects with a benign tumor in breast tissue were subjected to FTIR-MSP analysis and compared to the control FTIR-MSP spectral pattern and to the breast cancer FTIR-MSP spectral pattern. The PBMC samples were obtained by preliminary processing of the peripheral blood in accordance with the protocols described hereinabove with reference to extraction of peripheral blood mononuclear cells (PBMC). The PBMC samples were then analyzed by FTIR-MSP, in accordance with the protocols described hereinabove with reference to FTIR-MSP.

Reference is made to FIGS. 1A-D, which are graphs representing FTIR absorption spectra and the second derivative of the absorption spectra and analysis thereof, for PBMC samples from 29 breast cancer patients, 15 subjects with benign tumors in breast tissue and 15 healthy controls, derived in accordance with some applications of the present invention.

FIG. 1A shows average FTIR-MSP absorption spectra of PBMC samples of healthy controls, subjects with benign breast tumors and breast cancer patients in the regions of 700-1800 cm-1, after baseline correction and vector normalization. Each spectrum represents the average of five measurements at different sites for each sample. The spectra are composed of several absorption bands, each corresponding to specific functional groups of specific macromolecules such as lipids, proteins, carbohydrates and nucleic acids. Generally, the FTIR spectrum is typically analyzed by tracking changes vs. control in absorption (intensity and/or shift) of these macromolecules.

Table C represents some of the main IR absorption bands for PBMC cells, and their corresponding molecular functional groups:

TABLE C

| Wavenumber (cm-1 ± 4) | Assignment |
|---|---|
| 2958 | $v_{as}$ $CH_3$, mostly proteins, lipids |
| 2922 | $v_{as}$ $CH_2$, mostly lipids, proteins |
| 2873 | $v_s$ $CH_3$, mostly proteins, lipids |
| 2854 | $v_s$ $CH_2$, mostly lipids, proteins |
| ~1,656 | Amide I v C=O (80%), v C—N (10%), δ N—H |
| ~1,546 | Amide II δ N—H (60%), v C—N (40%) |
| 1400 | v COO—, δ s CH3 lipids, proteins |
| 1313 | Amide III band components of proteins |
| 1240 | $v_{as}$ $PO_2^-$, phosphodiester groups of nucleic acids |
| 1170 | C—O bands from glycomaterials and proteins |
| 1155 | vC—O of proteins and carbohydrates |
| 1085 | vs PO2— of nucleic acids, phospholipids, proteins |
| 1053 | v C—O & δ C—O of carbohydrates |
| 996 | C—C & C—O of ribose of RNA |
| 967 | C—C & C—O of deoxyribose skeletal motions of DNA |
| 780 | sugar-phosphate Z conformation of DNA |
| 740 | v N=H of Thymine |

Figure 1B:
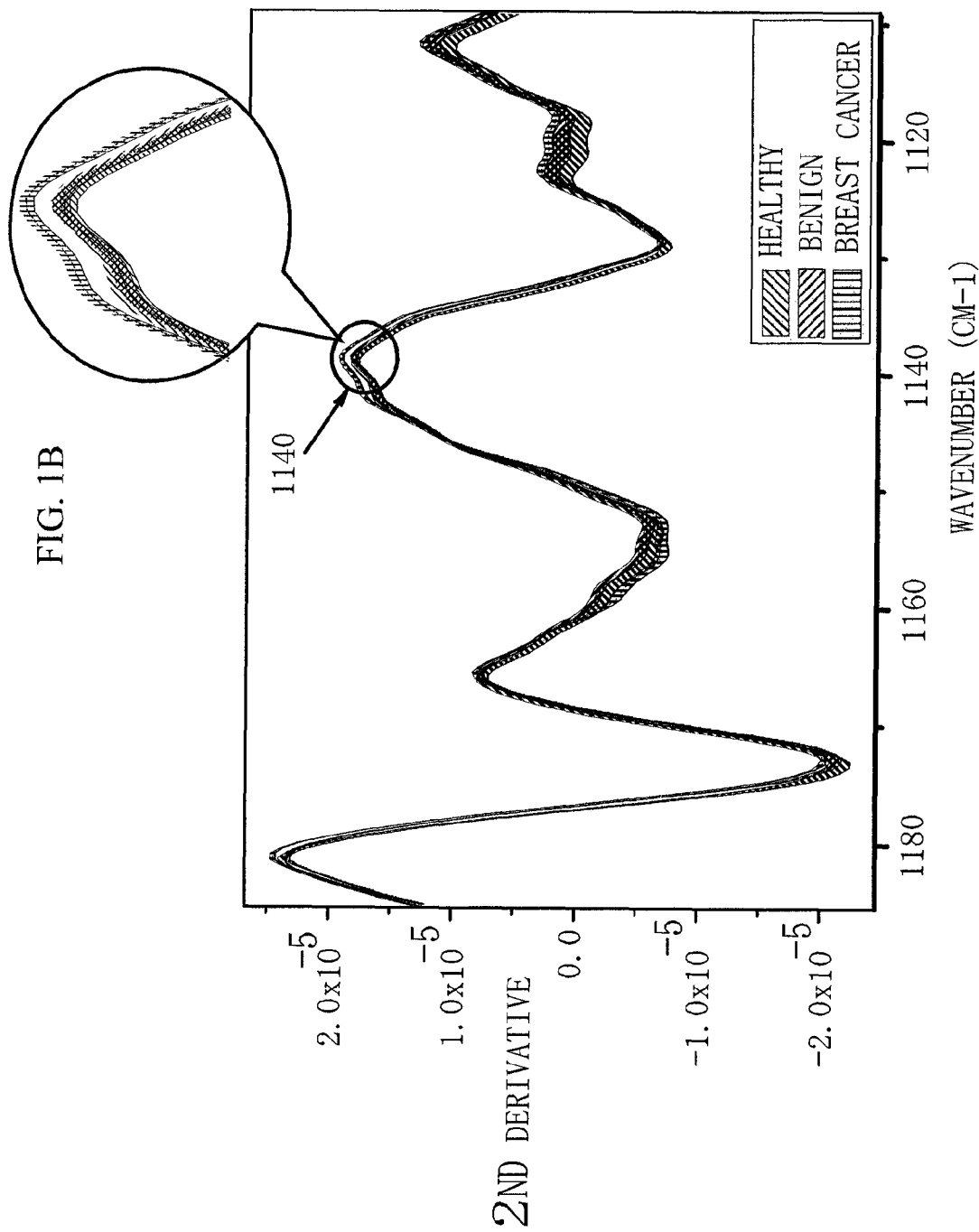

Reference is made to FIG. 1B. In order to achieve effective comparison between the PBMC samples of the breast cancer patients, subjects with benign breast tumors and the controls, the second derivative of the baseline-corrected, vector-normalized FTIR-MSP spectra was used. Results are presented in FIG. 1B. As shown from the second derivative spectra analysis, the spectra of PBMC samples from the breast cancer patients differed significantly from the spectra of PBMC samples from both the subjects with benign breast tumors and the controls, in the spectral region of 1140 cm-1.

The mean±standard error of the mean SEM for each of the data sets (healthy, benign, breast cancer) is represented by the thickness of the graph lines representing the healthy, benign, and breast cancer groups, in accordance with the figure legend, as shown in FIG. 1B.

Figure 1C:
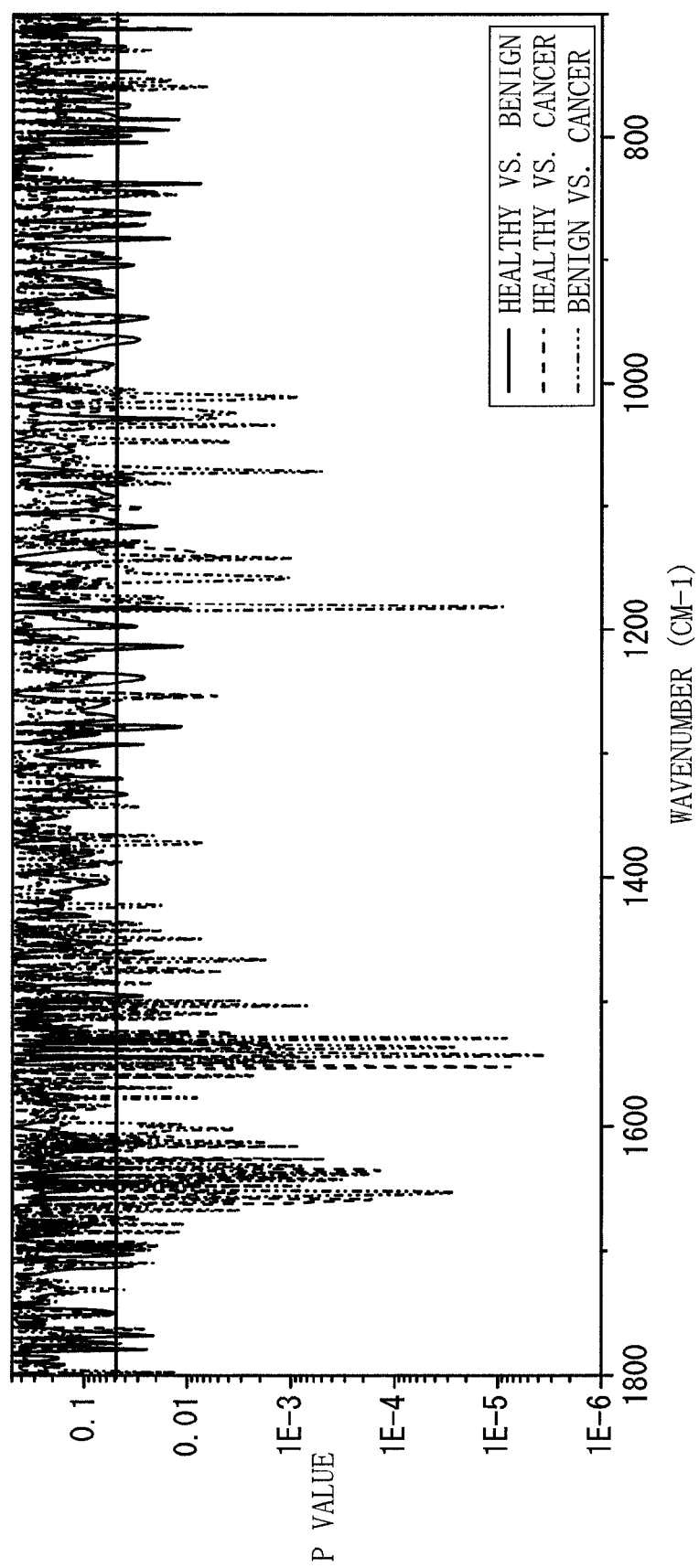
Figure 1D:
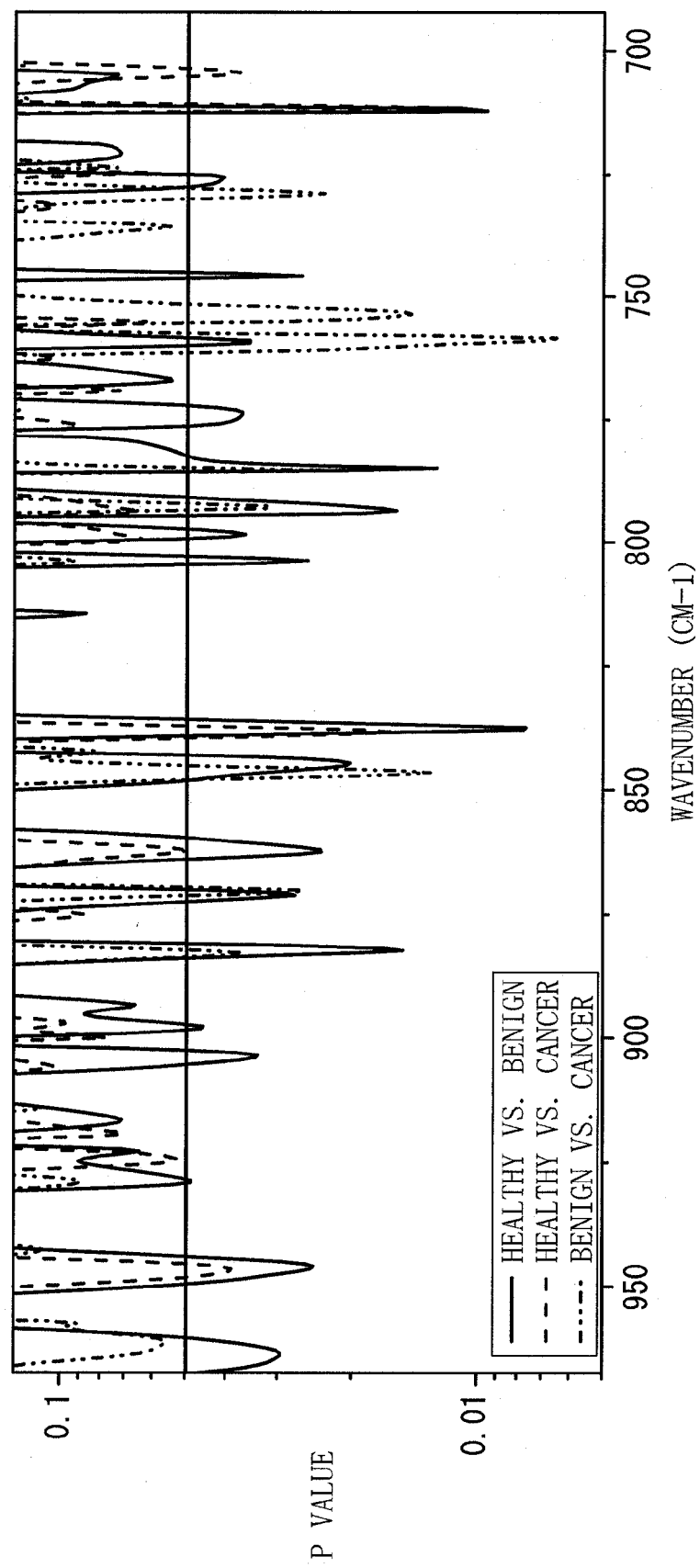

Reference is made to FIGS. 1C-D, which are graphs representing values of the second derivative of absorption spectra of PBMC samples from subjects with benign breast tumors compared to PBMC samples from cancer patients and/or to PBMC samples from healthy controls (indicated as healthy in the figures), derived in accordance with some applications of the present invention. Statistical analysis was performed and p-values are provided. As shown:

a) The second derivative of FTIR-MSP spectra of PBMC samples from the breast cancer patients differed significantly from the second derivative of FTIR-MSP spectra from PBMC of healthy controls;

b) The second derivative of FTIR-MSP spectra of PBMC samples from the breast cancer patients differed significantly from the second derivative of FTIR-MSP spectra from PBMC of subjects with a benign breast tumor; and c) The second derivative of FTIR-MSP spectra of PBMC samples from the subjects with a benign breast tumor differed significantly from the second derivative of FTIR-MSP spectra from PBMC of healthy controls.

Table D lists wavenumbers that were identified in this set of experiments as presented in FIGS. 1A-D. Typically, PBMC samples were analyzed by FTIR-MSP techniques using these wavenumbers to distinguish between: a) healthy control and breast cancer patients; b) healthy control and subjects with benign breast tumors; and c) breast cancer patients and subjects with benign breast tumors. For some applications, the PBMC samples are analyzed by FTIR-MSP at at least one wavenumber selected from Table D. Alternatively, the PBMC samples are analyzed by FTIR-MSP at at least two or three wavenumbers selected from Table D.

For some applications, one, two, three, or more of the following wavenumbers selected from Table D are used to differentiate between the absence of a tumor and a benign breast tumor: 837.4±4 cm-1, 1027.9±4 cm-1, 1182.6±4 cm-1, 1213.0±4 cm-1, 1278.1±4 cm-1, 1544.2±4 cm-1.

For some applications, one, two, three, or more of the following wavenumbers selected from Table D are used to differentiate between a malignant breast tumor and a benign breast tumor: 1011.0±4 cm-1, 1071.7, 1141.7±4 cm-1, 1158.0±4 cm-1, 1181.7±4 cm-1, 1502.3±4 cm-1.

Example 2

In a set of experiments, differential diagnosis of benign breast tumors and malignant breast tumors was performed based on a FTIR-MSP spectral pattern of plasma samples at selected wavenumbers In accordance with applications of the present invention, plasma samples from 15 healthy controls were analyzed by FTIR-MSP, and a typical FTIR-MSP spectral pattern was established for control plasma. Additionally, plasma samples from 29 breast cancer patients were subjected to FTIR-MSP analysis and compared to the control FTIR-MSP spectral pattern. Additionally, plasma samples from 15 subjects with a benign tumor in breast tissue were subjected to FTIR-MSP analysis and compared to the control FTIR-MSP spectral pattern and to the breast cancer FTIR-MSP spectral pattern. The plasma samples were obtained by preliminary processing of the peripheral blood in accordance with the protocols described hereinabove with reference to isolation of plasma from peripheral blood samples. The blood plasma samples were then analyzed by FTIR-MSP, in accordance with the protocols described hereinabove with reference to FTIR-MSP.

Reference is made to FIGS. 2A-D, which are graphs representing FTIR absorption spectra and the second derivative of the absorption spectra and analysis thereof, for plasma samples from 29 breast cancer patients, 15 subjects with benign tumors in breast tissue and 15 healthy controls, derived in accordance with some applications of the present invention.

TABLE D

| Healthy control vs. Benign Wavenumber (cm-1 ± 4) | | | Healthy control vs. Cancer Wavenumber (cm-1 ± 4) | | | Benign vs. Cancer Wavenumber (cm-1 ± 4) | | |
|---|---|---|---|---|---|---|---|---|
| 712.1 | 928.6 | 1537.5 | 711.6 | 1459.4 | 1608.3 | 729.0 | 1173.0 | 1542.3 |
| 725.6 | 945.9 | 1544.2 | 838.9 | 1465.2 | 1616.1 | 753.1 | 1181.7 | 1548.1 |
| 745.8 | 963.3 | 1612.7 | 946.9 | 1473.3 | 1618.9 | 758.9 | 1197.6 | 1559.2 |
| 758.9 | 1027.9 | 1632.9 | 1010.5 | 1498.4 | 1626.2 | 847.1 | 1253.5 | 1576.5 |
| 773.8 | 1077.5 | 1644.0 | 1082.4 | 1501.8 | 1635.3 | 870.2 | 1341.7 | 1602.1 |
| 784.9 | 1116.1 | 1702.4 | 1100.7 | 1507.1 | 1641.1 | 882.8 | 1372.1 | 1612.7 |
| 793.6 | 1129.6 | 1712.0 | 1115.1 | 1512.4 | 1645.5 | 1003.8 | 1423.2 | 1627.1 |
| 798.4 | 1182.6 | 1778.5 | 1140.7 | 1524.9 | 1647.9 | 1011.0 | 1437.2 | 1637.3 |
| 803.7 | 1196.6 | | 1176.8 | 1528.3 | 1653.2 | 1023.5 | 1449.2 | 1642.1 |
| 837.4 | 1213.0 | | 1213.0 | 1532.2 | 1658.5 | 1034.1 | 1466.1 | 1654.1 |
| 845.2 | 1238.6 | | 1254.0 | 1535.5 | 1674.4 | 1047.2 | 1475.3 | 1659.9 |
| 862.5 | 1271.8 | | 1278.6 | 1542.8 | 1684.5 | 1071.7 | 1498.9 | 1667.6 |
| 871.2 | 1278.1 | | 1366.3 | 1548.1 | 1693.2 | 1080.9 | 1502.3 | 1678.7 |
| 882.3 | 1292.6 | | 1437.2 | 1551.9 | 1698.5 | 1128.2 | 1509.0 | 1709.6 |
| 897.7 | 1320.0 | | 1443.0 | 1559.6 | 1701.4 | 1141.7 | 1524.9 | 1730.8 |
| 903.5 | 1332.6 | | 1453.1 | 1568.8 | 1762.1 | 1158.0 | 1536.0 | |

For some applications, one, two, three, or more of the following wavenumbers selected from Table D are used to differentiate between the absence of a tumor and a malignant breast tumor: 1140.7±4 cm-1, 1254.0±4 cm-1, 1473.3±4 cm-1, 1551.9±4 cm-1, 1635.3±4 cm-1, and 1658.5±4 cm-1.

Figure 2A:
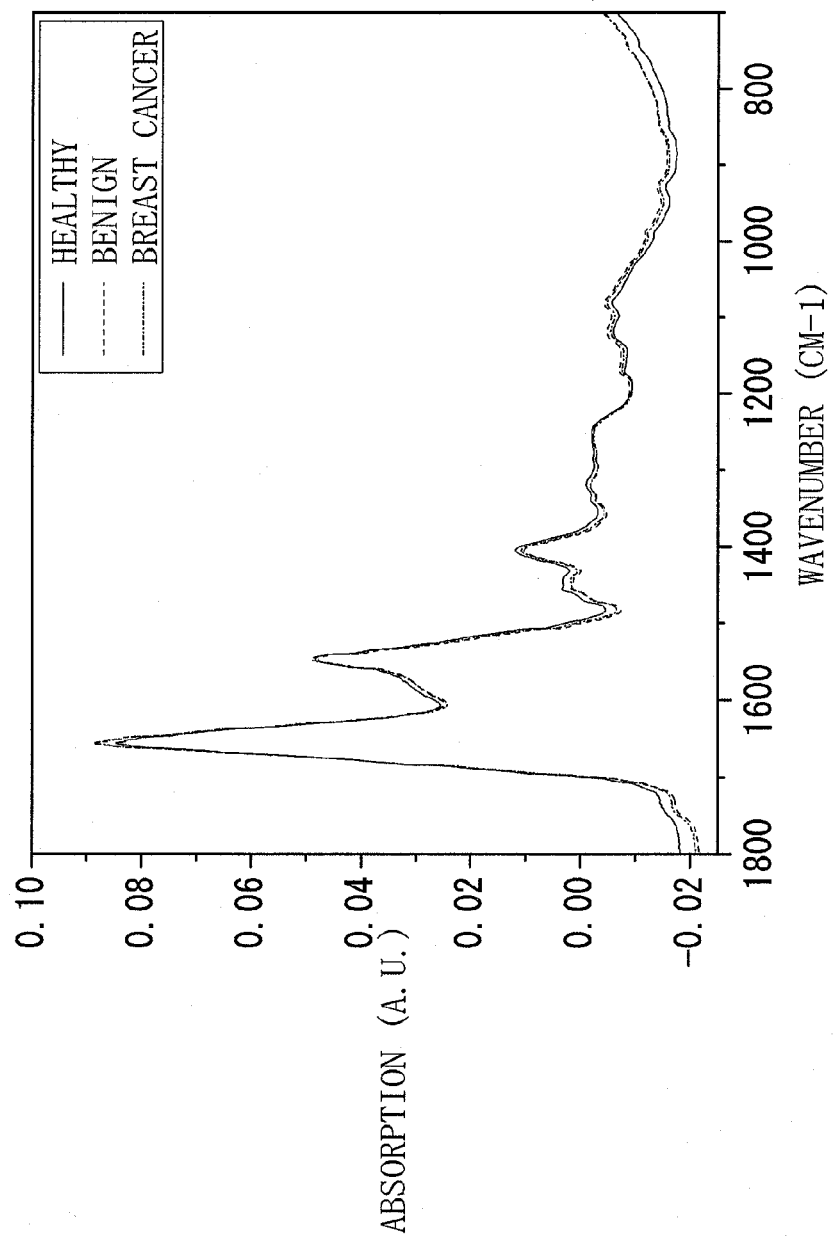
FIGS. 2A-D are graphs representing FTIR absorption spectra, the second derivative of the absorption spectra, and analysis thereof, based on plasma samples from breast cancer patients, subjects with benign breast tumors, and controls, derived in accordance with some applications of the present invention.

FIG. 2A shows average FTIR-MSP absorption spectra of plasma samples of healthy controls, subjects with benign breast tumors and breast cancer patients in the regions of 700-1800 cm-1, after baseline correction and vector normalization. Each spectrum represents the average of five measurements at different sites for each sample. The spectra are composed of several absorption bands, each corresponding to specific functional groups of specific macromolecules such as lipids, proteins, and carbohydrates/nucleic acids. Generally, the FTIR spectrum is typically analyzed by tracking changes in absorption (intensity and/or shift) of these macromolecules.

Figure 2B:
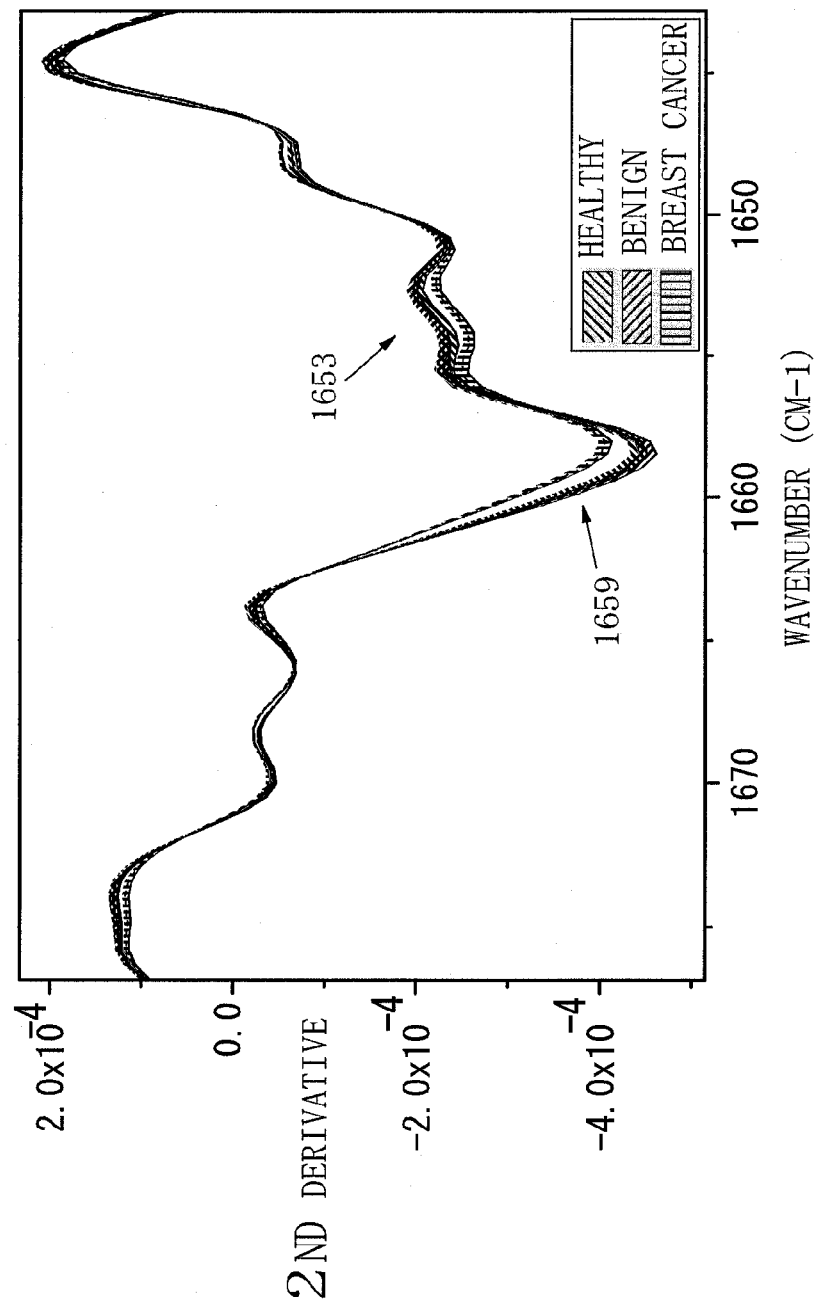

Reference is made to FIG. 2B. In order to achieve effective comparison between the plasma samples of the breast cancer patients, subjects with benign breast tumors and the controls, the second derivative of the baseline-corrected, vector-normalized FTIR-MSP spectra was used. Results are presented in FIG. 2B. As shown from the second derivative spectra analysis, the spectra of the plasma samples from the breast cancer patients differed significantly from the spectra of plasma samples from both the subjects with benign breast tumors and the controls, in the spectral region of 1659 cm-1 and 1653 cm-1.

The mean±SEM for each of the data sets (healthy, benign, breast cancer) is represented by the thickness of the graph lines representing the healthy, benign, and breast cancer groups, in accordance with the figure legend, as shown in FIG. 2B.

Figure 2C:
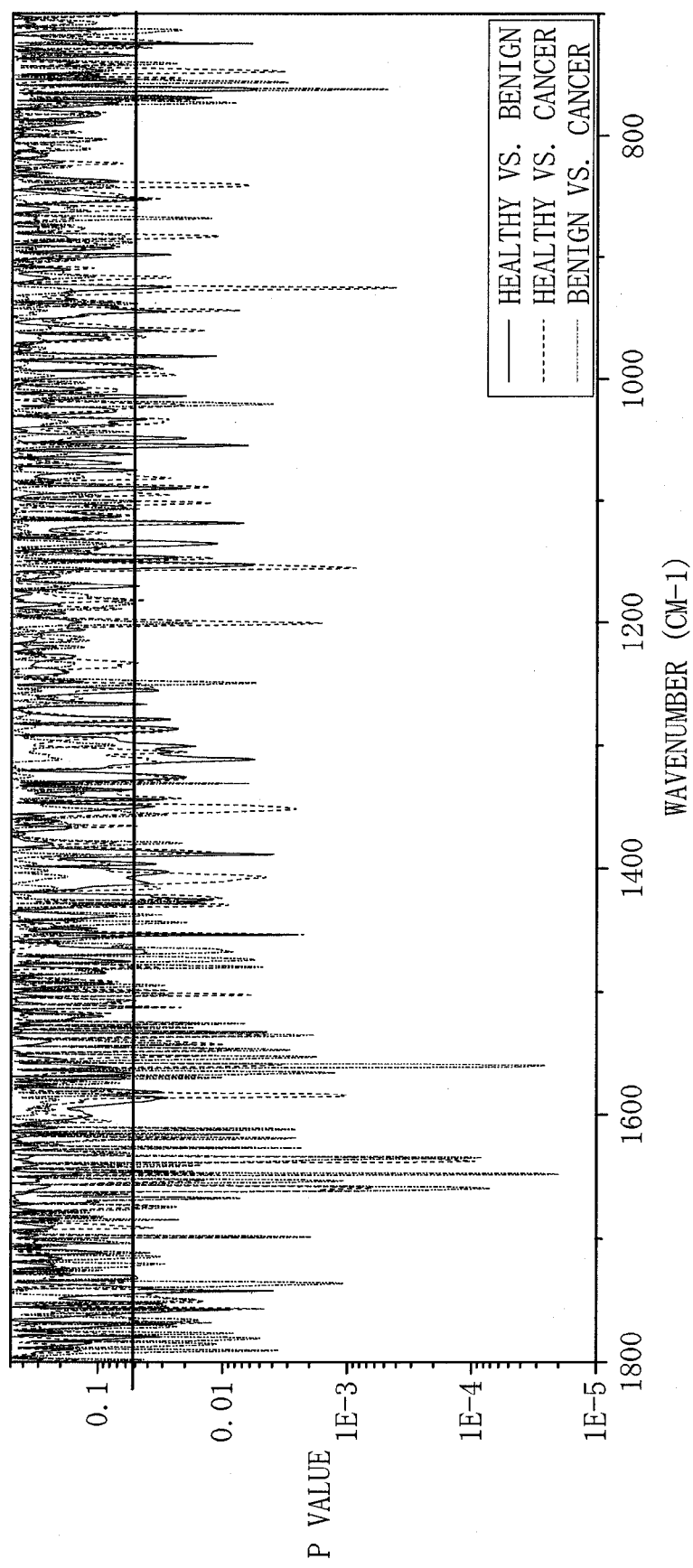
Figure 2D:
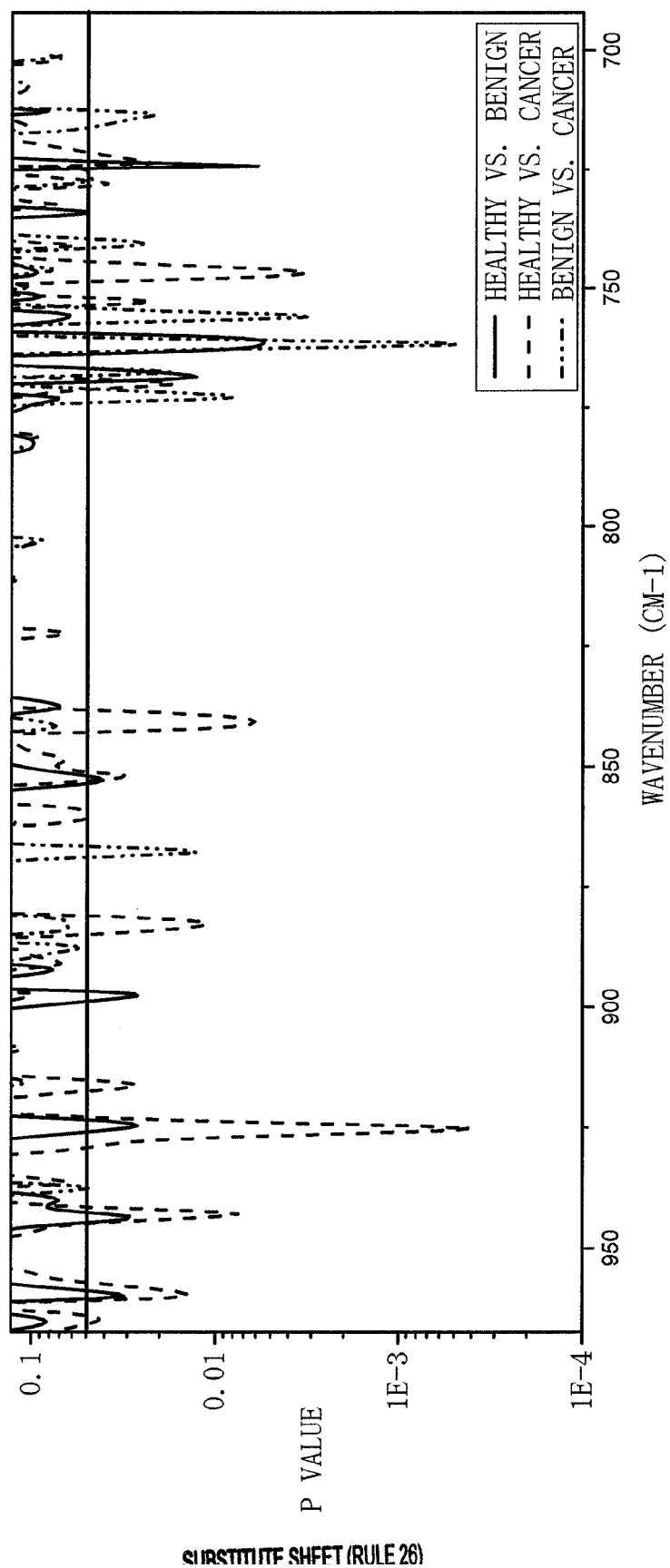

Reference is made to FIGS. 2C-D, which are graphs representing values of the second derivative of absorption spectra of plasma samples from subjects with benign breast tumors compared to plasma samples from cancer patients and/or to plasma samples from healthy controls, derived in accordance with some applications of the present invention. Statistical analysis was performed and p-values are provided. As shown:

a) The second derivative of plasma samples from the breast cancer patients differed significantly from the second derivative analysis of FTIR-MSP spectra from plasma of healthy controls;

b) The second derivative of plasma samples from the breast cancer patients differed significantly from the second derivative analysis of FTIR-MSP spectra from plasma of subjects with a benign breast tumor; and c) The second derivative of plasma samples from the subjects with a benign breast tumor differed significantly from the second derivative analysis of FTIR-MSP spectra from plasma of healthy controls.

Table E1 lists wavenumbers that were identified in this set of experiments as presented in FIGS. 2A-D. Typically, plasma samples were analyzed by FTIR-MSP techniques using these wavenumbers to distinguish between: a) control and breast cancer patients; b) control and subjects with benign breast tumors; and c) breast cancer patients and subjects with benign breast tumors. For some applications, the plasma samples are analyzed by FTIR-MSP at at least one wavenumber selected from Table E1. Alternatively, the plasma samples are analyzed by FTIR-MSP at at least two or three wavenumbers selected from Table E1.

TABLE E1

| Healthy control vs. Benign Wavenumber (cm-1 ± 4) | | Healthy control vs. Cancer Wavenumber (cm-1 ± 4) | | | Benign vs. Cancer Wavenumber (cm-1 ± 4) | | |
|---|---|---|---|---|---|---|---|
| 724.1 | 1286.3 | 723.7 | 1153.2 | 1528.3 | 713.5 | 1512.4 | 1674.9 |
| 761.3 | 1300.3 | 728.0 | 1180.7 | 1532.2 | 726.5 | 1525.4 | 1698.5 |
| 768.5 | 1310.9 | 746.8 | 1200.5 | 1534.6 | 740.5 | 1528.8 | 1736.1 |
| 897.7 | 1325.3 | 752.6 | 1232.8 | 1542.3 | 756.0 | 1532.2 | 1748.6 |
| 924.7 | 1343.7 | 769.9 | 1250.6 | 1547.1 | 761.7 | 1535.1 | 1754.4 |
| 943.5 | 1349.0 | 840.8 | 1279.1 | 1551.9 | 772.8 | 1542.3 | 1758.8 |
| 959.9 | 1388.0 | 883.2 | 1288.2 | 1559.6 | 867.8 | 1547.1 | 1765.5 |
| 980.6 | 1396.2 | 916.5 | 1305.1 | 1584.2 | 1020.2 | 1552.9 | 1770.8 |
| 989.3 | 1402.5 | 925.7 | 1312.8 | 1612.2 | 1200.5 | 1560.1 | 1776.1 |
| 1013.4 | 1411.2 | 943.0 | 1326.8 | 1619.4 | 1249.2 | 1565.9 | 1780.5 |
| 1032.7 | 1425.6 | 958.9 | 1342.2 | 1626.7 | 1267.0 | 1569.8 | 1785.8 |
| 1049.1 | 1453.6 | 965.2 | 1350.9 | 1635.8 | 1330.6 | 1612.2 | 1790.6 |
| 1054.9 | 1466.6 | 980.6 | 1386.6 | 1637.3 | 1355.2 | 1616.1 | |
| 1089.6 | 1581.3 | 990.7 | 1406.8 | 1645.9 | 1378.9 | 1619.4 | |
| 1117.5 | 1587.1 | 1021.6 | 1424.2 | 1652.7 | 1427.1 | 1626.7 | |
| 1134.4 | 1731.3 | 1033.7 | 1429.5 | 1659.9 | 1437.7 | 1634.9 | |
| 1146.0 | 1741.9 | 1081.4 | 1453.6 | 1667.6 | 1443.9 | 1641.1 | |
| 1152.3 | 1752.0 | 1088.6 | 1480.1 | 1673.9 | 1467.6 | 1645.9 | |
| 1169.6 | 1757.3 | 1094.9 | 1498.4 | 1699.0 | 1474.3 | 1647.9 | |
| 1255.4 | 1768.9 | 1101.6 | 1502.3 | 1741.9 | 1479.6 | 1653.2 | |
| 1266.5 | 1779.5 | 1118.0 | 1512.4 | 1756.8 | 1494.6 | 1659.4 | |
| 1279.1 | | 1146.5 | 1524.9 | 1767.9 | 1502.3 | 1667.6 | |

For some applications, one, two, three, or more of the following wavenumbers selected from Table E1 are used to differentiate between the absence of a tumor and a benign breast tumor: 761.3±4 cm-1, 1117.5±4 cm-1, 1152.3±4 cm-1, 1310.9±4 cm-1, 1388.0±4 cm-1, and 1453.6±4 cm-1.

For some applications, one, two, three, or more of the following wavenumbers selected from Table E1 are used to differentiate between the absence of a tumor and a malignant breast tumor: 925.7±4 cm-1, 1153.2±4 cm-1, 1200.5±4 cm-1, 1350.9±4 cm-1, 1453.6±4 cm-1, 1637.3±4 cm-1.

For some applications, one, two, three, or more of the following wavenumbers selected from Table E1 are used to differentiate between a malignant breast tumor and a benign breast tumor: 761.7±4 cm-1, 1020.2±4 cm-1, 1249.2±4 cm-1, 1560.1±4 cm-1, 1647.9±4 cm-1, 1736.1±4 cm-1.

Reference is now made to FIGS. 1A-D, FIGS. 2A-D and FIGS. 3A-G. FIGS. 3A-G are graphs representing statistical analysis including receiver operating characteristic (ROC) curve analysis of the FTIR absorption spectra, based on PBMC and plasma samples from breast cancer patients, subjects with benign breast tumors, and controls, as shown in FIGS. 1A-D and FIGS. 2A-D.

Figure 3A:
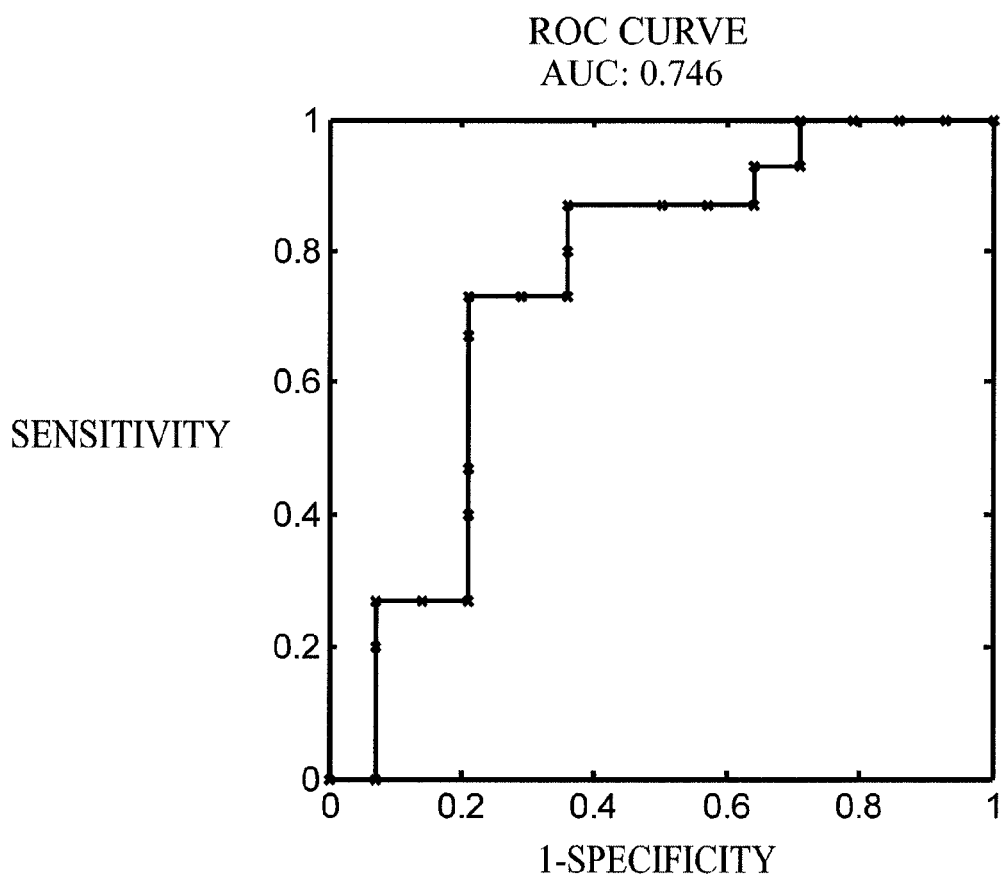
FIGS. 3A-H are graphs representing statistical analysis and cluster analysis thereof including receiver operating characteristic (ROC) curve analysis of the FTIR absorption spectra analysis, based on PBMC and plasma samples from breast cancer patients, subjects with benign breast tumors, and controls, derived in accordance with some applications of the present invention.
Figure 3B:
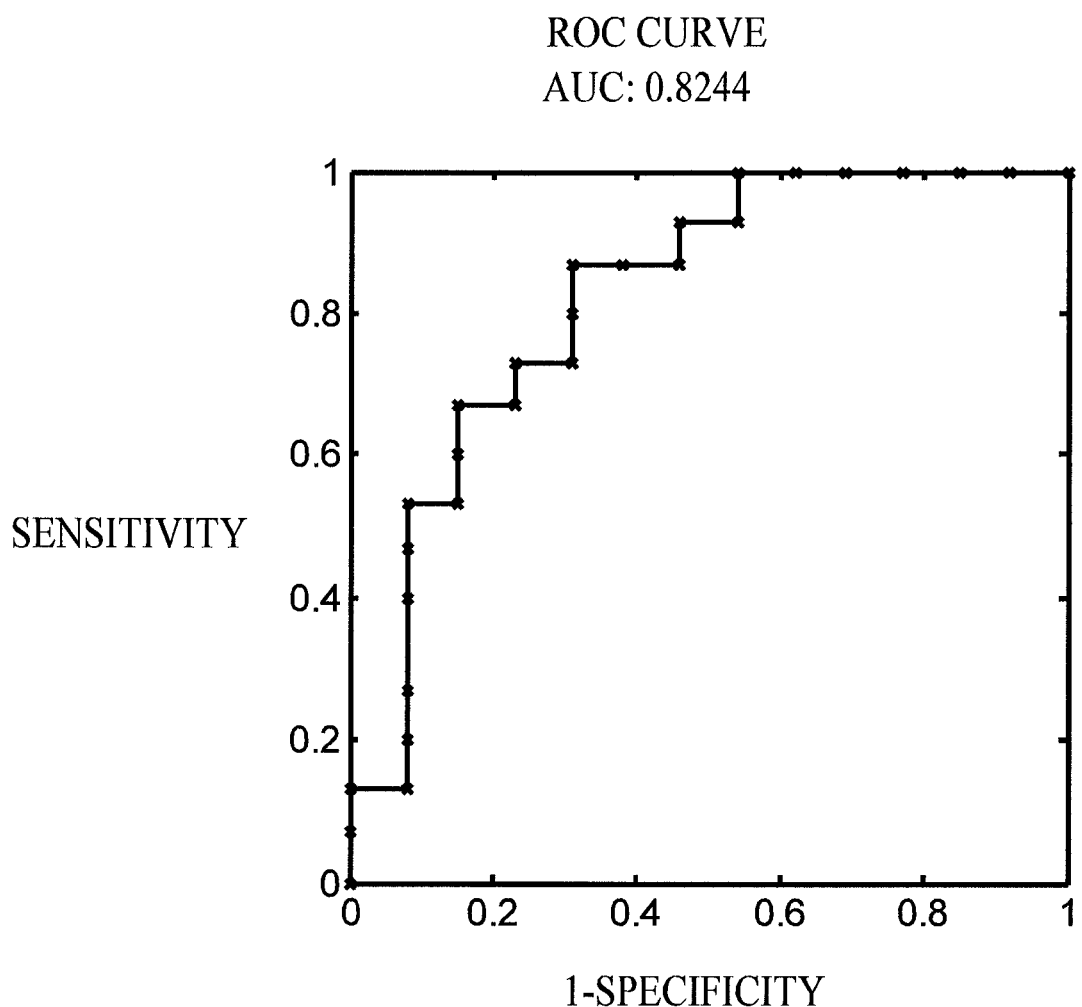
Figure 3C:
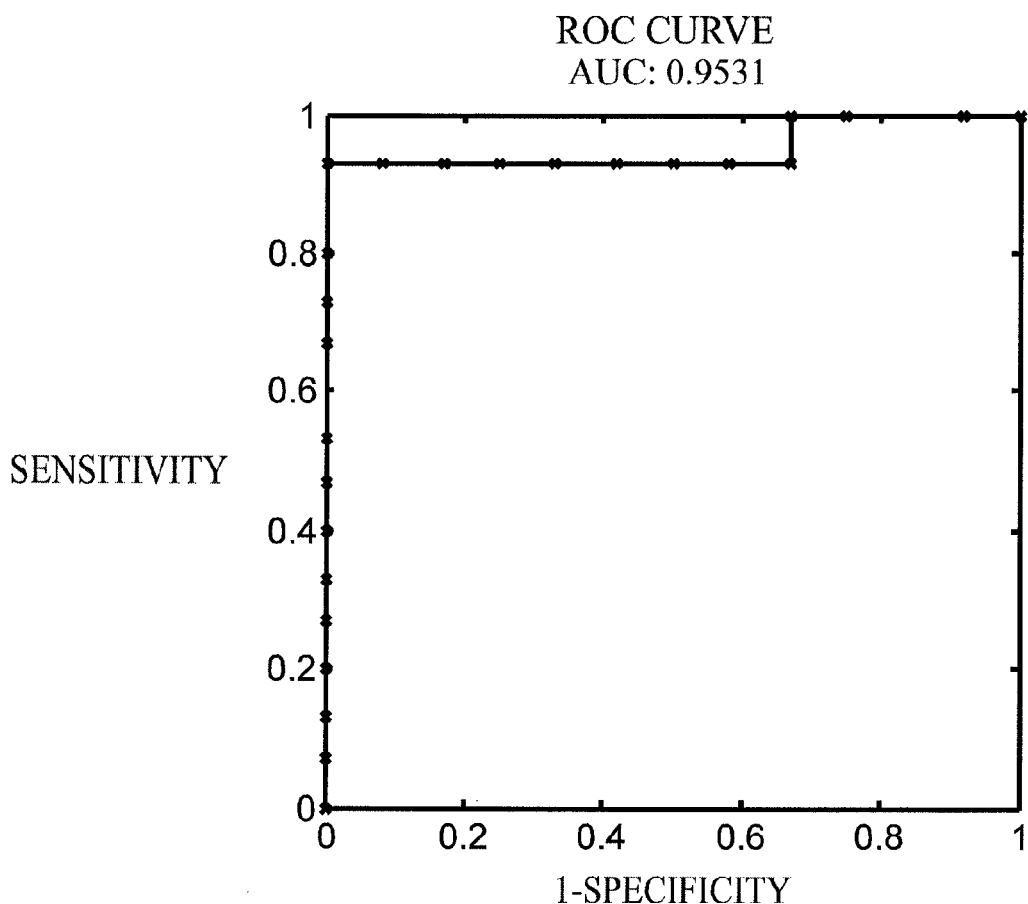

FIGS. 3A-C show receiver operating characteristic (ROC) curve analysis, including the area under the curve (AUC), of PBMC (FIG. 3A) and plasma (FIG. 3B) of healthy controls compared to the subjects with benign breast tumors. As shown, combined use of both the plasma and PBMC samples (FIG. 3C) increased sensitivity and specificity for the diagnosis of a benign breast tumor.

Figure 3D:
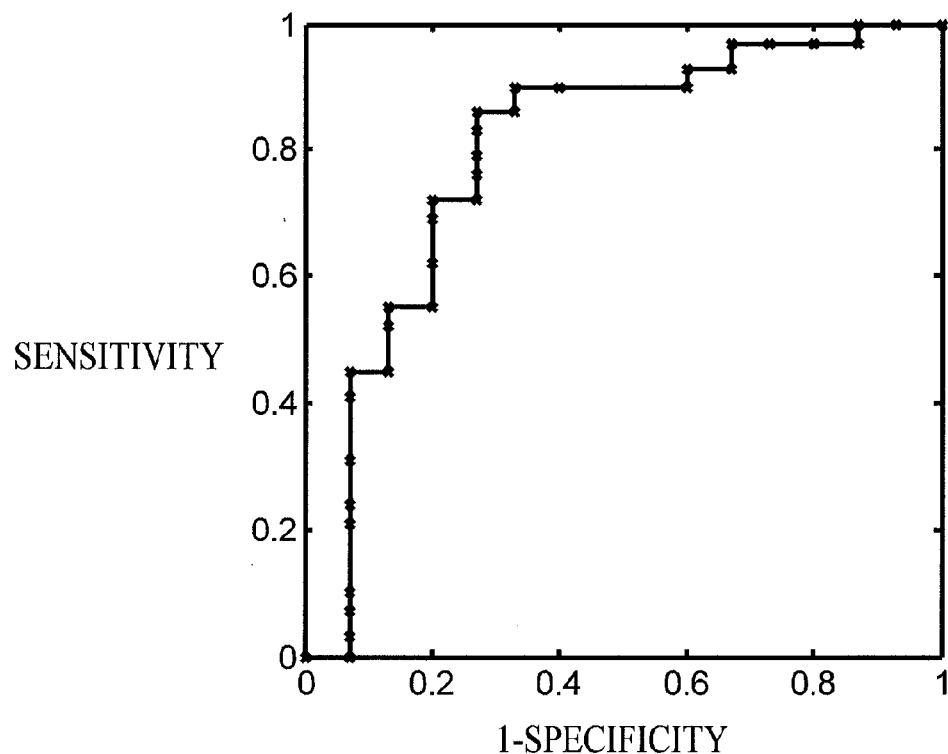
Figure 3E:
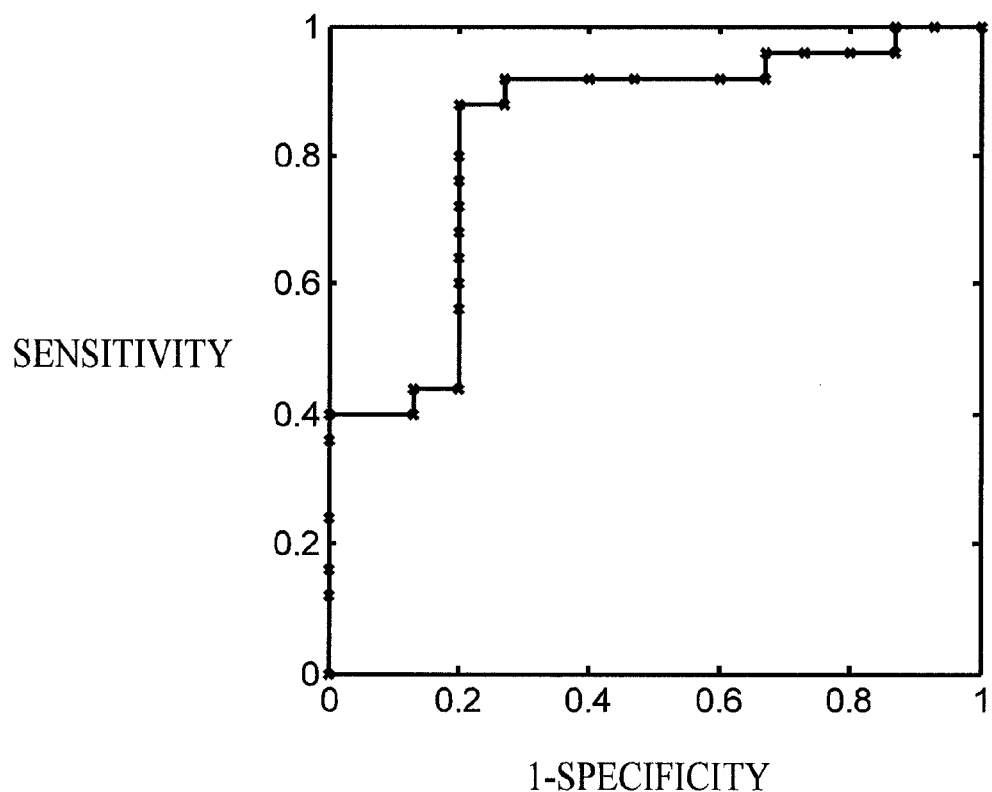
Figure 3F:
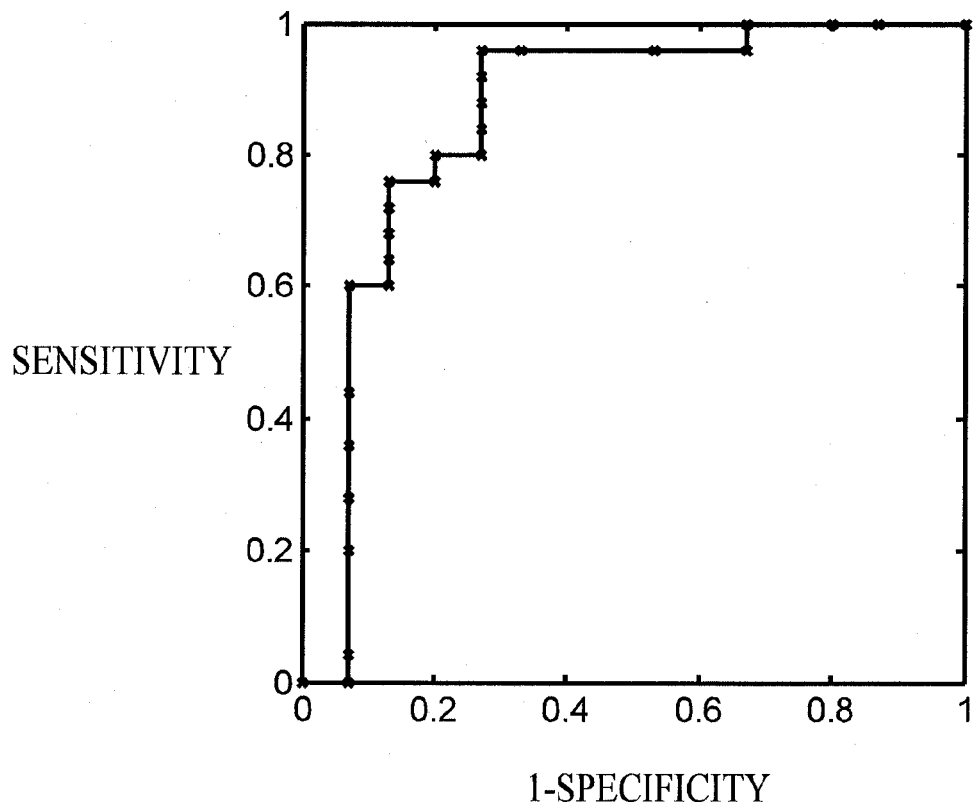

FIGS. 3D-F show receiver operating characteristic (ROC) curve analysis, including the area under the curve (AUC), of PBMC (FIG. 3D) and plasma (FIG. 3E) of breast cancer patients compared to the subjects with benign breast tumors. As shown, combined use of both the plasma and PBMC samples (FIG. 3F) increased sensitivity and specificity for distinguishing between a benign breast tumor and a malignant breast tumor.

Figure 3G:
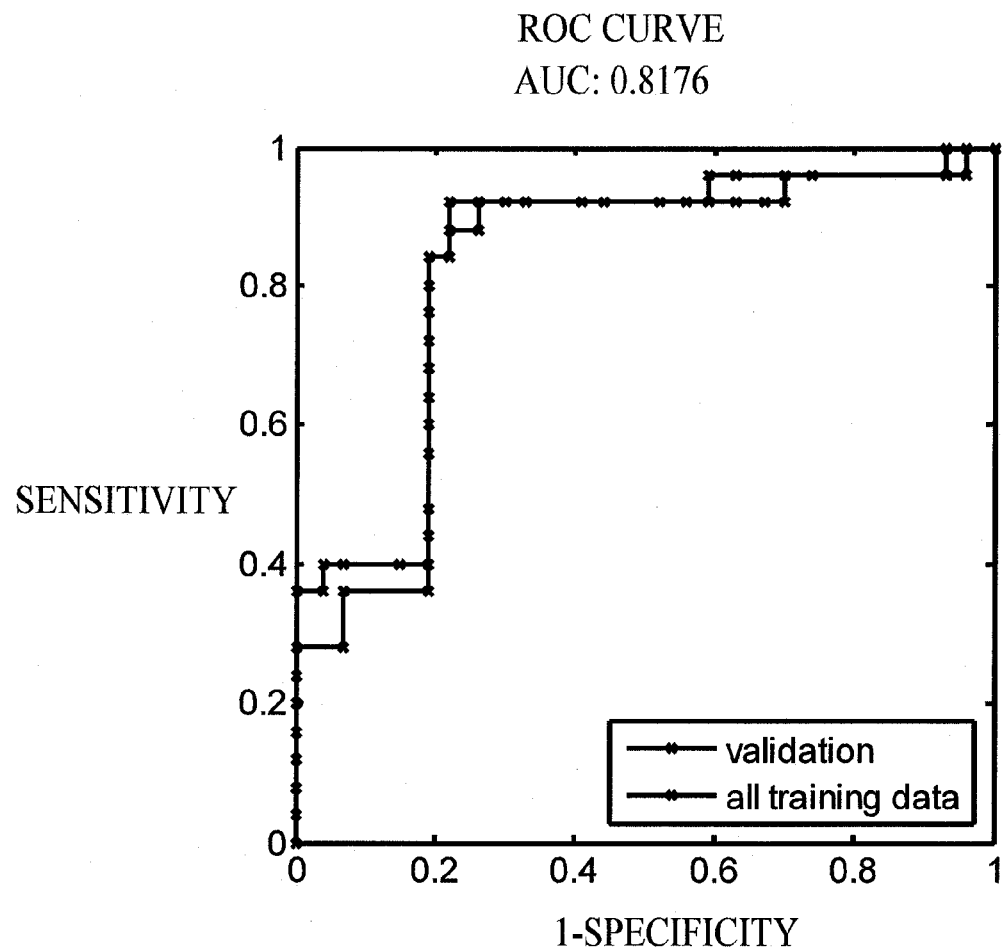

FIG. 3G shows receiver operating characteristic (ROC) curve analysis, including the area under the curve (AUC), of combined use of both the plasma and PBMC samples of breast cancer patients, compared to the subjects with benign breast tumors and healthy controls. Values for sensitivity and specificity are presented in FIG. 3G.

Figure 3H:
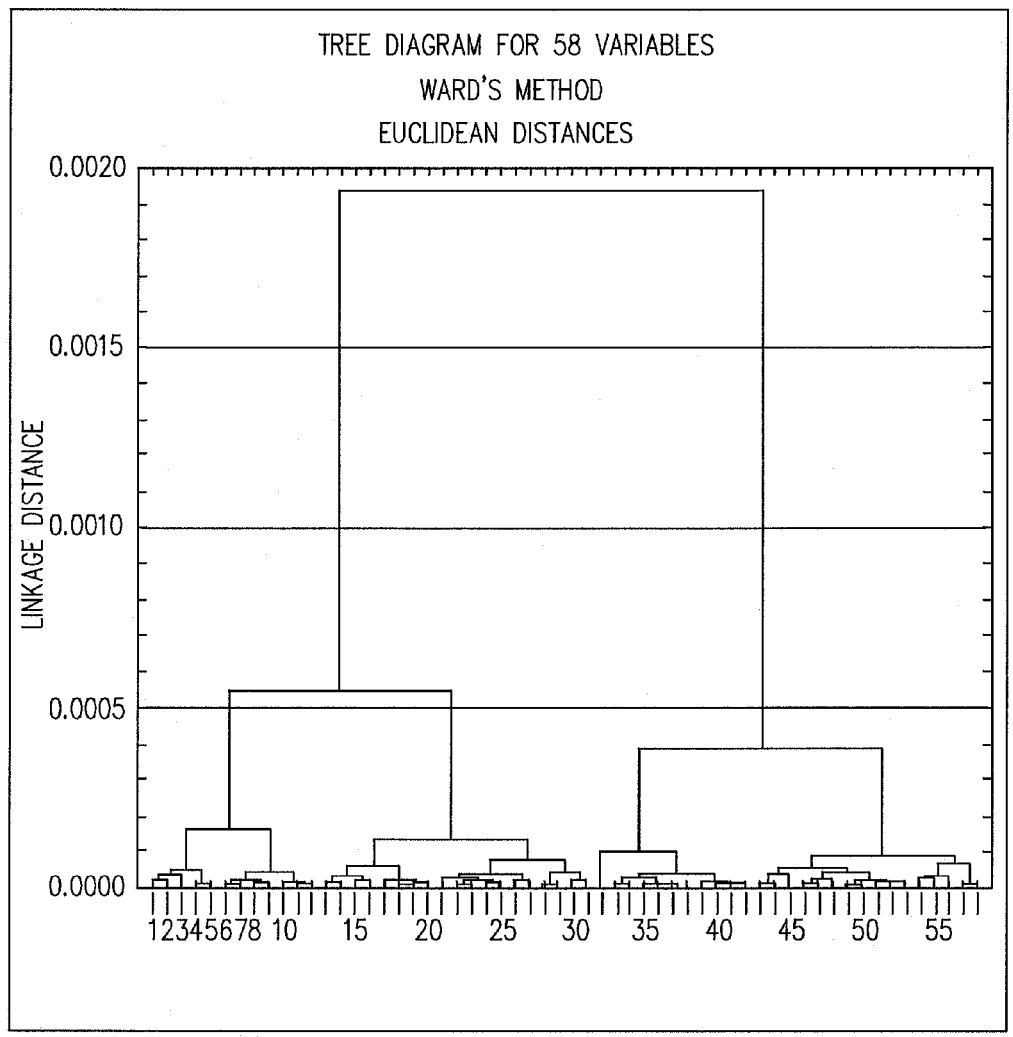

FIG. 3H represents cluster analysis according to Ward's method of breast cancer patients, the subjects with benign breast tumors, and the healthy controls, in accordance with some applications of the present invention. The second derivative data analysis shown in FIGS. 2B-D was used as input for the cluster analysis. FIG. 3H shows a distinction between (a) cancer patients and (b) subjects with benign breast tumors and healthy controls (the benign group and healthy controls showing closer similarity).

Table E2 represents the data corresponding to the numbers in FIG. 3H.

TABLE E2

| 1 | CANCER23 |
|---|---|
| 2 | CANCER22 |
| 3 | CANCER21 |
| 4 | CANCER13 |
| 5 | BEN6 |
| 6 | CANCER17 |
| 7 | CANCER14 |
| 8 | CANCER24 |
| 9 | H6 |
| 10 | CANCER11 |
| 11 | CANCER20 |
| 12 | H5 |
| 13 | CANCER27 |
| 14 | CANCER19 |
| 15 | CANCER25 |
| 16 | CANCER18 |
| 17 | CANCER15 |
| 18 | CANCER6 |
| 19 | BEN7 |
| 20 | BEN5 |
| 21 | CANCER9 |
| 22 | CANCER16 |
| 23 | CANCER5 |

TABLE E2-continued

| 24 | CANCER7 |
|---|---|
| 25 | CANCER1 |
| 26 | CANCER3 |
| 27 | H7 |
| 28 | CANCER12 |
| 29 | CANCER10 |
| 30 | HGDISP |
| 31 | H4 |
| 32 | H14 |
| 33 | BEN8 |
| 34 | H13 |
| 35 | BEN12 |
| 36 | BEN14 |
| 37 | H12 |
| 38 | H10 |
| 39 | H9 |
| 40 | CANCER28 |
| 41 | H11 |
| 42 | H8 |
| 43 | BEN13 |
| 44 | BEN11 |
| 45 | BEN1 |
| 46 | CANCER2 |
| 47 | BEN9 |
| 48 | BEN3 |
| 49 | BEN15 |
| 50 | BEN2 |
| 51 | BEN10 |
| 52 | CANCER8 |
| 53 | H3 |
| 54 | CANCER26 |
| 55 | BEN4 |
| 56 | H2 |
| 57 | CANCER4 |
| 58 | H1 |

Reference is now made to FIGS. 4A-D and Table E3 which include clinical information for 23 breast cancer patients and analysis of PBMC samples (FIGS. 4A-B) and plasma samples (FIGS. 4C-D) obtained from the breast cancer patients in accordance with some applications of the present invention.

Table E3 is a table representing clinical data for 23 female breast cancer patients who took part in the studies described herein. In Table E3:

"Location at main organ" column: "R" represents Right breast and "L" represents Left breast Pathology column: "M" represents Malignant and "U" represents Undetermined Malignancy type column: "IDC" represents Infiltrating Ductal Carcinoma, and "ILC" represents Infiltrating Lobular Carcinoma.

"LN" means lymph node
"MS" means "mass size" (in mm)
"#m" means "number of masses"

TABLE E3

| Age | Location at main Organ | MS | # m | # LN | # Positive LN | Margin | Vascular Invasion | Pathology | Stage T | N | M | S No. | S Sub | Malignancy type |
|---|---|---|---|---|---|---|---|---|---|---|---|---|---|---|
| 39 | L | 20 | 8 | 14 | 2 | R1 | Y | M | 1 | 1 | 0 | 2 | a | IDC |
| 51 | L | 75 | 1 | 3 | 0 | R0 | No | M | 3 | 0 | 0 | 2 | b | ILC |
| 62 | L | 21 | 2 | 4 | 0 | R0 | No | M | 2 | 0 | 0 | 2 | a | IDC |
| 55 | R | 15 | 1 | 9 | 2 | R0 | No | M | 1 | 1 | 0 | 2 | a | IDC |
| 71 | R | 8 | 1 | 3 | 0 | R0 | NA | M | 1 | 0 | 0 | 1 | a | IDC |
| 77 | R | 25 | 1 | 2 | 0 | R0 | NA | M | 2 | 0 | 0 | 2 | a | ILC |
| 68 | L | 20 | 2 | 4 | 0 | R0 | NA | M | 1 | 0 | 0 | 1 | a | Mucinous Carcinoma (Colloid) |
| 69 | L | 18 | 1 | 3 | 0 | R0 | Y | M | 1 | 0 | 0 | 1 | a | IDC |
| 62 | R | 10 | 1 | 6 | 0 | R0 | NA | M | 1 | 0 | 0 | 1 | a | IDC |
| 42 | L | 25 | NA | 21 | 13 | R0 | No | M | 2 | 3 | 0 | 3 | c | IDC + ILC |

TABLE E3-continued

| Age | Location at main Organ | # MS | # m | # Positive LN | # LN | Margin | Vascular Invasion | Pathology | Stage T | N | M | S | S No. | S Sub | Malignancy type |
|---|---|---|---|---|---|---|---|---|---|---|---|---|---|---|---|
| 69 | R | NA | 1 | 8 | 0 | R0 | No | U | | | | | | | Ductal Carcinoma In-Situ (DCIS) |
| 29 | R | 10 | 1 | 3 | 0 | R0 | No | M | 1 | 0 | 0 | | 1 | a | IDC |
| 51 | L | 28 | 1 | 34 | 6 | R0 | Y | M | 2 | 2 | 0 | | 3 | a | IDC |
| 70 | L | 7 | 2 | 5 | 0 | R0 | NA | M | 1 | 0 | 0 | | 1 | a | ILC + Mucinous |
| 57 | L | NR | NR | 11 | 0 | NR | NR | M | 2 | 0 | 0 | | 2 | a | IDC |
| 47 | R | 33 | 1 | 10 | 0 | R0 | Y | M | 2 | 0 | 0 | | 2 | a | IDC |
| 51 | L | 9 | 1 | 4 | 0 | R0 | NA | M | 1 | 0 | 0 | | 1 | a | IDC |
| 60 | L | 45 | 1 | NA | NA | R0 | NA | M | 2 | 0 | 0 | | 2 | a | IDC |
| 67 | R | 13 | 1 | 3 | 0 | R0 | No | M | 1 | 0 | 0 | | 1 | a | IDC |
| 71 | R | 10 | 1 | 9 | 0 | R0 | No | M | 1 | 0 | 0 | | 1 | a | ILC |
| 58 | R | 5 | 1 | 1 | 0 | R0 | NA | M | 1 | 0 | 0 | | 1 | a | ILC |
| 63 | L | 20 | 1 | 9 | 1 | R0 | NA | M | 1 | 1 | 0 | | 2 | a | IDC |
| 66 | R | 18 | 2 | 2 | 0 | R0 | Y | M | 1 | 0 | 0 | | 1 | a | IDC |

Figure 4A:
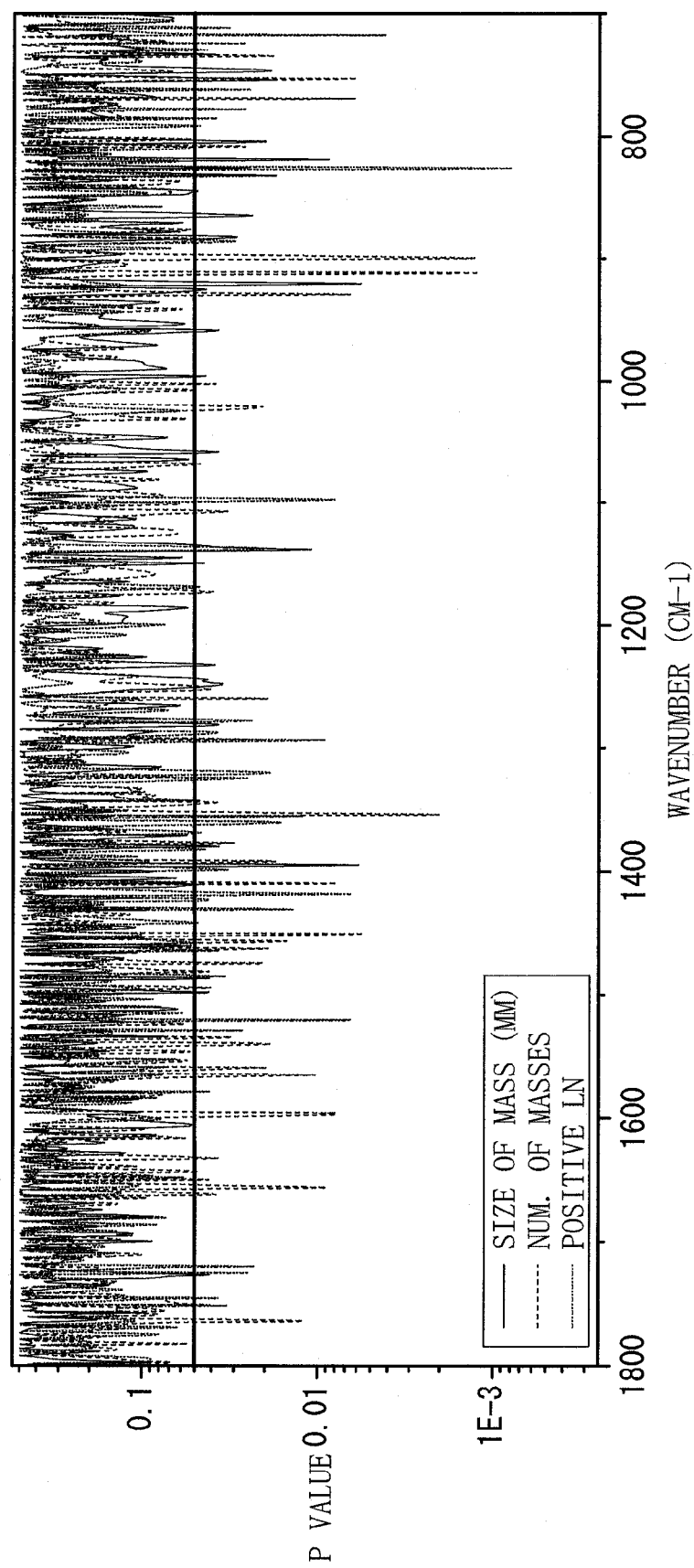
FIGS. 4A-D are graphs representing analysis of clinical information of breast cancer patients, for PBMC samples and plasma samples obtained from the breast cancer patients in accordance with some applications of the present invention.
Figure 4B:
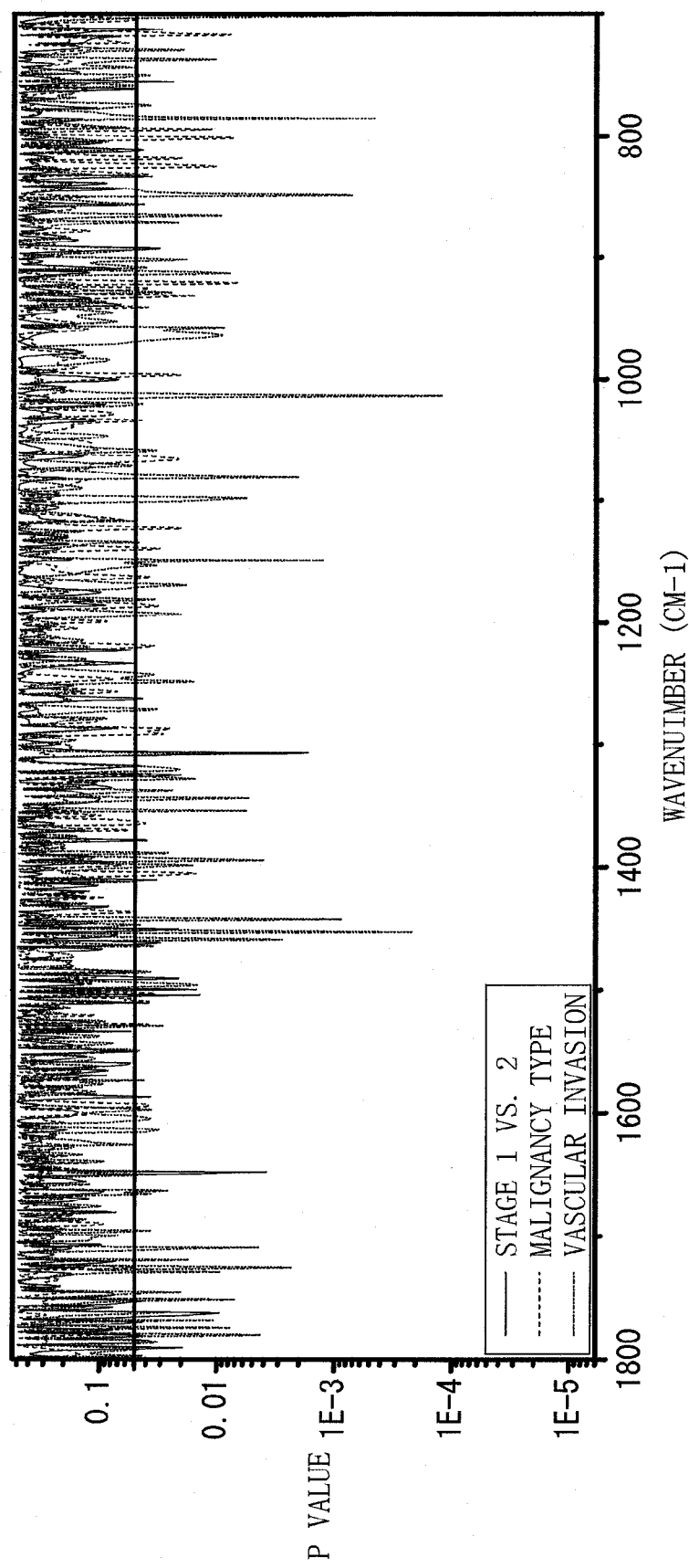

FIGS. 4A-B are graphs representing analysis of various clinical parameters of the breast cancer patients as derived from Table E3. Statistical analysis was performed and P-values are provided. The effect of the following parameters on PBMC from breast cancer patients was assessed: size of the mass, number of masses, positive lymph nodes (LN), malignancy type, vascular invasion and distinguishing between stage 1 and stage 2 of the disease. As shown, in accordance with some applications of the present invention, it is possible to identify a specific pattern for each clinical parameter in the FTIR spectra obtained from PBMC samples.

Table F lists wavenumbers that were identified in the set of experiments as presented in FIGS. 4A-B. Typically, PBMC samples were analyzed by FTIR-MSP techniques using these wavenumbers to identify the effect of the following clinical parameters on PBMC samples from the breast cancer patients: size of the mass, number of masses, positive lymph nodes (LN), malignancy type, vascular invasion and distinguishing between stage 1 and stage 2 of the disease. For some applications, the PBMC samples are analyzed by FTIR-MSP at at least one wavenumber selected from Table F. Alternatively, the PBMC samples are analyzed by FTIR-MSP at at least two or three wavenumbers selected from Table F:

TABLE F

| Malignancy type | Stage | Vascular Invasion | Num. of Positive LN | Num. of Masses | Size of Mass (mm) |
|---|---|---|---|---|---|
| 729.9 | 1353.8 | 717.4 | 712.6 | 717.4 | 734.3 | 746.3 |
| 737.2 | 1393.8 | 794.0 | 810.9 | 761.3 | 752.6 | 753.5 |
| 750.7 | 1398.6 | 801.3 | 892.9 | 777.7 | 769.0 | 803.2 |
| 774.8 | 1441.5 | 817.7 | 1261.2 | 825.9 | 807.5 | 818.2 |
| 785.4 | 1451.7 | 823.9 | 1306.1 | 832.1 | 884.7 | 824.9 |
| 848.0 | 1458.4 | 830.7 | 1317.1 | 885.2 | 899.1 | 831.7 |
| 855.8 | 1484.4 | 920.8 | 1324.9 | 1097.3 | 911.7 | 864.0 |
| 865.4 | 1494.6 | 925.7 | 1377.9 | 1136.3 | 929.0 | 881.3 |
| 870.7 | 1529.3 | 931.4 | 1410.2 | 1168.7 | 1001.8 | 919.9 |
| 892.9 | 1548.6 | 940.6 | 1449.7 | 1277.1 | 1022.1 | 958.4 |
| 902.0 | 1597.3 | 996.1 | 1461.9 | 1286.6 | 1106.9 | 1058.7 |
| 908.3 | 1604.0 | 1033.7 | 1489.7 | 1293.0 | 1172.5 | 1136.3 |
| 912.2 | 1614.6 | 1064.5 | 1499.4 | 1319.6 | 1250.1 | 1231.3 |
| 928.1 | 1649.3 | 1122.9 | 1503.7 | 1324.9 | 1259.3 | 1246.3 |
| 957.5 | 1663.3 | 1139.7 | 1510.0 | 1360.5 | 1292.6 | 1281.0 |
| 963.8 | 1709.6 | 1161.9 | 1549.5 | 1368.7 | 1344.6 | 1394.8 |
| 1012.9 | 1725.5 | 1185.0 | 1648.4 | 1382.2 | 1353.3 |
| 1020.2 | 1729.8 | 1218.8 | 1753.0 | 1397.7 | 1376.9 |
| 1058.7 | 1745.7 | 1288.2 | 1762.6 | 1417.9 | 1392.4 |
| 1080.4 | 1751.5 | 1323.9 | 1769.4 | 1422.7 | 1409.2 |
| 1098.3 | 1762.6 | 1363.4 | 1780.5 | 1430.4 | 1450.2 |
| 1148.9 | 1775.2 | 1405.4 | 1785.3 | 1484.4 | 1456.0 |
| 1152.3 | 1780.5 | 1502.3 | 1791.1 | 1520.6 | 1461.8 |
| 1168.7 | 1785.8 | 1508.5 | | 1725.5 | 1473.8 |
| 1192.3 | | 1593.4 | | 1745.7 | 1534.6 |
| 1241.9 | | | | | 1539.9 |
| 1247.7 | | | | | 1560.1 |
| 1270.4 | | | | | 1565.9 |
| 1307.0 | | | | | 1596.3 |
| 1318.6 | | | | | 1632.0 |
| 1326.3 | | | | | 1654.6 |
| 1337.9 | | | | | 1660.9 |
| 1343.2 | | | | | 1763.1 |

For some applications, one, two, three, or more of the following wavenumbers selected from Table F are used to identify in PBMC samples a distinct spectral pattern caused by the malignancy type of the breast tumor: 785.4±4 cm-1, 848.0±4 cm-1, 1012.9±4 cm-1, 1080.4±4 cm-1, 1148.9±4 cm-1, and 1451.7±4 cm-1.

For some applications, one, two, three, or more of the following wavenumbers selected from Table F are used to distinguish between stage 1 and stage 2 of malignant breast tumors: 717.4±4 cm-1, 801.3±4 cm-1, 823.9±4 cm-1, 920.8±4 cm-1, and 1405.4±4 cm-1.

For some applications, one, two, three, or more of the following wavenumbers selected from Table F are used to identify in PBMC samples a distinct spectral pattern caused by vascular invasion of a breast tumor: 1306.1±4 cm-1, 1489.7±4 cm-1, 1503.7±4 cm-1, 1648.4±4 cm-1, 1762.6±4 cm-1.

For some applications, one, two, three, or more of the following wavenumbers selected from Table F are used to identify in PBMC samples a distinct spectral pattern caused by the number of positive lymph nodes of a breast cancer patient: 717.4±4 cm-1, 825.9±4 cm-1, 1097.3±4 cm-1, 1293.0±4 cm-1, 1417.9±4 cm-1, and 1520.6±4 cm-1.

For some applications, one, two, three, or more of the following wavenumbers selected from Table F are used to identify in PBMC samples a distinct spectral pattern caused by the number of masses of a breast cancer patient: 752.6 cm-1, 769.0±4 cm-1, 899.1±4 cm-1, 911.7±4 cm-1, 1353.3±4 cm-1, and 1450.2±4 cm-1.

For some applications, one, two, three, or more of the following wavenumbers selected from Table F are used to identify in PBMC samples a distinct spectral pattern caused by the size of the mass (mm) of the breast tumor: 746.3 cm-1, 818.2±4 cm-1, 919.9±4 cm-1, 1136.3±4 cm-1, and 1394.8±4 cm-1.

Figure 4C:
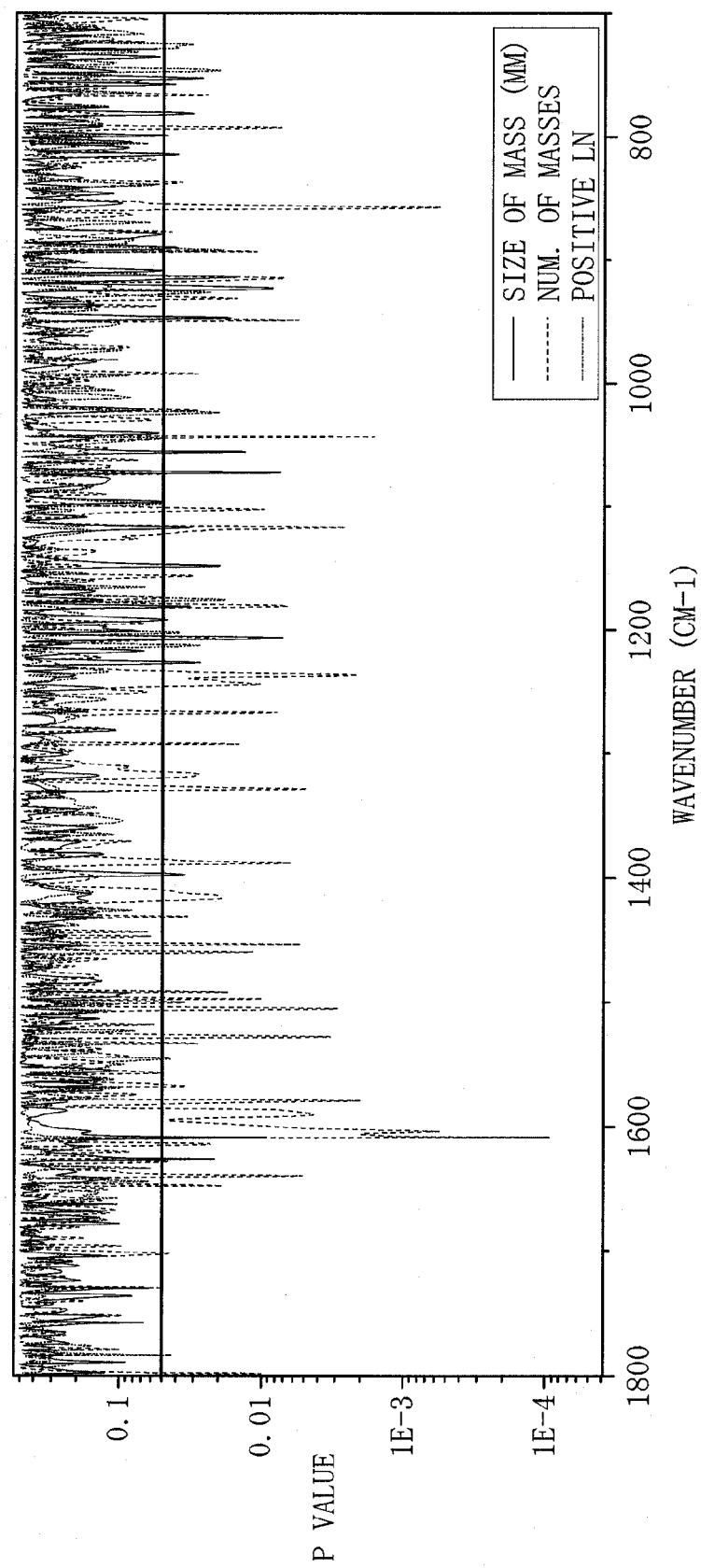
Figure 4D:
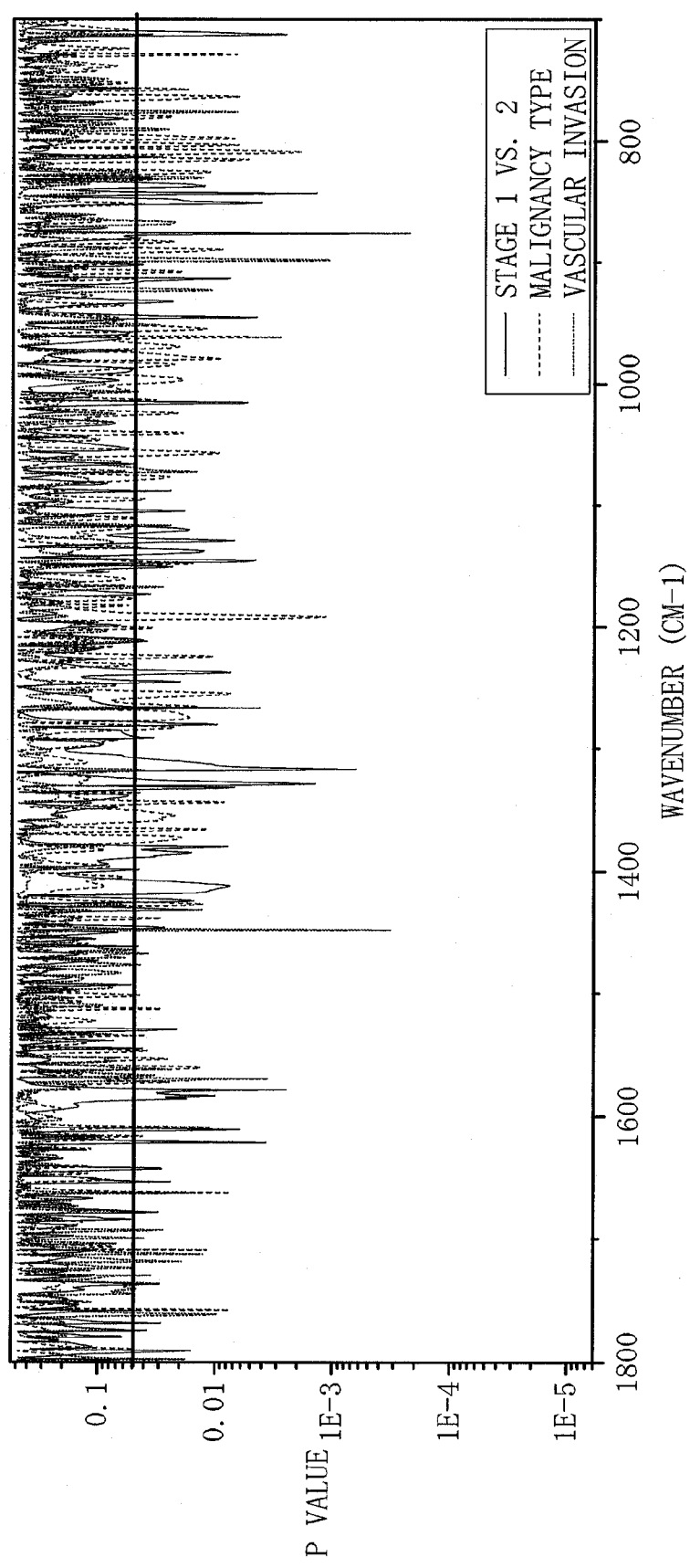

FIGS. 4C-D are graphs representing analysis of various clinical parameters of the breast cancer patients as derived from Table E3. Statistical analysis was performed and P-values are provided. As shown, in accordance with some applications of the present invention, it is possible to identify a distinct spectral pattern in FTIR analysis of plasma samples that is caused in response to at least one of the following parameters: size of the mass, number of masses, positive lymph nodes (LN), malignancy type, vascular invasion and distinguishing between stage 1 and stage 2 of the disease.

Table G lists wavenumbers that were identified in this set of experiments as presented in FIGS. 4C-D. Typically, plasma samples were analyzed by FTIR-MSP techniques using these wavenumbers to identify the following parameters based on plasma samples from the breast cancer patients: size of the mass, number of masses, positive lymph nodes (LN), malignancy type, vascular invasion and distinguishing between stage 1 and stage 2 of the disease. For some applications, the plasma samples are analyzed by FTIR-MSP at at least one wavenumber selected from Table G. Alternatively, the plasma samples are analyzed by FTIR-MSP at at least two or three wavenumbers selected from Table G:

TABLE G

| Malignancy type | Stage | Vascular Invasion | Num. of Positive LN | Num. of Masses | Size of Mass (mm) |
| --- | --- | --- | --- | --- | --- |
| 775.7 | 729.4 | 712.6 | 726.5 | 766.1 | 753.1 |
| 790.7 | 757.9 | 813.3 | 746.3 | 792.1 | 757.9 |
| 830.2 | 763.7 | 836.5 | 892.4 | 837.0 | 781.5 |
| 866.8 | 780.5 | 843.2 | 927.1 | 856.7 | 799.3 |
| 897.7 | 797.9 | 850.9 | 1023.5 | 893.4 | 814.3 |
| 922.8 | 803.2 | 876.5 | 1174.9 | 915.1 | 890.5 |
| 951.2 | 809.0 | 902.0 | 1202.4 | 931.0 | 914.1 |
| 1070.8 | 815.7 | 913.6 | 1212.5 | 949.3 | 922.8 |
| 1116.6 | 825.4 | 932.4 | | 991.7 | 946.9 |
| 1166.7 | 831.7 | 945.4 | | 1021.1 | 1055.8 |
| 1211.6 | 852.9 | 1014.9 | | 1043.3 | 1072.7 |
| 1266.5 | 883.2 | 1089.1 | | 1073.7 | 1117.5 |
| 1317.6 | 889.5 | 1105.0 | | 1102.1 | 1147.9 |
| 1447.3 | 890.0 | 1120.4 | | 1116.6 | 1180.7 |
| 1466.6 | 907.8 | 1129.1 | | 1156.1 | 1206.3 |
| 1561.6 | 954.6 | 1138.3 | | 1173.0 | 1226.0 |
| 1569.3 | 961.8 | 1145.5 | | 1179.7 | 1397.2 |
| 1692.7 | 968.6 | 1150.8 | | 1206.3 | 1608.8 |
| 1699.5 | 979.2 | 1173.0 | | 1235.7 | 1626.2 |
| 1712.0 | 985.0 | 1211.1 | | 1266.5 | |
| 1717.8 | 997.0 | 1237.6 | | 1292.1 | |
| 1736.6 | 1012.9 | 1244.8 | | 1317.1 | |
| 1740.9 | 1024.0 | 1266.5 | | 1328.2 | |
| 1761.2 | 1040.4 | 1280.5 | | 1387.5 | |
| | 1057.8 | 1291.1 | | 1414.0 | |
| | 1077.5 | 1316.2 | | 1430.9 | |
| | 1095.4 | 1328.2 | | 1453.1 | |
| | 1110.8 | 1332.6 | | 1459.4 | |
| | 1134.9 | 1380.3 | | 1491.7 | |
| | 1147.0 | 1412.1 | | 1497.0 | |
| | 1190.8 | 1424.2 | | 1499.9 | |
| | 1201.0 | 1430.9 | | 1504.7 | |

TABLE G-continued

| Malignancy type | Stage | Vascular Invasion | Num. of Positive LN | Num. of Masses | Size of Mass (mm) |
| --- | --- | --- | --- | --- | --- |
| | 1224.1 | 1445.9 | | 1527.3 | |
| | 1255.0 | 1529.8 | | 1567.4 | |
| | 1264.6 | 1578.9 | | 1579.4 | |
| | 1271.8 | 1611.2 | | 1589.1 | |
| | 1282.9 | 1621.4 | | 1608.3 | |
| | 1344.1 | 1642.6 | | 1613.6 | |
| | 1355.2 | 1653.2 | | 1639.2 | |
| | 1366.3 | 1678.2 | | | |
| | 1373.6 | 1737.1 | | | |
| | 1427.1 | | | | |
| | 1438.6 | | | | |
| | 1512.9 | | | | |
| | 1546.6 | | | | |
| | 1553.9 | | | | |
| | 1560.6 | | | | |
| | 1572.7 | | | | |
| | 1609.3 | | | | |
| | 1616.5 | | | | |
| | 1662.3 | | | | |

For some applications, one, two, three, or more of the following wavenumbers selected from Table G are used to identify in plasma samples a distinct spectral pattern caused by a malignancy type of the breast tumor: 775.7±4 cm-1, 897.7±4 cm-1, 922.8±4 cm-1, 1070.8±4 cm-1, 1447.3±4 cm-1, and 1569.3±4 cm-1.

For some applications, one, two, three, or more of the following wavenumbers selected from Table G are used to distinguish between stage 1 and stage 2 of malignant breast tumors: 763.7±4 cm-1, 809.0±4 cm-1, 889.5±4 cm-1, 961.8±4 cm-1, 1255.0±4 cm-1, and 1190.8±4 cm-1.

For some applications, one, two, three, or more of the following wavenumbers selected from Table G are used to identify in plasma samples a distinct spectral pattern caused by vascular invasion of a breast tumor: 843.2±4 cm-1, 876.5±4 cm-1, 1145.5±4 cm-1, 1316.2±4 cm-1, 1328.2±4 cm-1, 1412.1±4 cm-1, and 1578.9±4 cm-1.

For some applications, one, two, three, or more of the following wavenumbers selected from Table G are used to identify in plasma samples a distinct spectral pattern caused by the number of positive lymph nodes of a breast cancer patient: 746.3±4 cm-1, 892.4±4 cm-1, 927.1±4 cm-1, 1023.5±4 cm-1, and 1174.9±4 cm-1.

For some applications, one, two, three, or more of the following wavenumbers selected from Table G are used to identify in plasma samples a distinct spectral pattern caused by the number of masses of a breast cancer patient: 856.7 cm-1, 1043.3±4 cm-1, 1116.6±4 cm-1, 1235.7±4 cm-1, 1387.5±4 cm-1, 1504.7±4 cm-1, and 1608.3±4 cm-1.

For some applications, one, two, three, or more of the following wavenumbers selected from Table G are used to identify in plasma samples a distinct spectral pattern caused by the size of the mass (mm) of the breast tumor: 781.5 cm-1, 922.8±4 cm-1, 946.9±4 cm-1, 1072.7±4 cm-1, 1147.9±4 cm-1 and 1206.3±4 cm-1.

Example 3

In a set of experiments, differential diagnosis of benign gastrointestinal (specifically colorectal) tumors and malignant and pre-malignant gastrointestinal tumors was performed based on a FTIR-MSP spectral pattern at a range of wavenumbers of PBMC samples.

In accordance with applications of the present invention, PBMC samples from 15 healthy controls were analyzed by FTIR-MSP, and a typical FTIR-MSP spectral pattern was established for control PBMC. Additionally, PBMC samples from 36 colorectal cancer patients were subjected to FTIR-MSP analysis and compared to the control FTIR-MSP spectral pattern. Additionally, PBMC samples from 14 subjects with a benign tumor in colorectal tissue were subjected to FTIR-MSP analysis and compared to the control FTIR-MSP spectral pattern and to the colorectal cancer FTIR-MSP spectral pattern. The PBMC samples were obtained by preliminary processing of the peripheral blood in accordance with the protocols described hereinabove with reference to extraction of peripheral blood mononuclear cells (PBMC). The PBMC samples were then analyzed by FTIR-MSP, in accordance with the protocols described hereinabove with reference to FTIR-MSP.

For the purpose of the gastrointestinal set of experiments, the 36 colorectal cancer patients included patients with pre-malignant conditions, typically, high-grade dysplasia. As shown hereinbelow, some applications of the present invention allow distinguishing between patients with a gastrointestinal pre-malignant condition (e.g., a tumor exhibiting high dysplasia) and patients with a malignant tumor in gastrointestinal tissue.

Reference is made to FIGS. 5A-D, which are graphs representing FTIR absorption spectra and the second derivative of the absorption spectra and analysis thereof, for PBMC samples from 36 colorectal cancer patients, 14 subjects with benign colorectal tumors and 15 healthy controls, derived in accordance with some applications of the present invention.

Figure 5A:
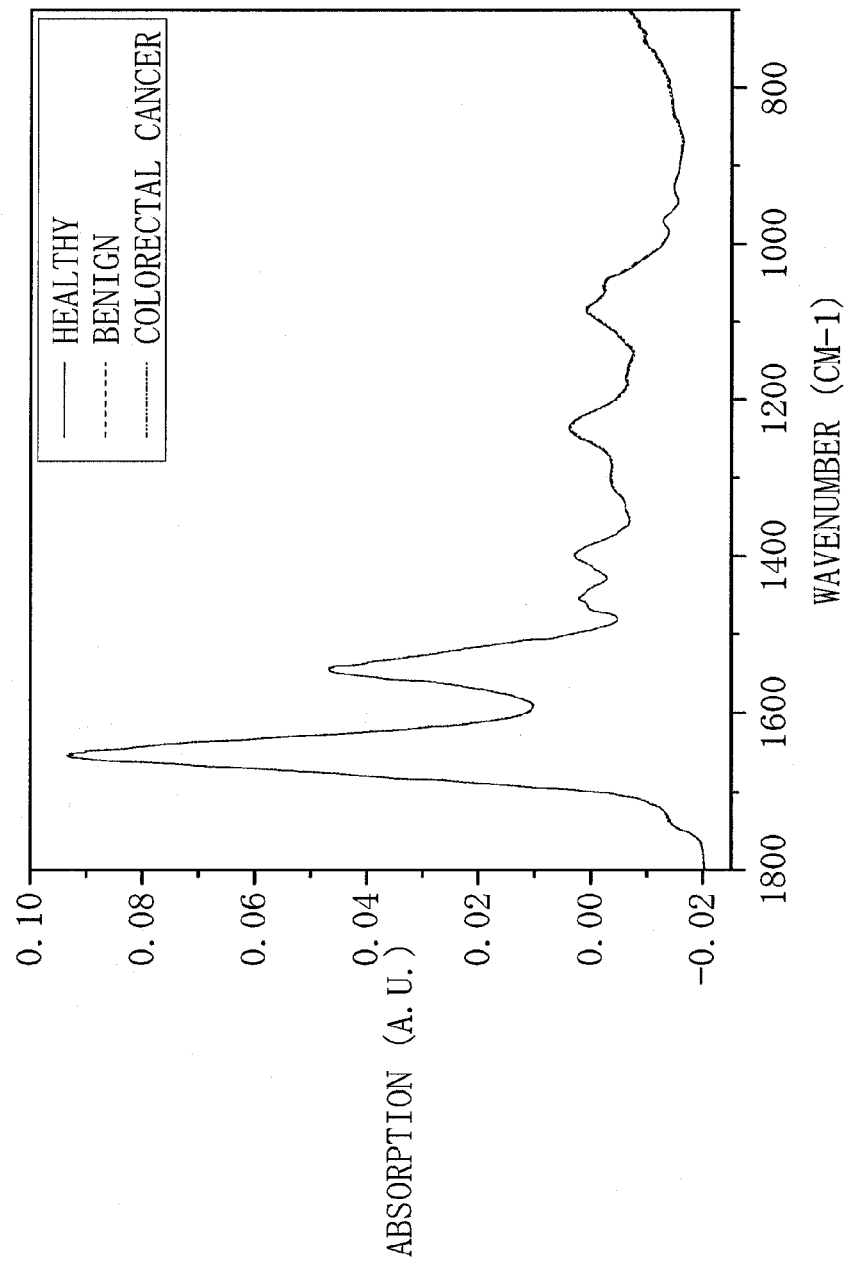
FIGS. 5A-D are graphs representing FTIR absorption spectra, the second derivative of the absorption spectra, and analysis thereof, based on PBMC samples from colorectal cancer patients, subjects with benign colorectal tumors, and controls, derived in accordance with some applications of the present invention.

FIG. 5A shows average FTIR-MSP absorption spectra of PBMC samples of healthy controls, subjects with benign colorectal tumors and gastrointestinal cancer patients in the regions of 700-1800 cm-1, after baseline correction and vector normalization. Each spectrum represents the average of five measurements at different sites for each sample. The spectra are composed of several absorption bands, each corresponding to specific functional groups of specific macromolecules such as lipids, proteins, and carbohydrates and nucleic acids. Generally, the FTIR spectrum is typically analyzed by tracking changes in absorption (intensity and/or shift) of these macromolecules.

Figure 5B:
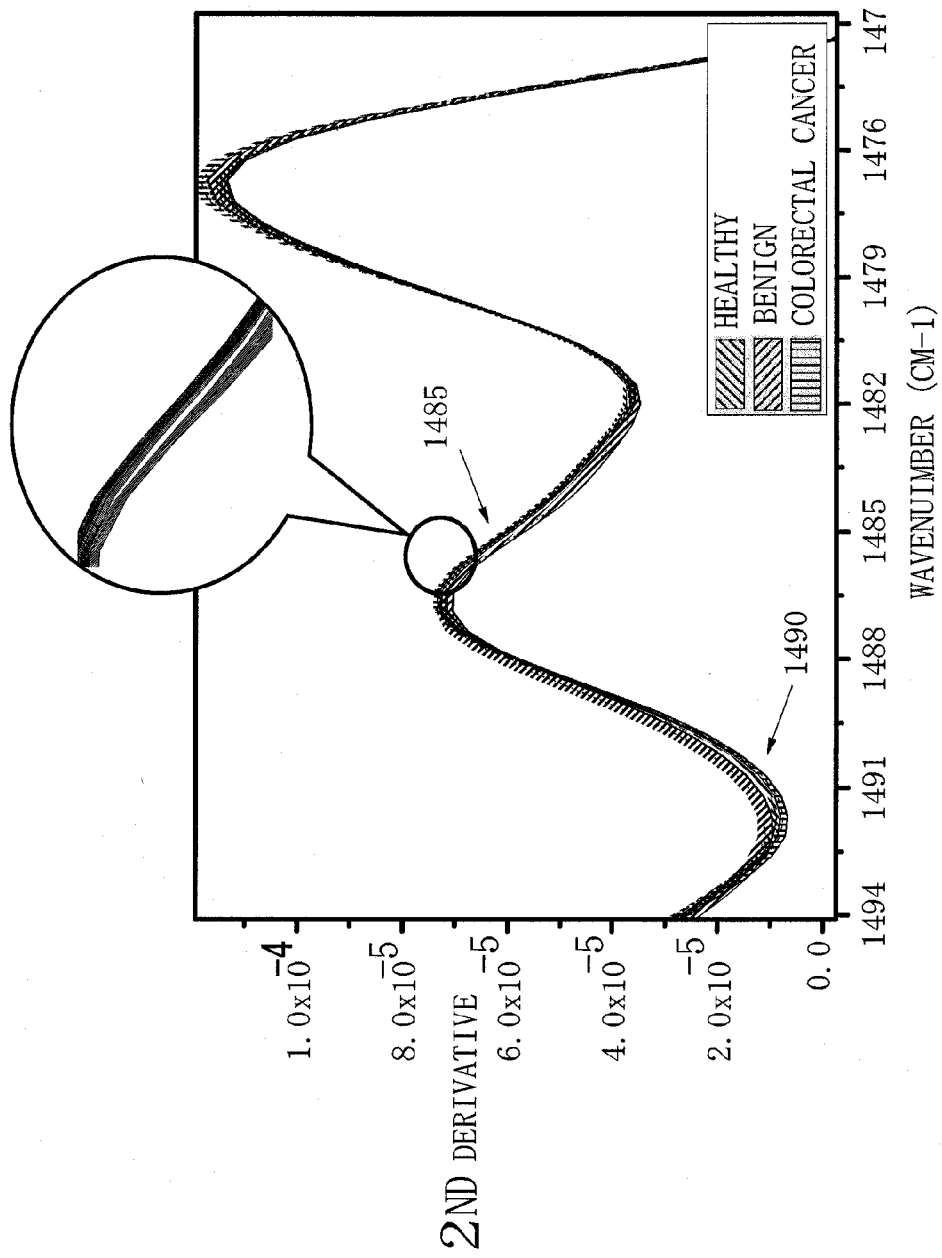

Reference is made to FIG. 5B. In order to achieve effective comparison between the PBMC samples of the colorectal cancer patients, subjects with benign colorectal tumors and the controls, the second derivative of the baseline-corrected, vector-normalized FTIR-MSP spectra was used. Results are presented in FIG. 5B. As shown from the second derivative spectra analysis, the PBMC samples from the subjects with a benign tumor differed significantly from the spectra of PBMC samples from both the subjects with malignant tumors and the controls, in the spectral region of 1485 cm-1 and 1490 cm-1.

The mean±SEM for each of the data sets (healthy, benign, colorectal cancer) is represented by the thickness of the graph lines representing the healthy, benign, and colorectal cancer groups, in accordance with the figure legend, as shown in FIG. 5B.

Figure 5C:
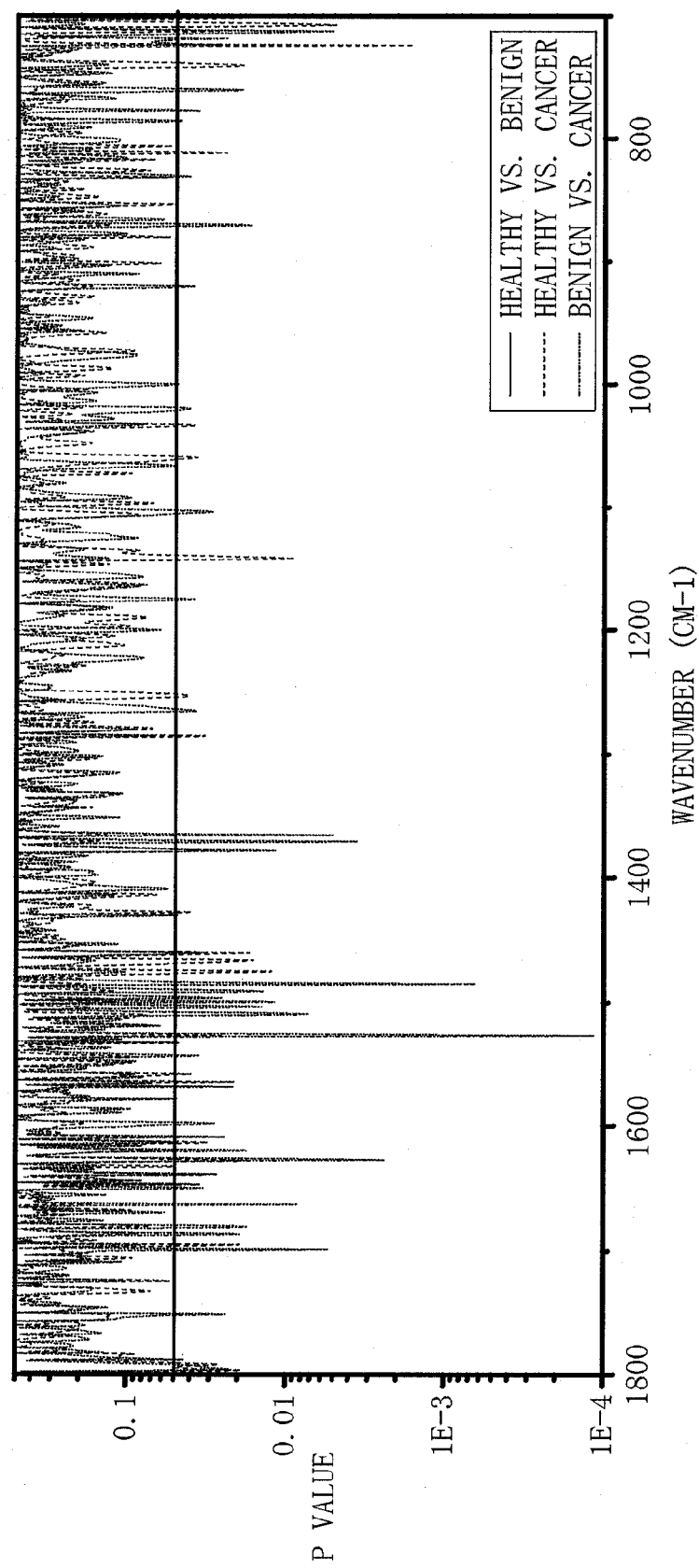
Figure 5D:
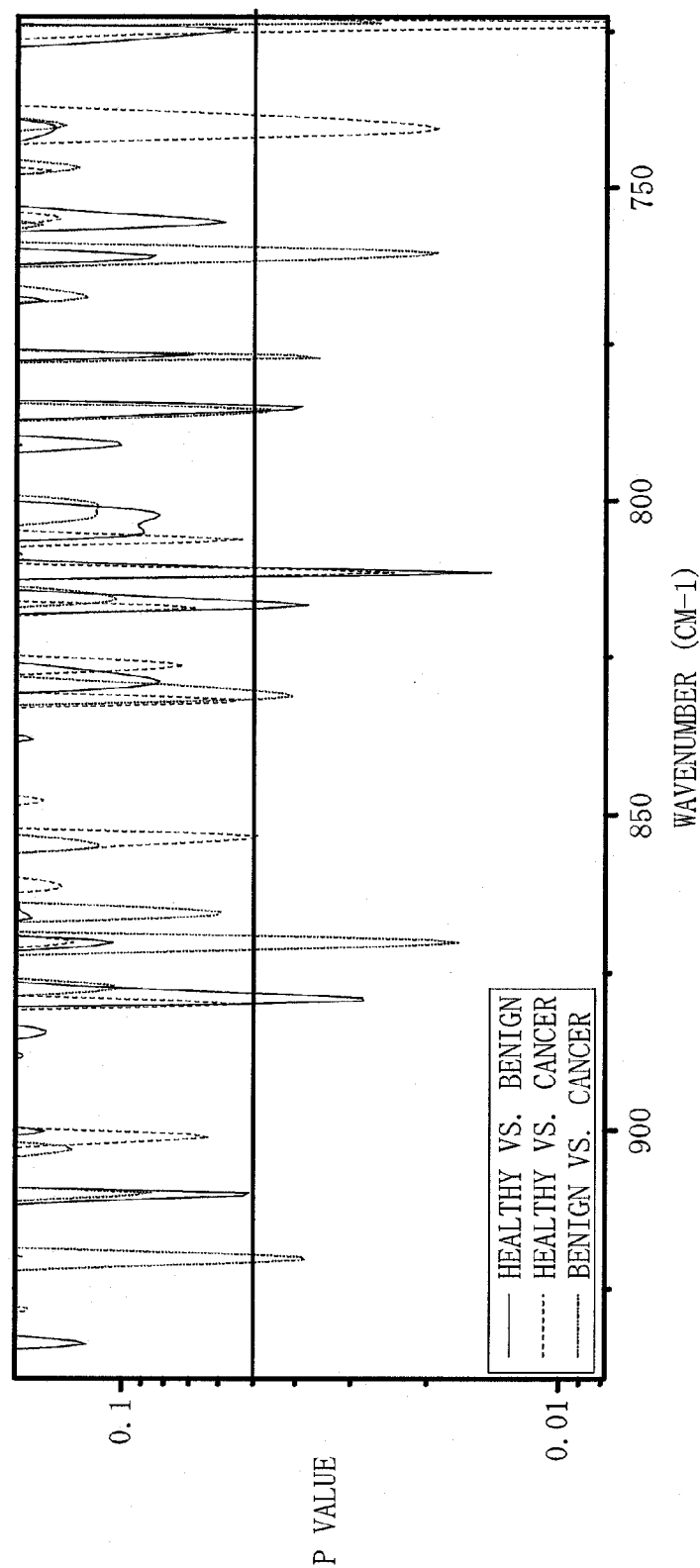

Reference is made to FIGS. 5C-D, which are graphs representing values of the second derivative of absorption spectra of PBMC samples from subjects with benign colorectal tumors compared to PBMC samples from cancer patients and/or to PBMC samples from healthy controls, derived in accordance with some applications of the present invention. Statistical analysis was performed and P-values are provided. As shown:

a) The second derivative of the FTIR-MSP spectra of PBMC samples from the colorectal cancer patients differed significantly from the second derivative of FTIR-MSP spectra from PBMC of healthy controls;

b) The second derivative of the FTIR-MSP spectra of PBMC samples from the colorectal cancer patients differed significantly from the second derivative of FTIR-MSP spectra from PBMC of subjects with a benign colorectal tumor; and c) The second derivative of the FTIR-MSP spectra of PBMC samples from the subjects with a benign colorectal tumor differed significantly from the second derivative of FTIR-MSP spectra from PBMC of healthy controls.

Table H lists wavenumbers that were used in this set of experiments as presented in FIGS. 5A-D. Typically, PBMC samples were analyzed by FTIR-MSP techniques using these wavenumbers to distinguish between: a) control and colorectal cancer patients; b) control and subjects with benign colorectal tumors; and c) colorectal cancer patients and subjects with benign colorectal tumors. For some applications, the PBMC samples are analyzed by FTIR-MSP at at least one wavenumber selected from Table H. Alternatively, the PBMC samples are analyzed by FTIR-MSP at at least two or three wavenumbers selected from Table H.

TABLE H

| Healthy control vs. Benign Wavenumber (cm-1 ± 4) | Healthy control vs. Cancer Wavenumber (cm-1 ± 4) | | Benign vs. Cancer Wavenumber (cm-1 ± 4) | | | |
|---|---|---|---|---|---|---|
| 707.3 | 707.3 | 1428.0 | 712.6 | 1175.4 | 1509.5 | 1680.7 |
| 785.4 | 724.1 | 1460.8 | 724.1 | 1265.1 | 1526.9 | 1699.0 |
| 811.9 | 741.0 | 1475.3 | 760.8 | 1365.8 | 1543.7 | 1751.5 |
| 879.9 | 811.9 | 1526.9 | 785.9 | 1371.1 | 1569.3 | 1795.9 |
| 1253.0 | 1033.7 | 1565.0 | 831.7 | 1378.4 | 1608.8 | |
| 1485.4 | 1060.2 | 1613.6 | 870.7 | 1430.9 | 1619.9 | |
| 1509.0 | 1141.7 | 1627.6 | 920.8 | 1460.3 | 1627.1 | |
| 1526.9 | 1253.0 | 1638.7 | 999.9 | 1485.9 | 1638.7 | |
| 1662.8 | 1285.3 | 1695.6 | 1020.2 | 1491.2 | 1649.8 | |
| | 1378.4 | 1796.8 | 1104.0 | 1499.9 | 1662.8 | |

For some applications, one, two, three, or more of the following wavenumbers selected from Table H are used to differentiate between the absence of a tumor and a benign colorectal tumor: 785.4±4 cm-1, 811.9±4 cm-1, 879.9±4 cm-1, 1253.0±4 cm-1, 1485.4±4 cm-1, and 1526.9±4 cm-1.

For some applications, one, two, three, or more of the following wavenumbers selected from Table H are used to differentiate between the absence of a tumor and a malignant colorectal tumor: 724.1±4 cm-1, 741.0±4 cm-1, 1141.7±4 cm-1, 1475.3±4 cm-1, 1627.6±4 cm-1, 1695.6±4 cm-1.

For some applications, one, two, three, or more of the following wavenumbers selected from Table H are used to differentiate between a malignant colorectal tumor and a benign colorectal tumor: 760.8±4 cm-1, 870.7±4 cm-1, 1371.1±4 cm-1, 1485.9±4 cm-1, 1526.9±4 cm-1, 1627.1±4 cm-1.

Example 4

In a set of experiments, differential diagnosis of benign gastrointestinal (specifically colorectal) tumors and malignant and pre-malignant gastrointestinal tumors was performed based on a FTIR-MSP spectral pattern at selected wavenumbers of plasma samples.

In accordance with applications of the present invention, plasma samples from 15 healthy controls were analyzed by FTIR-MSP, and a typical FTIR-MSP spectral pattern was established for control plasma. Additionally, plasma samples from 36 colorectal cancer patients were subjected to FTIR-MSP analysis and compared to the control FTIR-MSP spectral pattern. Additionally, plasma samples from 14 subjects with a benign tumor in colorectal tissue were subjected to FTIR-MSP analysis and compared to the control FTIR-MSP spectral pattern and to the colorectal cancer FTIR-MSP spectral pattern. The plasma samples were obtained by preliminary processing of the peripheral blood in accordance with the protocols described hereinabove with reference to isolation of plasma from peripheral blood samples. The plasma samples were then analyzed by FTIR-MSP, in accordance with the protocols described hereinabove with reference to FTIR-MSP.

Reference is made to FIGS. 6A-E, which are graphs representing FTIR absorption spectra and the second derivative of the absorption spectra and analysis thereof, for plasma samples from 36 colorectal cancer patients, 14 subjects with benign colorectal tumors and 15 healthy controls, derived in accordance with some applications of the present invention.

Figure 6A:
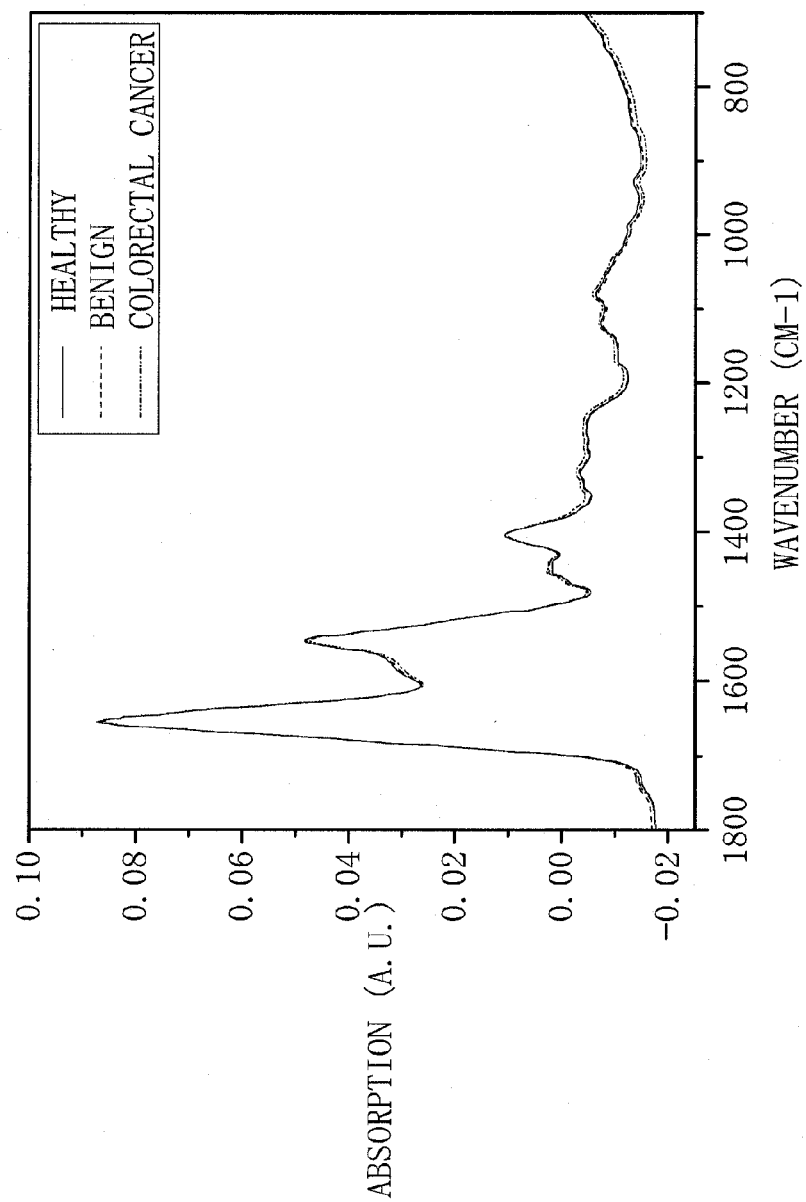
FIGS. 6A-E are graphs representing FTIR absorption spectra, the second derivative of the absorption spectra, and analysis thereof, based on plasma samples from colorectal cancer patients, subjects with benign colorectal tumors, and controls, derived in accordance with some applications of the present invention.

FIG. 6A shows average FTIR-MSP absorption spectra of plasma samples of healthy controls, subjects with benign colorectal tumors and colorectal cancer patients in the regions of 700-1800 cm-1, after baseline correction and vector normalization. Each spectrum represents the average of five measurements at different sites for each sample. The spectra are composed of several absorption bands, each corresponding to specific functional groups of specific macromolecules such as lipids, proteins, and carbohydrates and nucleic acids. Generally, the FTIR spectrum is typically analyzed by tracking changes in absorption (intensity and/or shift) of these macromolecules.

Figure 6B:
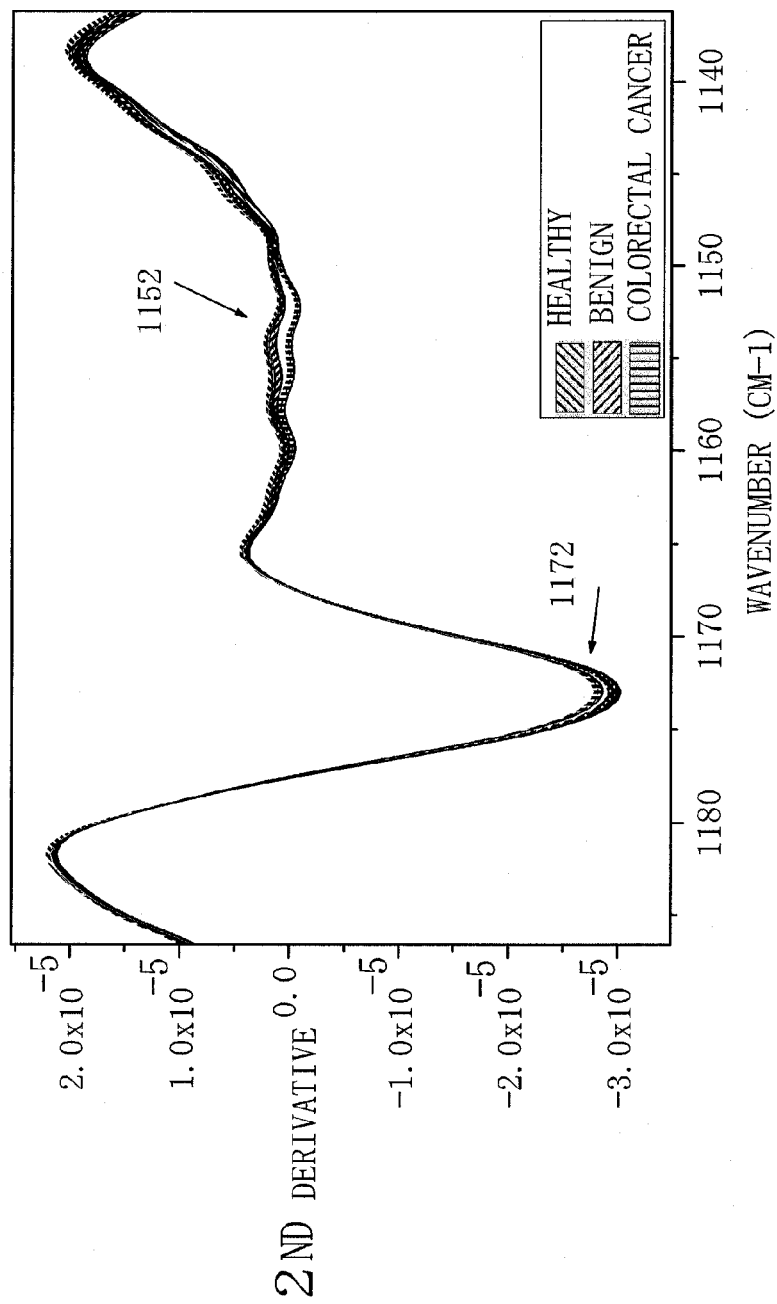
Figure 6C:
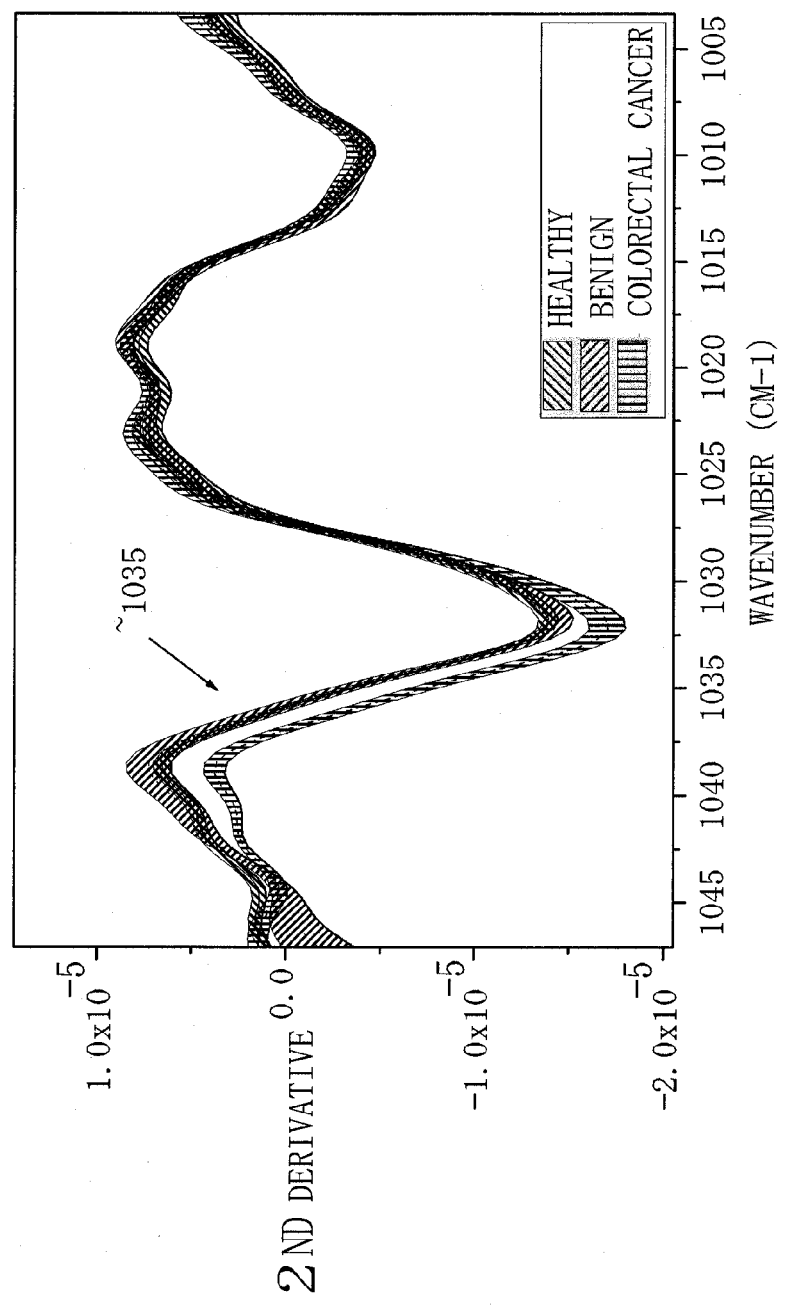

Reference is made to FIGS. 6B-C. In order to achieve effective comparison between the plasma samples of the colorectal cancer patients, subjects with benign colorectal tumors and the controls, the second derivative of the baseline-corrected, vector-normalized FTIR-MSP spectra was used. Results are presented in FIGS. 6B-C. As shown from the second derivative spectra analysis, the plasma samples from the colorectal cancer patients differed significantly from the spectra of plasma samples from both the subjects with benign colorectal tumors and the controls, in the spectral region of 1152 cm-1, 1172 cm-1, and 1035 cm-1.

The mean±SEM for each of the data sets (healthy, benign, colorectal cancer) is represented by the thickness of the graph lines representing the healthy, benign, and colorectal cancer groups, in accordance with the figure legend, as shown in FIG. 6B.

Figure 6D:
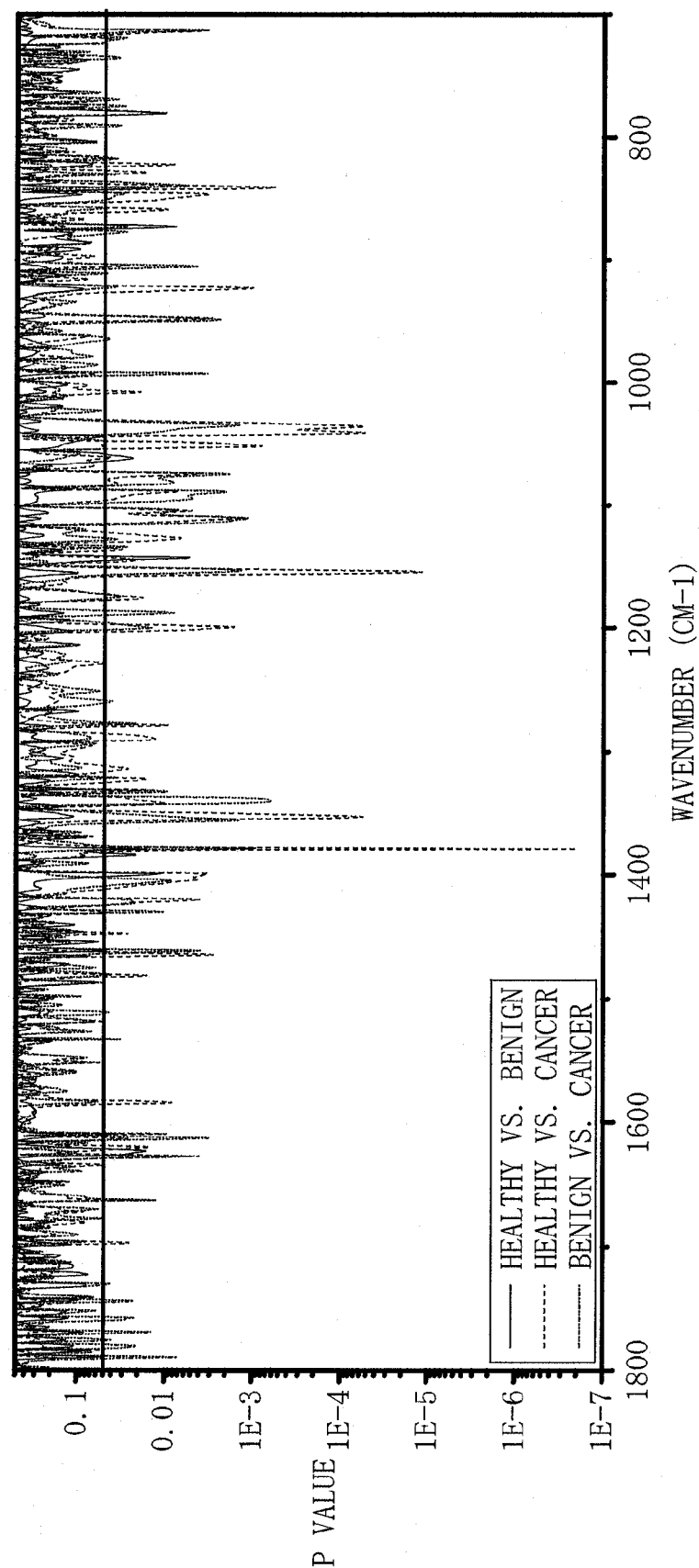
Figure 6E:
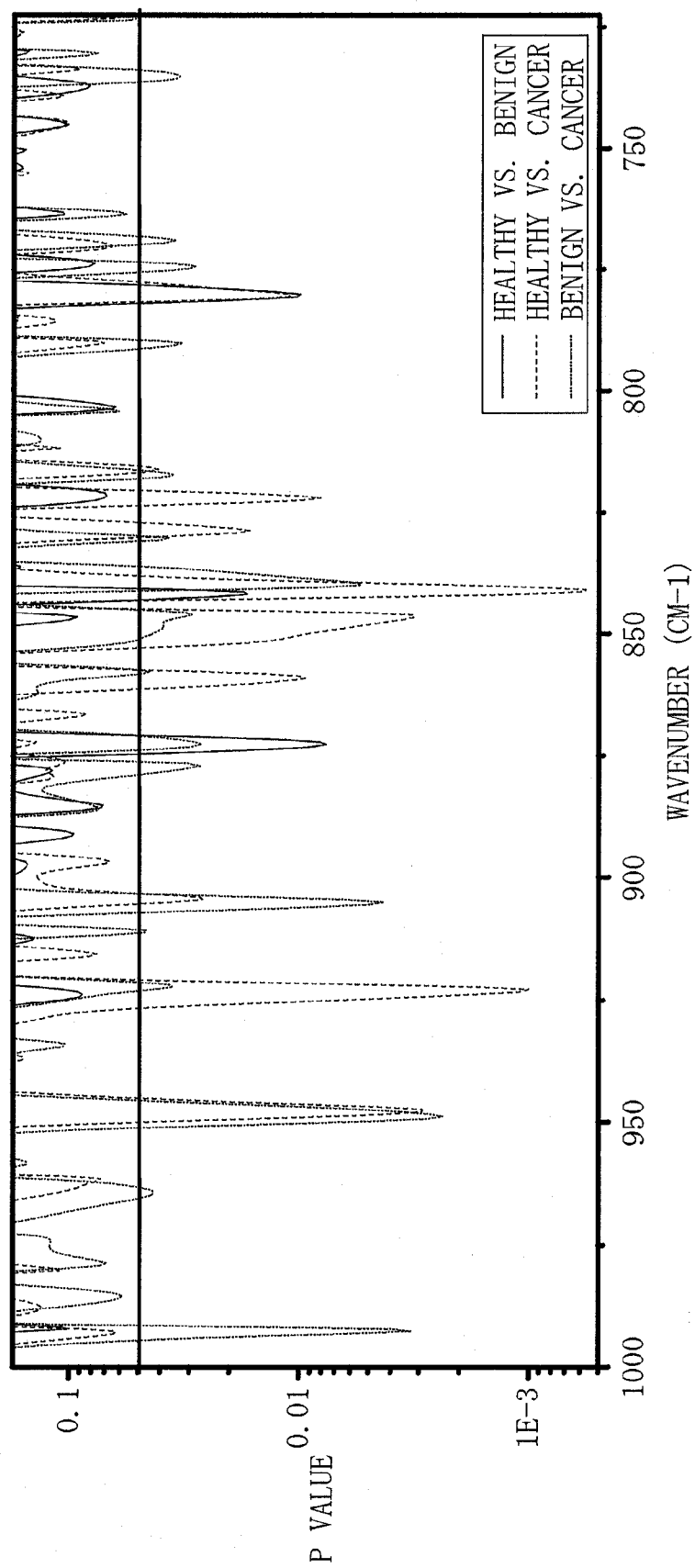

Reference is made to FIGS. 6D-E, which are graphs representing values of the second derivative of absorption spectra of plasma samples from subjects with benign colorectal tumors compared to plasma samples from colorectal cancer patients and/or to plasma samples from healthy controls, derived in accordance with some applications of the present invention. Statistical analysis was performed and P-values are provided. As shown:

a) The second derivative of FTIR-MSP spectra of plasma samples from the gastrointestinal cancer patients differed significantly from the second derivative of FTIR-MSP spectra from plasma of healthy controls;

b) The second derivative of FTIR-MSP spectra of plasma samples from the colorectal cancer patients differed significantly from the second derivative of FTIR-MSP spectra from plasma of subjects with a benign colorectal tumor; and c) The second derivative of FTIR-MSP spectra of plasma samples from the subjects with a benign colorectal tumor differed significantly from the second derivative of FTIR-MSP spectra from plasma of healthy controls.

Table I lists wavenumbers that were used in this set of experiments as presented in FIGS. 6A-E. Typically, plasma samples were analyzed by FTIR-MSP techniques using these wavenumbers to distinguish between: a) control and colorectal cancer patients; b) control and subjects with benign colorectal tumors; and c) colorectal cancer patients and subjects with benign colorectal tumors. For some applications, the PBMC samples are analyzed by FTIR-MSP at at least one wavenumber selected from Table I. Alternatively, the plasma samples are analyzed by FTIR-MSP at at least two or three wavenumbers selected from Table I.

TABLE I

| Healthy control vs. Benign Wavenumber (cm-1 ± 4) | Healthy control vs. Cancer Wavenumber (cm-1 ± 4) | | | Benign vs. Cancer Wavenumber (cm-1 ± 4) | | |
|---|---|---|---|---|---|---|
| 780.1 | 713.5 | 1074.6 | 1342.2 | 713.1 | 1053.4 | 1404.9 |
| 841.3 | 720.8 | 1088.6 | 1352.8 | 718.8 | 1075.6 | 1420.8 |
| 872.6 | 780.1 | 1104.5 | 1378.9 | 735.2 | 1080.9 | 1430.0 |
| 1043.8 | 816.2 | 1109.8 | 1399.1 | 774.3 | 1089.1 | 1460.8 |
| 1061.1 | 822.0 | 1126.2 | 1419.8 | 790.2 | 1104.0 | 1480.1 |
| 1142.1 | 829.2 | 1135.9 | 1430.4 | 817.2 | 1110.3 | 1510.5 |
| 1378.9 | 840.8 | 1144.5 | 1447.3 | 830.2 | 1127.2 | 1612.7 |
| 1383.2 | 846.6 | 1154.7 | 1464.2 | 839.8 | 1133.9 | 1627.1 |
| 1399.6 | 859.1 | 1175.4 | 1481.1 | 846.1 | 1153.2 | 1662.3 |
| 1622.8 | 904.5 | 1199.0 | 1584.2 | 872.1 | 1174.0 | 1729.8 |
|  | 922.8 | 1228.0 | 1609.3 | 877.5 | 1187.5 | 1744.3 |
|  | 947.4 | 1278.6 | 1613.2 | 904.9 | 1200.0 | 1757.8 |
|  | 1007.6 | 1289.2 | 1620.4 | 921.8 | 1277.1 | 1768.9 |
|  | 1035.6 | 1313.3 | 1626.7 | 948.3 | 1321.0 | 1775.6 |
|  | 1052.0 | 1322.9 | 1662.3 | 964.2 | 1332.1 | 1780.9 |
|  | 1061.6 | 1331.1 | 1697.1 | 992.7 | 1340.3 | 1789.6 |
|  |  |  |  | 1034.6 | 1355.2 |  |
|  |  |  |  | 1049.1 | 1378.4 |  |

For some applications, one, two, three, or more of the following wavenumbers selected from Table I are used to differentiate between the absence of a tumor and a benign colorectal tumor: 780.1±4 cm-1, 872.6±4 cm-1, 1142.1±4 cm-1, 1378.9±4 cm-1, 1399.6±4 cm-1, and 1622.8±4 cm-1.

For some applications, one, two, three, or more of the following wavenumbers selected from Table I are used to differentiate between the absence of a tumor and a malignant colorectal tumor: 840.8±4 cm-1, 922.8±4 cm-1, 1035.6±4 cm-1, 1154.7±4 cm-1, 1352.8±4 cm-1, 1378.9±4 cm-1.

For some applications, one, two, three, or more of the following wavenumbers selected from Table I are used to differentiate between a malignant colorectal tumor and a benign colorectal tumor: 948.3±4 cm-1, 1034.6±4 cm-1, 1110.3±4 cm-1, 1153.2±4 cm-1, 1340.3±4 cm-1, 1378.4±4 cm-1.

Reference is now made to FIGS. 5A-D, FIGS. 6A-E and FIGS. 7A-F. FIGS. 7A-F are graphs representing statistical analysis including receiver operating characteristic (ROC) curve analysis of the FTIR absorption spectra, based on PBMC and plasma samples from colorectal cancer patients, subjects with benign colorectal tumors, and controls, as shown in FIGS. 5A-D, and FIGS. 6A-E.

Figure 7A:
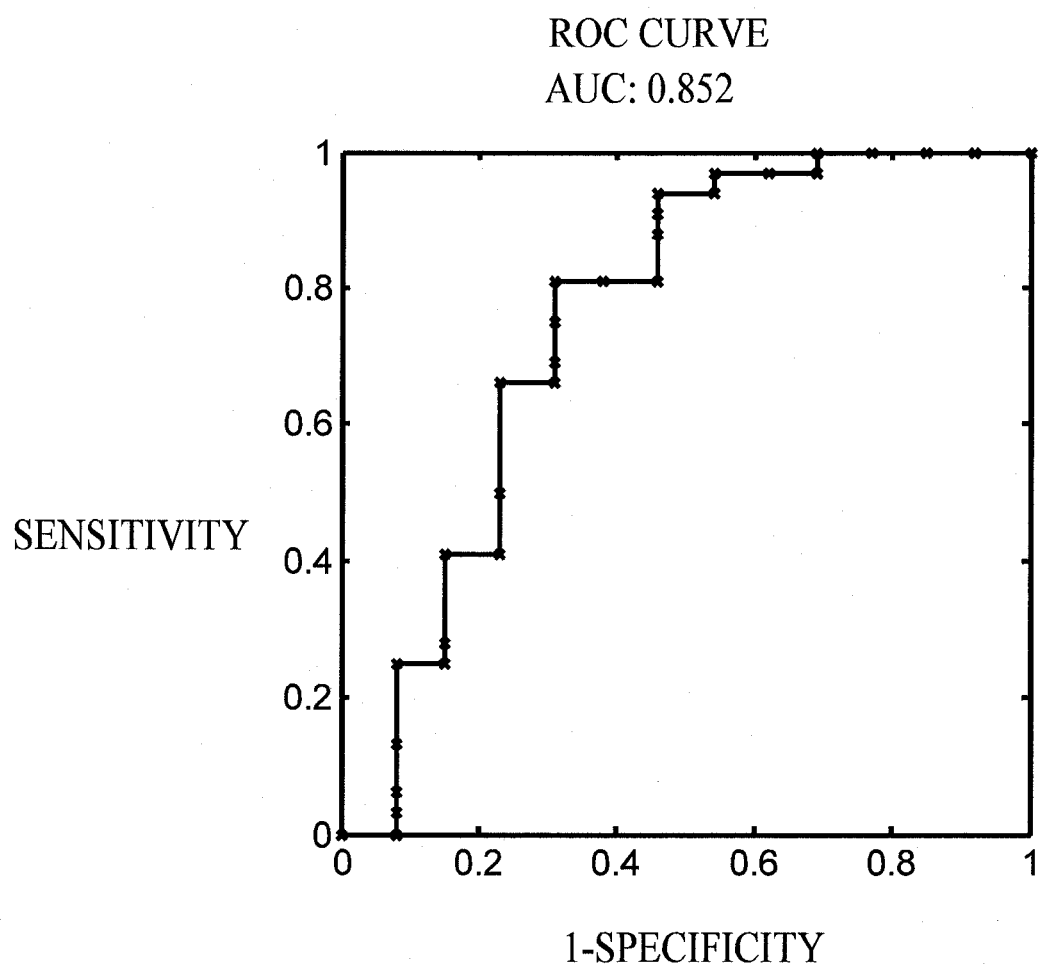
FIGS. 7A-H are graphs representing statistical analysis including receiver operating characteristic (ROC) curve analysis of the FTIR absorption spectra analysis, based on PBMC and plasma samples from colorectal cancer patients, subjects with benign colorectal tumors, and controls, derived in accordance with some applications of the present invention.
Figure 7B:
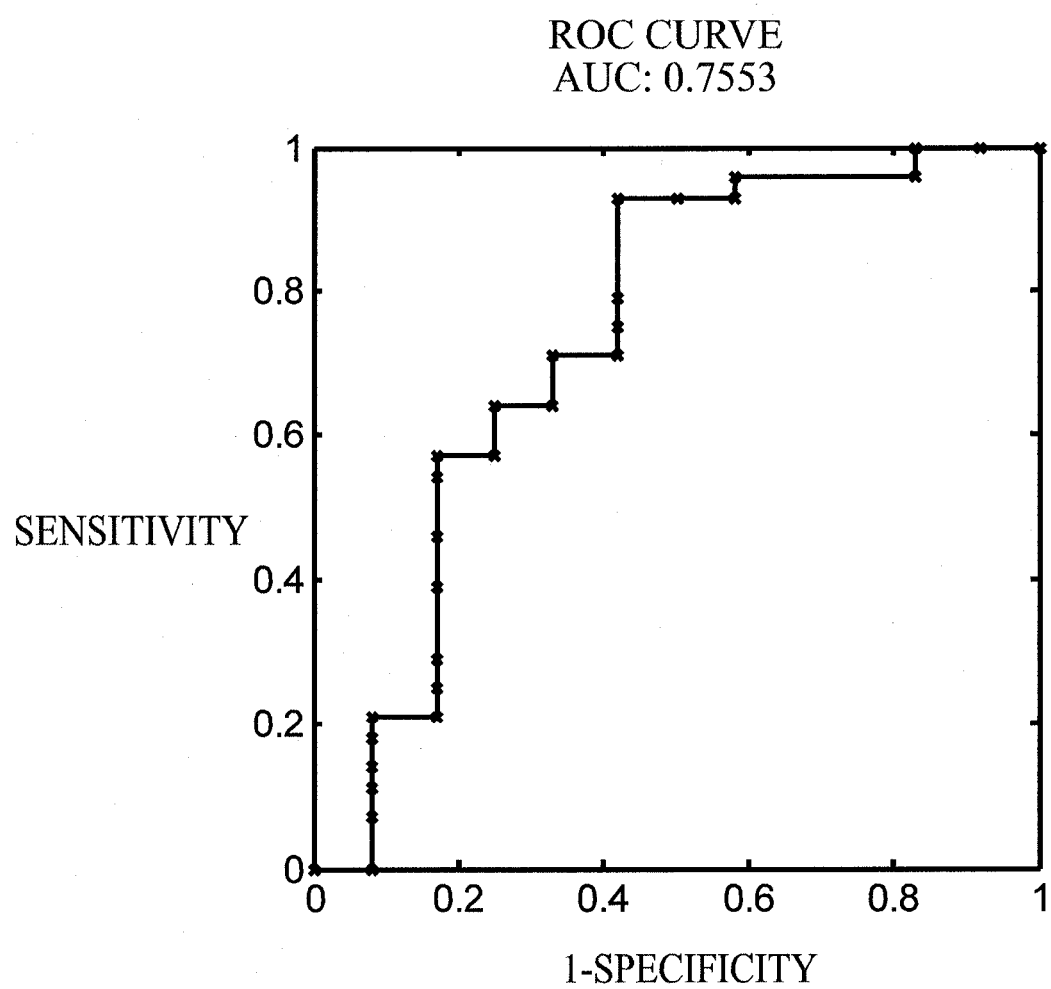
Figure 7C:
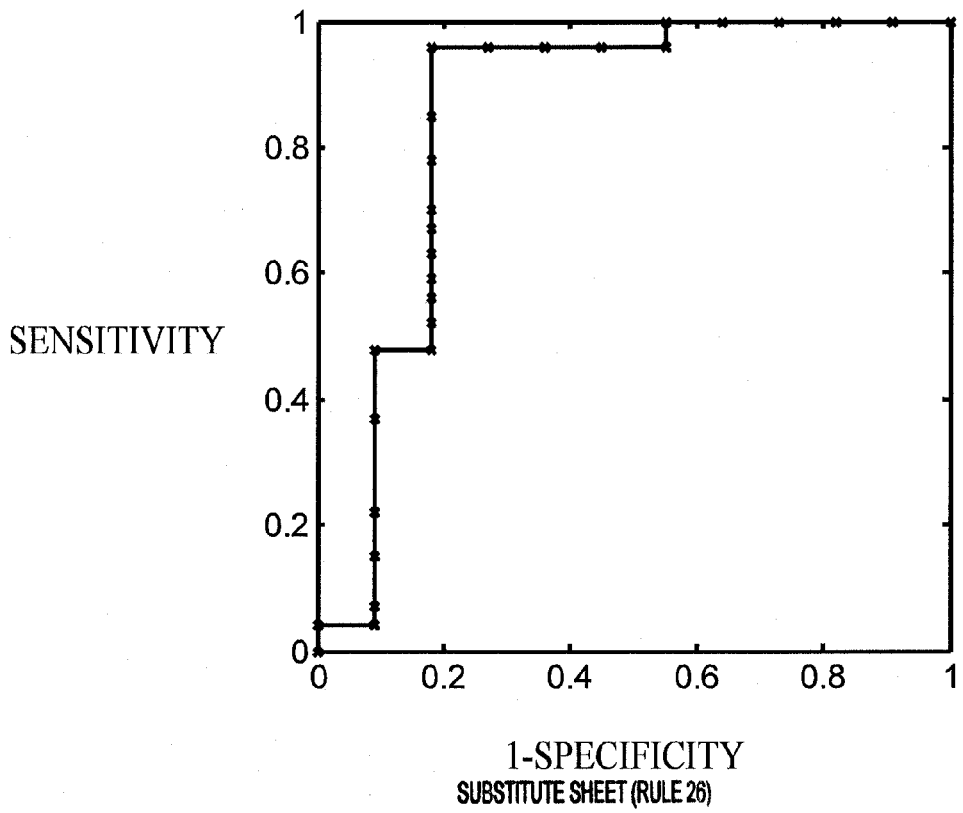

FIGS. 7A-C show receiver operating characteristic (ROC) curve analysis, including the area under the curve (AUC), of PBMC (FIG. 7A) and plasma (FIG. 7B) of colorectal cancer patients compared to the subjects with benign colorectal tumor. As shown, combined use of both the plasma and PBMC samples (FIG. 7C) increased sensitivity and specificity for the distinguishing between a benign colorectal tumor and a malignant colorectal tumor.

Figure 7D:
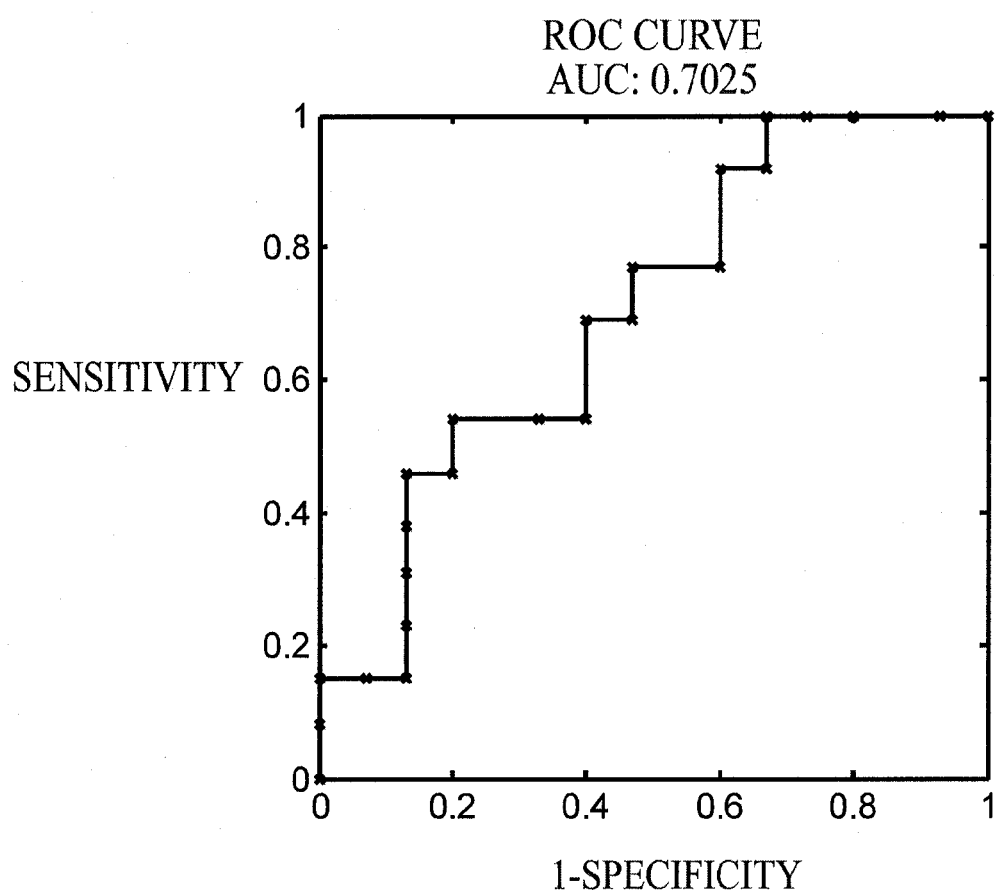
Figure 7E:
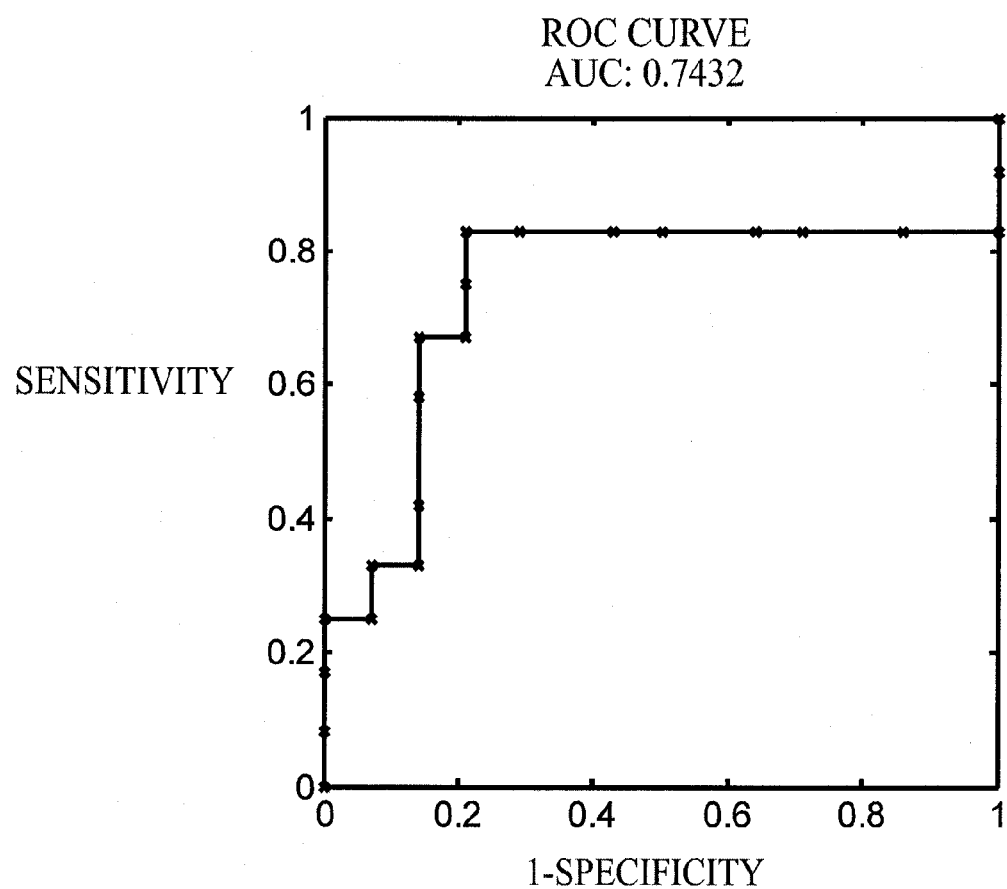
Figure 7F:
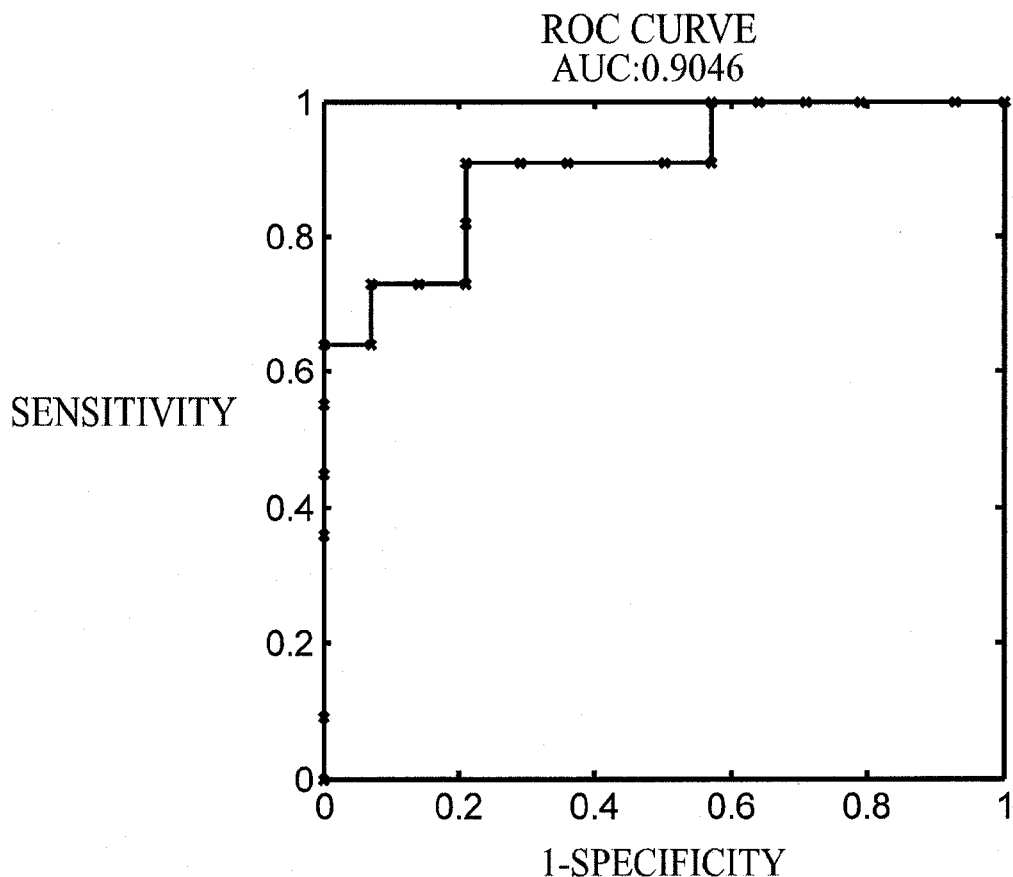

FIGS. 7D-F show receiver operating characteristic (ROC) curve analysis, including the area under the curve (AUC), of PBMC (FIG. 7D) and plasma (FIG. 7E) of healthy controls compared to subjects with a benign colorectal tumor. As shown, combined use of both the plasma and PBMC samples (FIG. 7F) increased sensitivity and specificity for the diagnosis of a benign colorectal tumor.

Figure 7G:
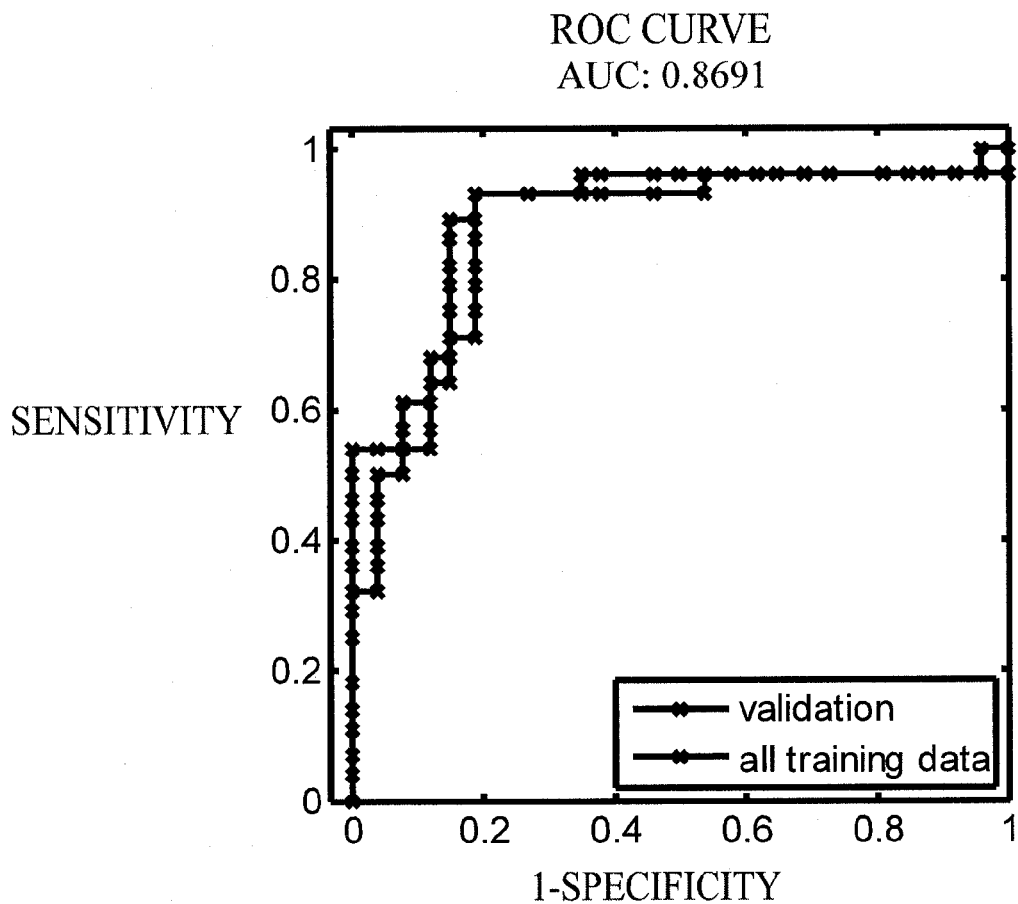

FIG. 7G shows receiver operating characteristic (ROC) curve analysis, including the area under the curve (AUC), of plasma samples of colorectal cancer patients compared to the subjects with benign breast tumors and healthy controls. Values for sensitivity and specificity are presented in FIG. 7G.

Figure 7H:
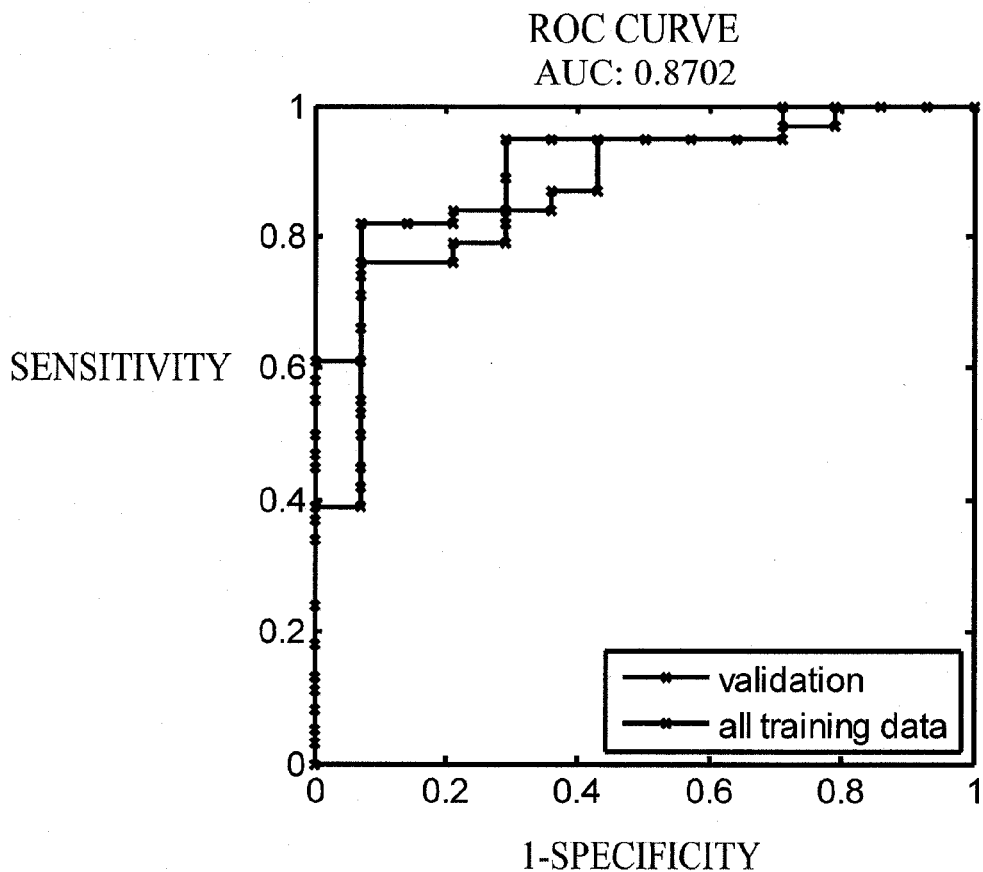

FIG. 7H shows receiver operating characteristic (ROC) curve analysis, including the area under the curve (AUC), of combined use of plasma and PBMC samples of colorectal cancer patients compared to the subjects with benign breast tumors and healthy controls. Values for sensitivity and specificity are presented in FIG. 7H.

Reference is now made to FIGS. 8A-D and Table J1. Table J1 includes clinical information for 23 colorectal cancer patients. FIGS. 8A-D show analysis of PBMC samples (FIGS. 8A-B) and plasma samples (FIGS. 8C-D) obtained from the colorectal cancer patients in accordance with some applications of the present invention.

Table J1 is a table representing clinical data for 23 colorectal cancer patients who took part in the studies described herein. In Tale J1:

Gender column: "M" represents Male and "F" represents Female

Main organ column: "R" represents Rectum and "C" represents Colon

Location at main organ column: "Re" represents Rectum, "Rt" represents Right, "L" represents Left, "C" represents Colon, "A" represents Ascending, Pathology column: "M" represents Malignant and "PM" represents Pre-Malignant Malignancy type column: AC represents Adenocarcinoma.

"#M" represents number of masses

"MS" represents mass size (in mm)

"LN" represents number of lymph nodes

TABLE J1

| Gender | Age | Main Organ | Location at main Organ | MS | # M | LN | # Positive LN | Margin | Vascular Invasion | Pathology | Stage T | N | M | S No | S Sub | Malignancy type |
|---|---|---|---|---|---|---|---|---|---|---|---|---|---|---|---|---|
| M | 80 | R | Re | NA | NA | 10 | 2 | R0 | NA | M | 3 | 1 | 0 | 3 | b | AC |
| M | 66 | R | Re | 15 | 1 | 18 | 0 | R0 | No | PM | | | | | | sessile villous adenoma HGD |
| M | 72 | C | A | 90 | 1 | 11 | 0 | R0 | NA | M | 3 | 0 | 0 | 2 | a | Mucinous AC |
| M | 61 | C | Rt | 18 | 1 | 16 | 0 | R0 | No | PM | | | | | | TVA HGD |
| M | 56 | C | Rt | 70 | 1 | 16 | 12 | R0 | NA | M | 3 | 2 | 0 | 3 | c | AC |
| F | 74 | C | L | NA | 1 | 20 | 0 | R0 | NA | M | 3 | 0 | 0 | 2 | a | AC |
| F | 37 | C | C | NA | 1 | NA | NA | R0 | No | M | 1 | 0 | 0 | 1 | — | AC |
| F | 83 | C | L | 55 | 1 | 15 | 0 | R0 | No | M | 3 | 0 | 0 | 2 | a | AC |
| F | 82 | C | Rt | NA | 1 | 20 | 0 | R0 | NA | M | 3 | 0 | 0 | 2 | a | Mucinous AC |
| M | 69 | C | Rt | 6 | 1 | 14 | 0 | R0 | No | M | 3 | 0 | 0 | 2 | a | AC |
| M | 59 | C | Rt | 9 | 1 | 10 | 1 | R0 | Yes | M | 3 | 1 | 0 | 3 | b | Mucinous AC |
| M | 88 | C | Rt | 33 | 1 | 18 | 0 | R0 | No | M | 3 | 0 | 0 | 2 | a | AC |
| M | 72 | C | Rt | NA | 1 | 20 | 0 | R0 | No | U | | | | | | TVA HGD |
| F | 69 | C | L | NA | 1 | 4 | 0 | R0 | No | M | 2 | 0 | 0 | 1 | — | AC |
| F | 68 | C | Rt | NA | 1 | 11 | 4 | R1 | Yes | M | 3 | 2 | 0 | 3 | b | AC |
| F | 88 | C | L | 46 | 1 | 27 | 0 | R0 | NA | M | 3 | 0 | 0 | 2 | a | AC |
| F | 54 | C | Rt | NA | 1 | 19 | 0 | R0 | No | M | 3 | 0 | 0 | 2 | a | AC |
| F | 84 | C | Rt | 60 | 1 | 15 | 0 | R0 | Yes | M | 3 | 0 | 0 | 2 | a | AC |
| M | 81 | C | Rt | 22 | 1 | 23 | 0 | R0 | NA | M | 3 | 0 | 0 | 2 | a | AC |
| F | 69 | C | L | 25 | 1 | 4 | 0 | R0 | No | M | 2 | 0 | 0 | 1 | — | AC |
| M | 45 | R | Re | 50 | 1 | 11 | 3 | R0 | No | M | 3 | 1 | 0 | 3 | b | AC |
| M | 93 | C | C | NA | NA | 4 | 0 | NA | NA | U | | | | | | TVA HGD |
| F | 78 | C | L | NA | 1 | 16 | 13 | R0 | Yes | M | 3 | 2 | 0 | 3 | c | AC |

Figure 8A:
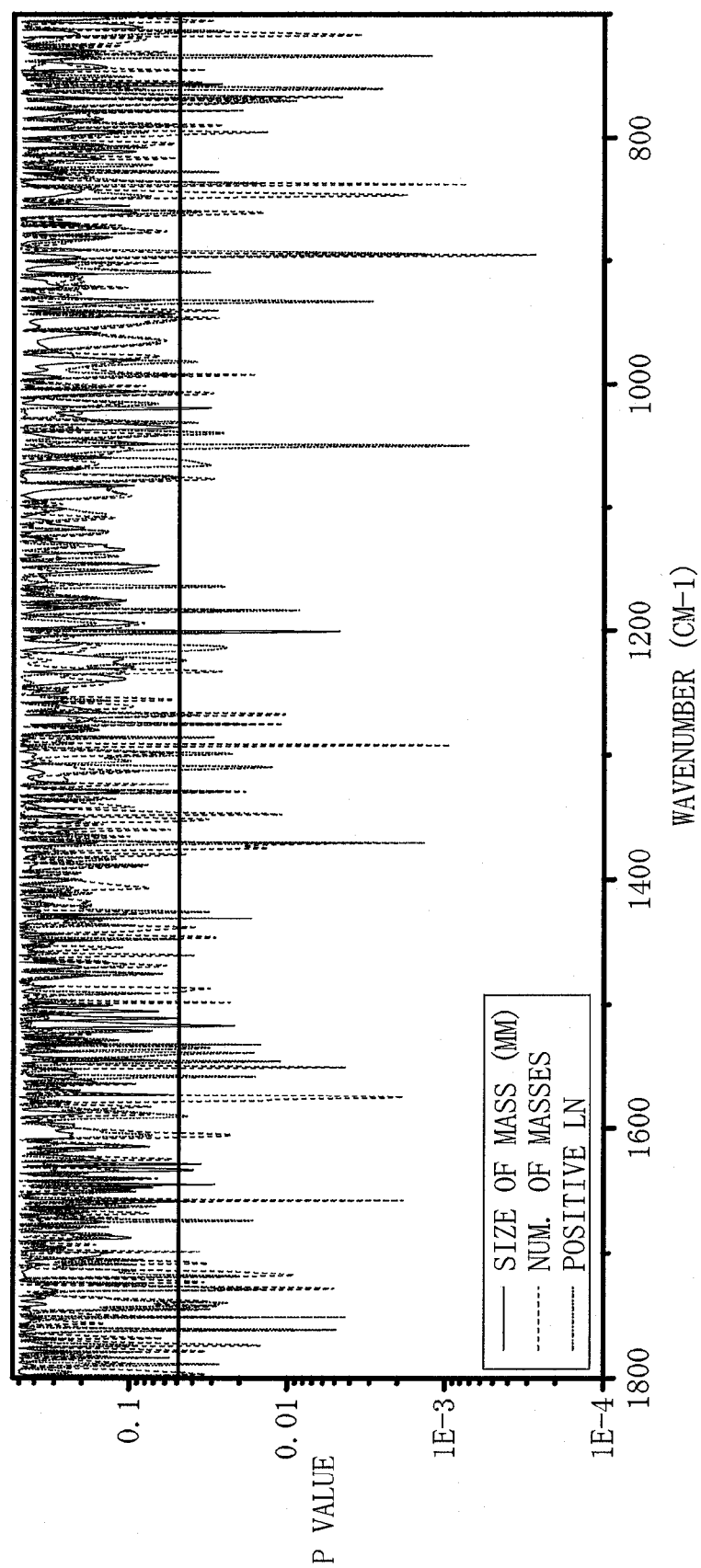
Figure 8B:
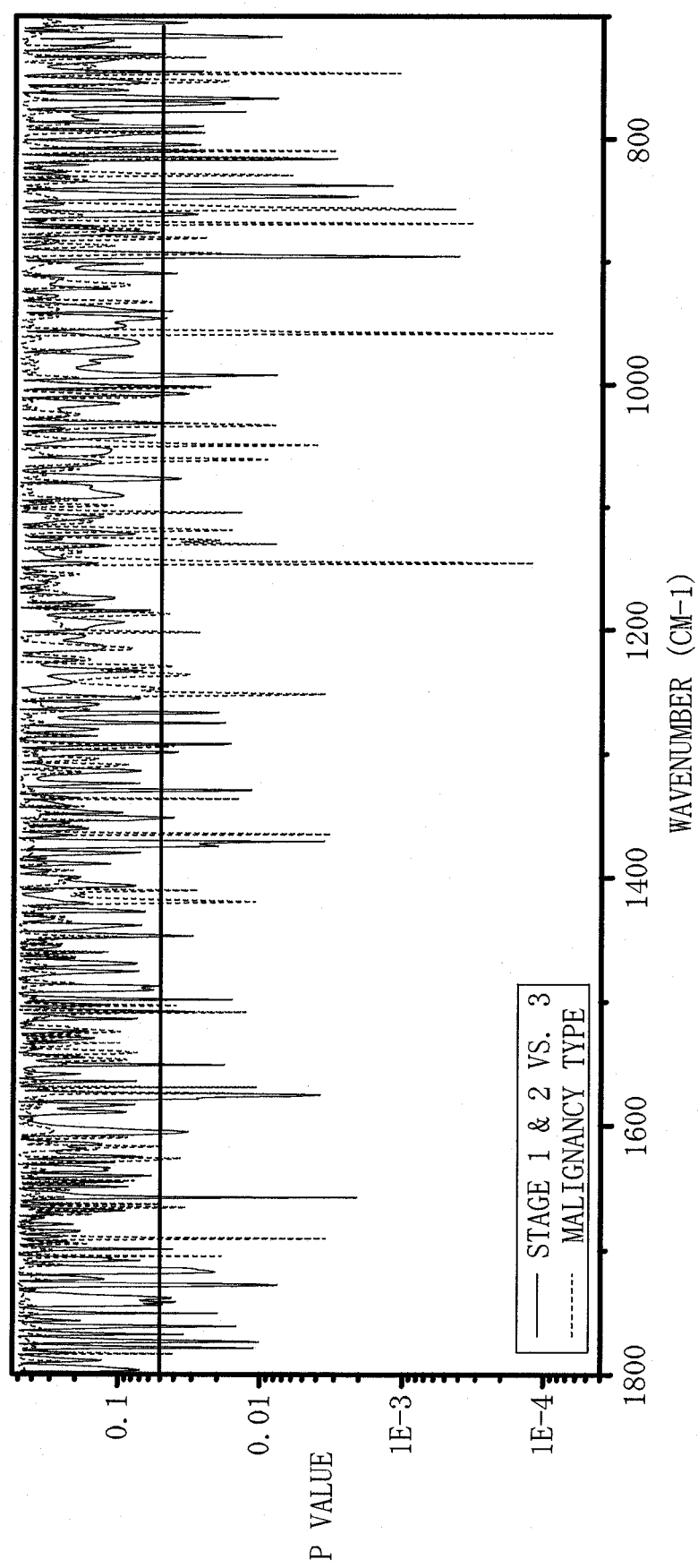

FIGS. 8A-B are graphs representing analysis of the effect of various clinical parameters (Table J1) of the colorectal cancer patients on FTIR spectra of PBMC samples. Statistical analysis was performed and P-values are provided. As shown, in accordance with some applications of the present invention, it is possible to identify a distinct spectral pattern in FTIR analysis of PBMC samples. The distinct spectral pattern is caused in response to at least one of the following parameters of the colorectal cancer patients: size of the mass, number of masses, positive lymph nodes (LN), malignancy type, and distinguishing between stages 1 and 2 and stage 3 of the disease.

Table J2 lists wavenumbers that were identified in this set of experiments as presented in FIGS. 8B-C. Typically, PBMC samples were analyzed by FTIR-MSP techniques using these wavenumbers to identify spectral patterns for the following parameters based on PBMC samples from the colorectal cancer patients: size of the mass, number of masses, positive lymph nodes (LN), malignancy type, and distinguishing between stages 1 and 2 and stage 3 of the disease. For some applications, the PBMC samples are analyzed by FTIR-MSP at at least one wavenumber selected from Table J2. Alternatively, the PBMC samples are analyzed by FTIR-MSP at at least two or three wavenumbers selected from Table J:

TABLE J2

| Malignancy Type Wavenumber (cm-1 ± 4) | Stage Wavenumber (cm-1 ± 4) | Number of masses Wavenumber (cm-1 ± 4) | Num. of Positive LN Wavenumber (cm-1 ± 4) | Size of Mass (mm) Wavenumber (cm-1 ± 4) |
|---|---|---|---|---|
| 746.3 | 705.3 | 713.5 | 704.9 | 756.4 |
| 753.1 | 716.9 | 734.3 | 716.4 | 1019.2 |
| 809.5 | 767.0 | 759.8 | 755.0 | 1201.0 |
| 815.3 | 789.7 | 766.1 | 766.6 | 1516.3 |
| 829.2 | 804.7 | 769.9 | 770.9 | 1632.9 |
| 856.7 | 810.0 | 836.5 | 789.7 | 1645.0 |
| 868.8 | 815.7 | 860.1 | 796.0 | |
| 880.8 | 837.9 | 893.8 | 837.9 | |
| 892.9 | 846.6 | 909.3 | 846.6 | |
| 957.5 | 861.1 | 932.9 | 847.1 | |
| 1033.2 | 895.8 | 946.9 | 861.1 | |
| 1049.1 | 992.2 | 981.6 | 895.3 | |
| 1061.1 | 1007.6 | 992.2 | 945.9 | |
| 1104.0 | 1076.6 | 1006.2 | 991.2 | |
| 1118.5 | 1266.5 | 1031.2 | 1007.1 | |
| 1129.6 | 1274.7 | 1039.4 | 1076.6 | |
| 1145.0 | 1298.3 | 1050.1 | 1183.6 | |
| 1186.5 | 1329.2 | 1063.5 | 1232.3 | |
| 1201.9 | 1351.9 | 1075.6 | 1266.5 | |
| 1229.4 | 1371.1 | 1163.3 | 1292.6 | |
| 1235.7 | 1446.4 | 1183.1 | 1329.7 | |
| 1251.6 | 1497.9 | 1213.0 | 1351.9 | |
| 1293.0 | 1507.6 | 1224.1 | 1371.1 | |
| 1364.9 | 1574.6 | 1267.5 | 1438.2 | |
| 1418.4 | 1605.4 | 1274.7 | 1445.9 | |
| 1626.7 | 1657.5 | 1298.8 | 1488.3 | |
| 1665.7 | 1715.9 | 1310.4 | 1550.0 | |
| 1690.3 | 1727.9 | 1329.2 | 1575.1 | |
| | 1739.0 | 1370.7 | 1605.9 | |
| | 1761.2 | 1371.1 | 1657.5 | |
| | 1773.7 | 1425.6 | 1707.2 | |
| | | 1535.5 | 1707.7 | |
| | | 1540.4 | 1717.3 | |
| | | 1546.1 | 1727.9 | |
| | | 1558.7 | 1738.0 | |
| | | 1590.5 | 1742.9 | |
| | | 1673.9 | 1773.7 | |
| | | 1718.3 | | |
| | | 1727.9 | | |
| | | 1740.4 | | |

For some applications, one, two, three, or more of the following wavenumbers selected from Table J2 are used to identify in PBMC samples a distinct spectral pattern caused by a malignancy type of the colorectal tumor: 868.8±4 cm-1, 957.5±4 cm-1, 1145.0±4 cm-1, 1251.6±4 cm-1, and 1364.9±4 cm-1.

For some applications, one, two, three, or more of the following wavenumbers selected from Table J2 are used to distinguish between stage 1 and 2 and stage 3 of colorectal tumor: 815.7±4 cm-1, 837.9±4 cm-1, 895.8±4 cm-1, 992.2±4 cm-1, 1371.1±4 cm-1, 1574.6±4 cm-1 and 1657.5±4 cm-1.

For some applications, one, two, three, or more of the following wavenumbers selected from Table J2 are used to identify in PBMC samples a distinct spectral pattern caused by the number of masses of a colorectal tumor: 734.3±4 cm-1, 759.8±4 cm-1, 893.8±4 cm-1, 932.9±4 cm-1, 1370.7±4 cm-1, 1412.1±4 cm-1, and 1578.9±4 cm-1.

For some applications, one, two, three, or more of the following wavenumbers selected from Table J2 are used to identify in PBMC samples a distinct spectral pattern caused by the number of positive lymph nodes of a colorectal cancer patient: 837.9±4 cm-1, 895.3±4 cm-1, 1292.6±4 cm-1, 1371.1±4 cm-1, 1550.0±4 cm-1, and 1575.1±4 cm-1.

For some applications, one, two, three, or more of the following wavenumbers selected from Table J2 are used to identify in PBMC samples a distinct spectral pattern caused by the size of the mass (mm) of the colorectal tumor: 756.4 cm-1, 1019.2±4 cm-1, 1201.0±4 cm-1, and 1516.3±4 cm-1.

Figure 8D:
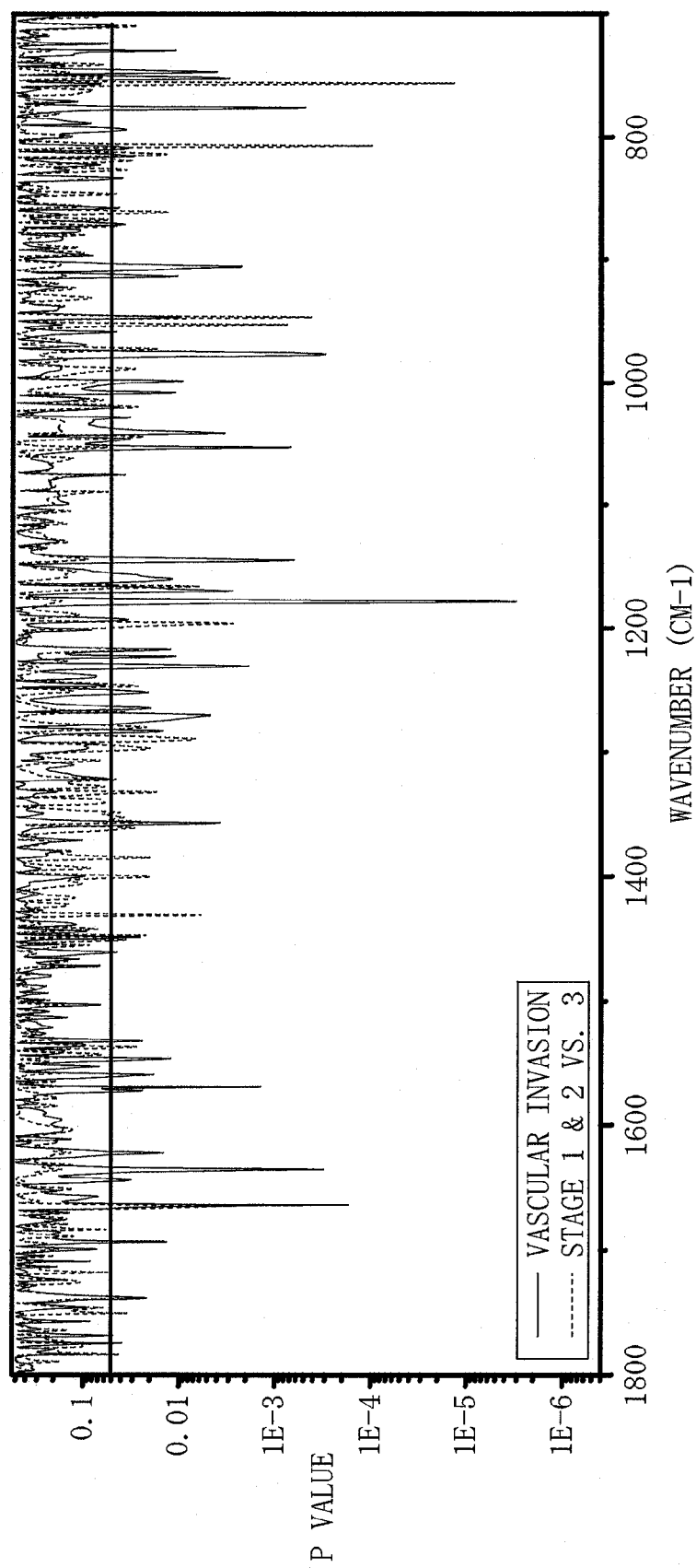

FIGS. 8C-D are graphs representing analysis of various clinical parameters of the colorectal cancer patients as derived from Table J1. Statistical analysis was performed and P-values are provided. As shown, in accordance with some applications of the present invention, it is possible to identify a distinct FTIR spectral pattern in plasma samples due to the following parameters of colorectal cancer patients: size of the mass, positive lymph nodes (LN), vascular invasion, and distinguishing between stages 1 and 2 and stage 3 of the disease.

Table K lists wavenumbers that were identified in this set of experiments as presented in FIGS. 8C-D. Typically, plasma samples were analyzed by FTIR-MSP techniques using these wavenumbers to identify the effect of the following parameters on FTIR spectral pattern of plasma samples of the colorectal cancer patients: size of the mass, positive lymph nodes (LN), vascular invasion and distinguishing between stages 1 and 2 and stage 3 of the disease. For some applications, the plasma samples are analyzed by FTIR-MSP at at least one wavenumber selected from Table K. Alternatively, the plasma samples are analyzed by FTIR-MSP at at least two or three wavenumbers selected from Table K:

TABLE K

| Vascular Invasion Wavenumber (cm-1 ± 4) | Stage Wavenumber (cm-1 ± 4) | Num. of Positive LN Wavenumber (cm-1 ± 4) | Size of Mass (mm) Wavenumber (cm-1 ± 4) |
|---|---|---|---|
| 729.4 | 1157.1 | 709.7 | 710.2 | 740.5 |
| 746.3 | 1168.2 | 756.4 | 756.4 | 832.1 |
| 751.1 | 1177.3 | 806.6 | 807.1 | 844.7 |
| 775.7 | 1192.3 | 813.3 | 813.3 | 992.7 |
| 793.1 | 1216.9 | 819.1 | 818.6 | 1051.0 |
| 808.0 | 1222.2 | 826.3 | 826.8 | 1155.2 |
| 814.8 | 1229.9 | 861.1 | 833.6 | 1377.4 |
| 833.6 | 1251.1 | 872.6 | 861.1 | 1426.1 |
| 857.7 | 1264.6 | 945.9 | 872.1 | 1578.0 |
| 870.7 | 1269.9 | 952.2 | 910.2 | 1669.6 |
| 905.4 | 1282.4 | 971.9 | 945.9 | 1712.5 |
| 912.6 | 1356.7 | 988.3 | 952.2 | 1718.3 |
| 946.4 | 1531.7 | 1018.7 | 1013.4 | 1728.9 |
| 958.0 | 1546.1 | 1043.8 | 1019.2 | 1740.4 |
| 976.3 | 1559.2 | 1165.3 | 1043.8 | 1751.0 |
| 998.0 | 1568.8 | 1196.1 | 1052.9 | 1756.8 |
| 1007.6 | 1572.2 | 1216.9 | 1164.8 | 1767.9 |
| 1019.2 | 1621.4 | 1245.8 | 1172.5 | 1773.2 |
| 1028.4 | 1635.3 | 1267.5 | 1195.6 | 1778.0 |
| 1040.4 | 1643.1 | 1279.1 | 1356.7 | |
| 1046.2 | 1663.8 | 1288.7 | 1664.3 | |
| 1052.9 | 1692.7 | 1664.3 | 1725.5 | |
| 1074.6 | 1738.0 | 1738.0 | 1746.2 | |
| 1143.6 | | | 1763.6 | |

For some applications, one, two, three, or more of the following wavenumbers selected from Table K are used to identify in plasma samples a distinct spectral pattern caused by vascular invasion of a colorectal tumor: 976.3±4 cm-1, 1052.9±4 cm-1, 1143.6±4 cm-1, 1177.3±4 cm-1, 1229.9±4 cm-, and 1356.7±4 cm-1.

For some applications, one, two, three, or more of the following wavenumbers selected from Table K are used to distinguish between stage 1 and 2 and stage 3 of colorectal tumor: 756.4±4 cm-1, 806.6±4 cm-1, 945.9±4 cm-1, 1165.3±4 cm-1, 1196.1±4 cm-1, 1288.7±4 cm-1 and 1657.5±4 cm-1.

For some applications, one, two, three, or more of the following wavenumbers selected from Table K are used to identify in plasma samples a distinct spectral pattern caused by the number of positive lymph nodes of a colorectal cancer patient: 756.4±4 cm-1, 807.1±4 cm-1, 861.1±4 cm-1, 872.1±4 cm-1, 945.9±4 cm-1, and 1164.8±4 cm-1.

For some applications, one, two, three, or more of the following wavenumbers selected from Table K are used to identify in plasma samples a distinct spectral pattern caused by the size of the mass (mm) of the colorectal tumor: 740.5±4 cm-1, 844.7±4 cm-1, 1051.0±4 cm-1, and 1377.4±4 cm-1, 1751.0±4 cm-1, 1778.0±4 cm-1.

Reference is made to FIGS. 9A-D which are graphs representing statistical analysis and P-values of PBMC (FIGS. 9A-B) and plasma samples (FIGS. 9C-D) from colorectal cancer patients (Cn), subjects with pre-malignant colorectal tumors (HGD), subjects with benign colorectal tumors (Bn), and healthy controls (Hl), derived in accordance with some applications of the present invention.

Figure 9A:
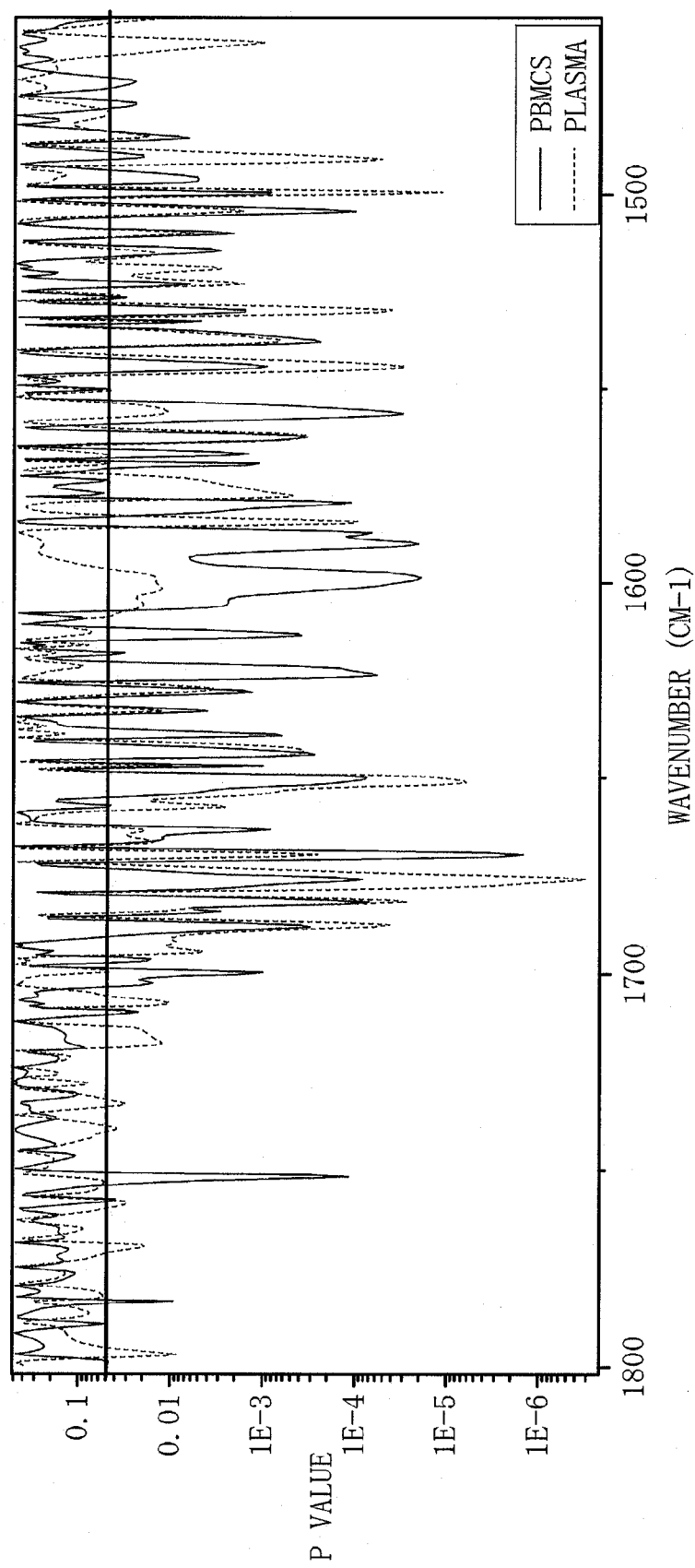
FIGS. 9A-D are graphs representing statistical analysis of PBMC and plasma samples from colorectal cancer patients, subjects with pre-malignant colorectal tumors, subjects with benign colorectal tumors, and controls, derived in accordance with some applications of the present invention.
Figure 9B:
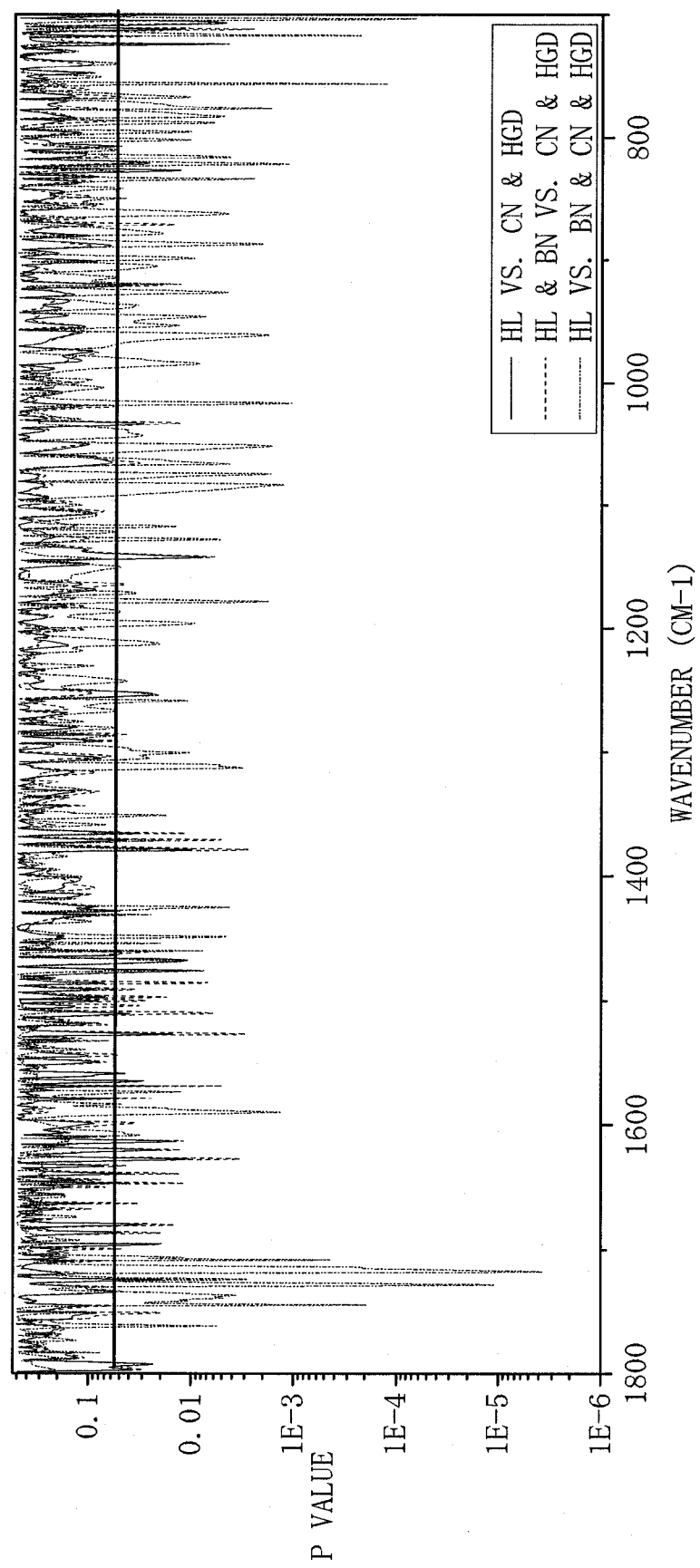

As shown in FIGS. 9A-B, PBMC samples that were analyzed by FTIR-MSP techniques allow distinguishing between: a) healthy control and colorectal cancer patients; b) healthy controls and subjects with benign colorectal tumors vs. colorectal cancer patients; c) subjects with pre-malignant colorectal tumors exhibiting high grade dysplasia vs. cancer patients; d) healthy controls vs. colorectal cancer patients and subjects with pre-malignant colorectal tumors exhibiting high grade dysplasia; e) healthy control and subjects with benign colorectal tumors vs. colorectal cancer patients and subjects with pre-malignant colorectal tumors exhibiting high grade dysplasia; and f) healthy controls vs. subjects with benign colorectal tumors, colorectal cancer patients and subjects with pre-malignant colorectal tumors exhibiting high grade dysplasia.

Figure 9C:
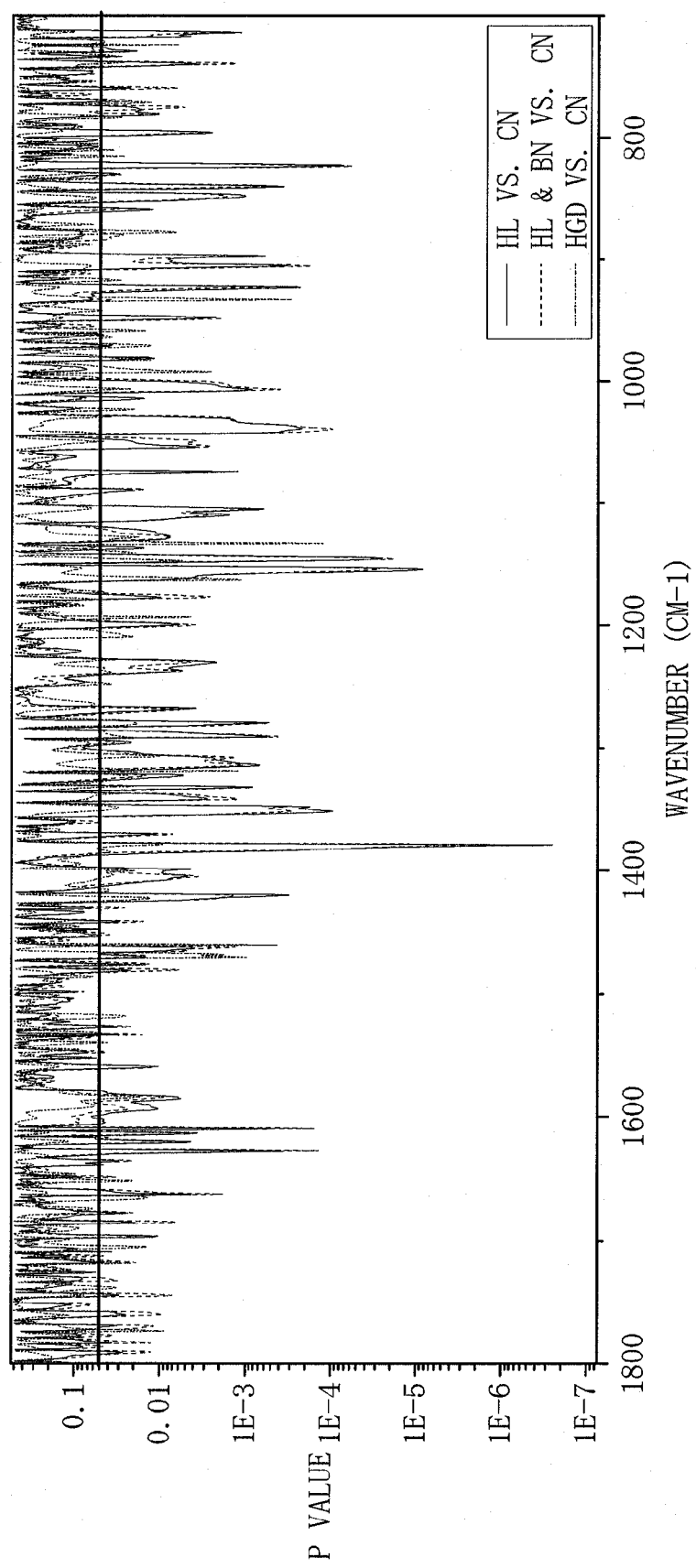
Figure 9D:
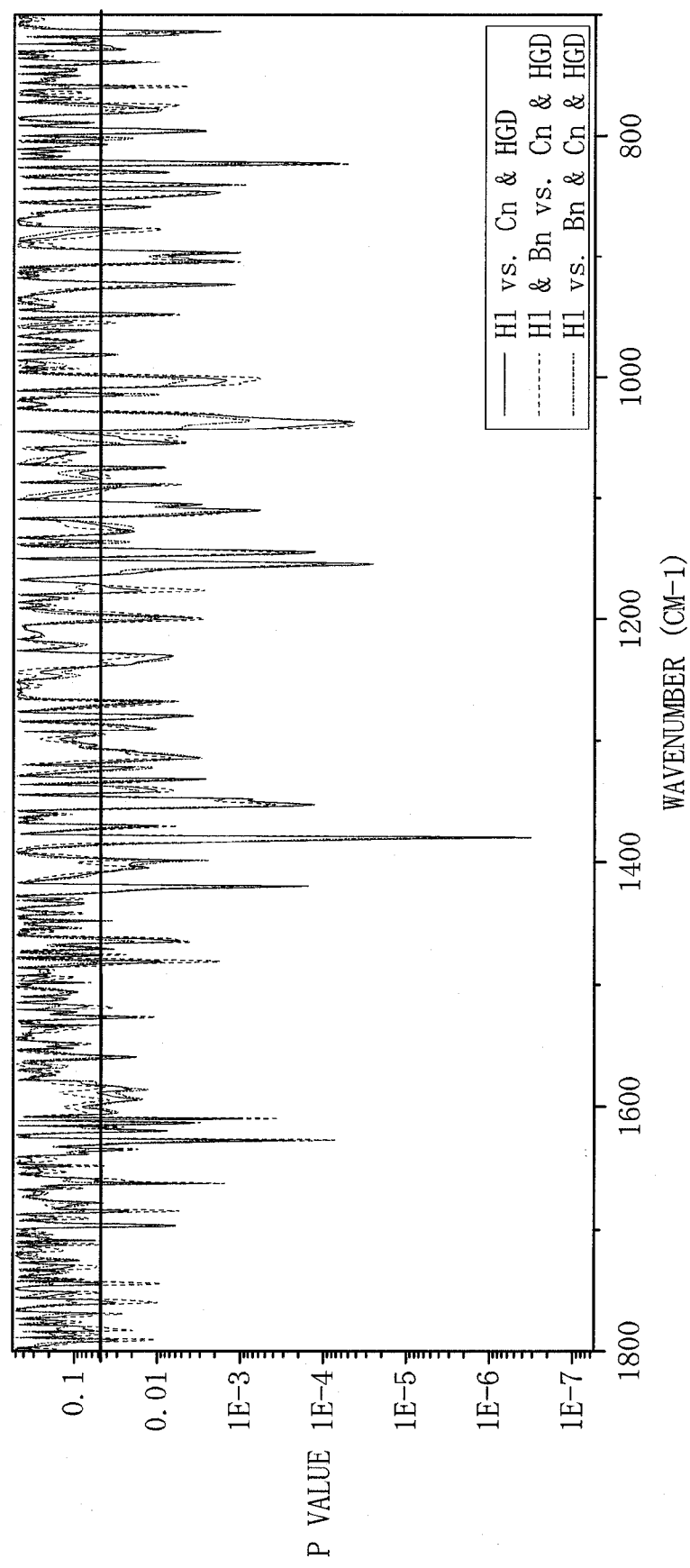

As shown in FIGS. 9C-D, plasma samples that were analyzed by FTIR-MSP techniques allow distinguishing between: a) healthy control and colorectal cancer patients; b) healthy controls and subjects with benign colorectal tumors vs. colorectal cancer patients; c) subjects with pre-malignant colorectal tumors exhibiting high grade dysplasia vs. cancer patients; d) healthy controls vs. colorectal cancer patients and subjects with pre-malignant colorectal tumors exhibiting high grade dysplasia; e) healthy control and subjects with benign colorectal tumors vs. colorectal cancer patients and subjects with pre-malignant colorectal tumors exhibiting high grade dysplasia; and f) healthy controls vs. subjects with benign colorectal tumors, colorectal cancer patients and subjects with pre-malignant colorectal tumors exhibiting high grade dysplasia.

Example 5

In a set of experiments, differential diagnosis of various types of malignant tumors in gynecological tissue was performed based on a FTIR-MSP spectral pattern at selected wavenumbers of PBMC samples. Additionally, differential diagnosis of malignant ovarian tumors and benign ovarian tumors was performed based on a FTIR-MSP spectral pattern at selected wavenumbers of PBMC samples. Patient data is presented hereinabove in Table B. As mentioned hereinabove, an additional control group for this set of experiments consisted of pregnant women (n=11). (Pregnancy may trigger a false positive cancer diagnosis due to physiological changes and the presence of blood markers. Therefore, pregnancy acts as an appropriate control for gynecological tumors and for the effectiveness of some applications of the present invention to differentiate between cancer and other non-cancerous conditions, e.g., pregnancy.)

In accordance with applications of the present invention, PBMC samples from 28 healthy controls were analyzed by FTIR-MSP, and a typical FTIR-MSP spectral pattern was established for control PBMC. Additionally, PBMC samples from 11 ovarian cancer patients, 15 endometrial cancer patients, 6 gynecological sarcoma patients, 7 cervical cancer patients, 4 vulvar cancer patients and 3 patients diagnosed with a borderline ovarian tumor (BOT) were subjected to FTIR-MSP analysis and compared to the control FTIR-MSP spectral pattern. Additionally, PBMC samples from 8 subjects with a benign tumor in ovarian tissue were subjected to FTIR-MSP analysis and compared to the control FTIR-MSP spectral pattern and to the cancer FTIR-MSP spectral pattern. Further additionally, PBMC samples from 11 pregnant women were subjected to FTIR-MSP analysis and compared to the control FTIR-MSP spectral pattern, to the cancer FTIR-MSP spectral pattern and to the benign FTIR-MSP spectral pattern.

The PBMC samples were obtained by preliminary processing of the peripheral blood in accordance with the protocols described hereinabove with reference to extraction of peripheral blood mononuclear cells (PBMC). The PBMC samples were then analyzed by FTIR-MSP, in accordance with the protocols described hereinabove with reference to FTIR-MSP.

Results are presented in FIGS. 10A-E, which are graphs representing FTIR absorption spectra, the second derivative of the absorption spectra, and analysis thereof, based on PBMC samples from the gynecological cancer patients, subjects with benign gynecological tumors, pregnant subjects and healthy controls, derived in accordance with some applications of the present invention.

Figure 10A:
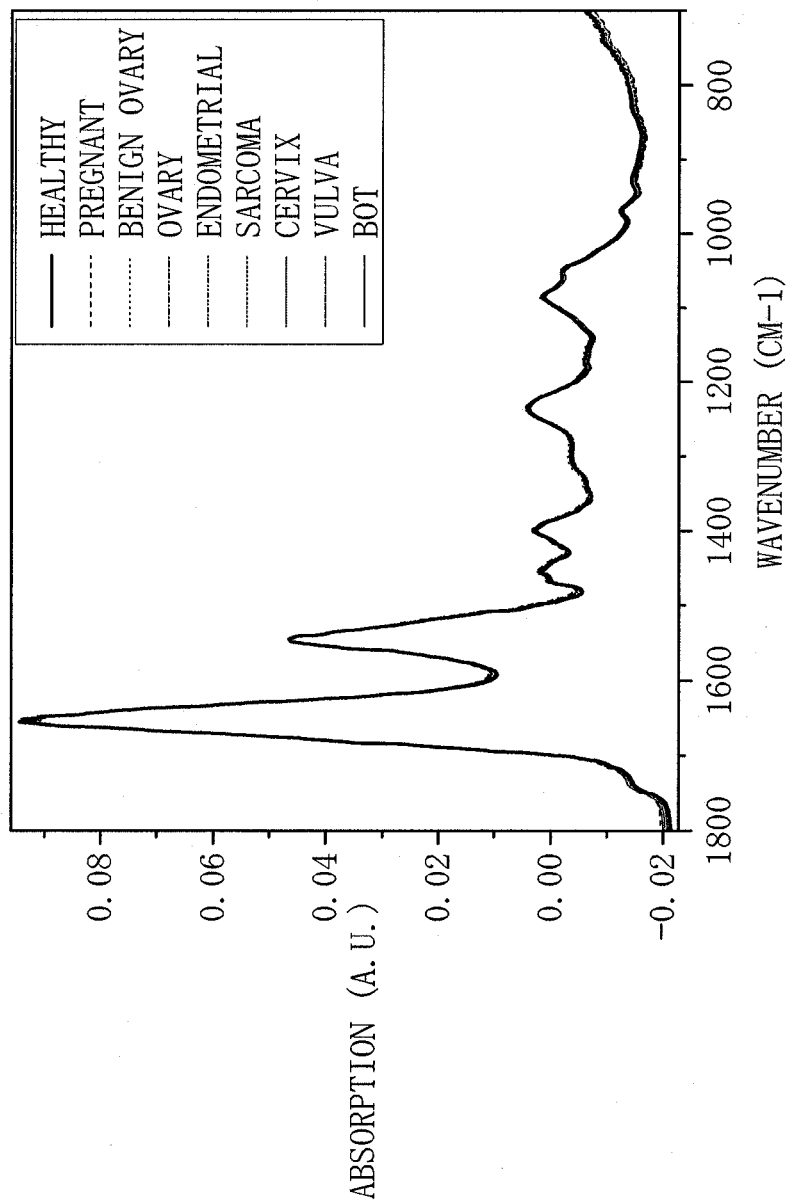
FIGS. 10A-E are graphs representing FTIR absorption spectra, the second derivative of the absorption spectra, and analysis thereof, based on PBMC samples from: gynecological cancer patients, subjects with benign gynecological tumors, pregnant subjects, and healthy controls, derived in accordance with some applications of the present invention.

FIG. 10A shows average FTIR-MSP absorption spectra of PBMC samples of healthy controls, subjects with benign ovarian tumors and gynecological cancer patients in the regions of 700-1800 cm-1, after baseline correction and vector normalization. Each spectrum represents the average of five measurements at different sites for each sample. The spectra are composed of several absorption bands, each corresponding to specific functional groups of specific macromolecules such as lipids, proteins, and carbohydrates/nucleic acids. Generally, the FTIR spectrum is typically analyzed by tracking changes in absorption (intensity and/or shift) of these macromolecules.

Figure 10B:
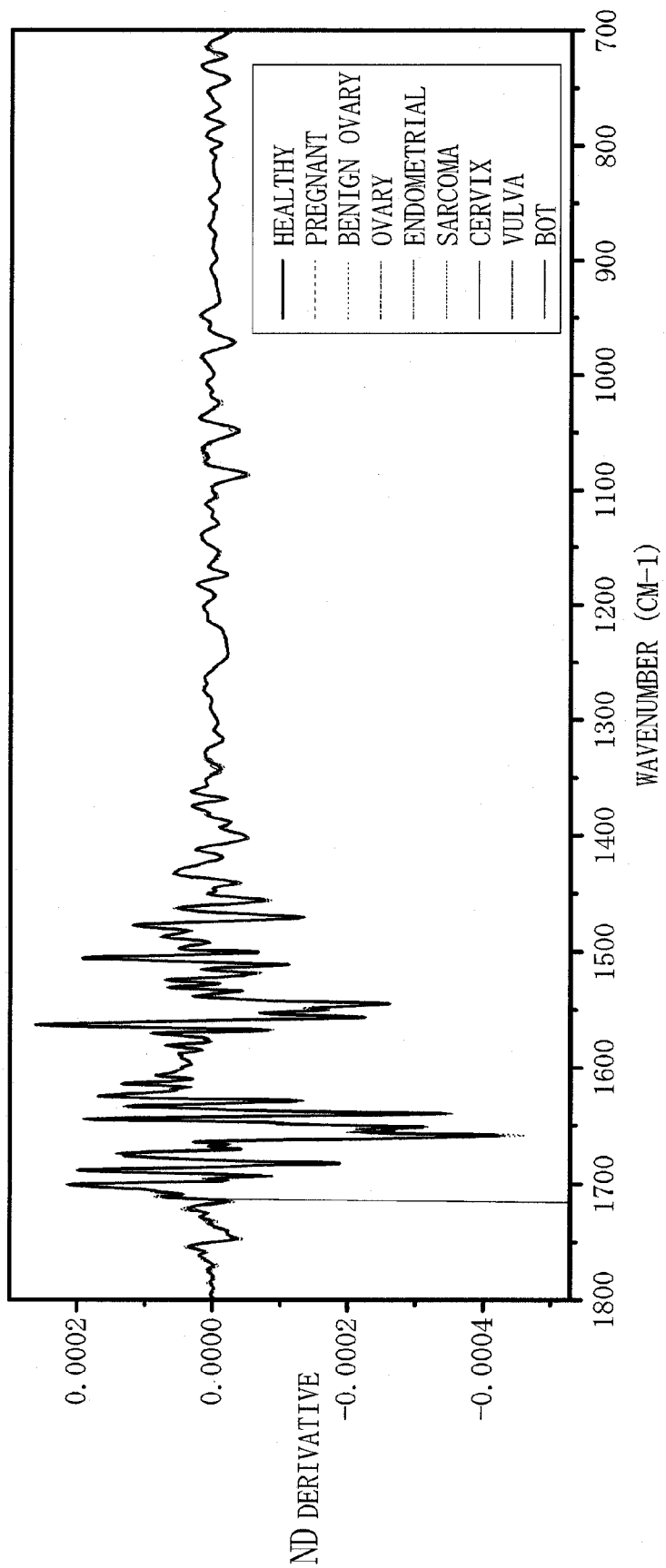
Figure 10C:
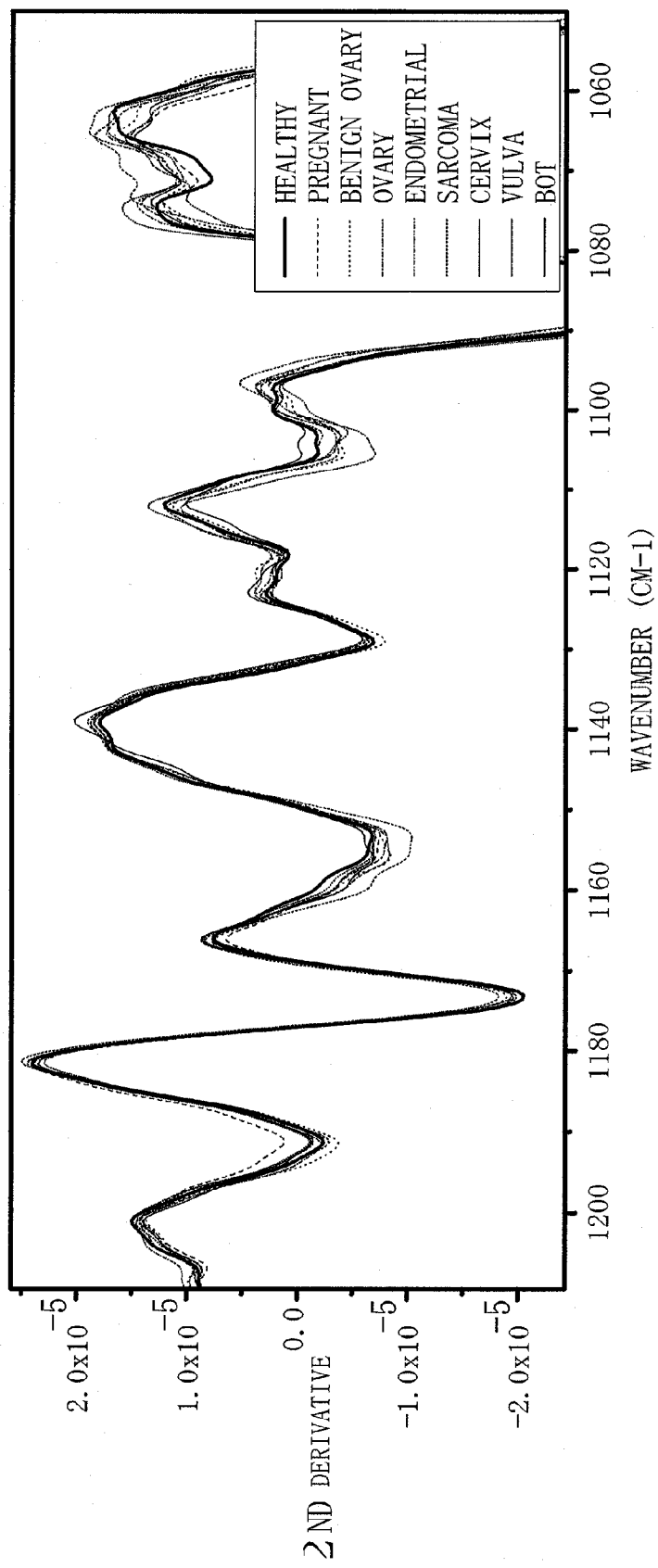

Reference is made to FIGS. 10B-C. In order to achieve effective comparison between the PBMC samples of the various gynecological cancer patients, subjects with benign ovarian tumors, pregnant women and the controls, the second derivative of the baseline-corrected, vector-normalized FTIR-MSP spectra was used. Results are presented in FIGS. 10B-C. As shown from the second derivative spectra analysis, the PBMC samples from the various cancer patients differed from the control and pregnant women group. Additionally, analysis of PBMC by FTIR-MSP of the various cancer patients produced distinct FTIR spectra for each type of gynecological tumor. Accordingly, some applications of the present invention are used to detect a type of a gynecological solid tumor. Typically, each type of malignant gynecological solid tumor produces distinct FTIR spectra of the PBMC, which are unique to the type of solid tumor.

This can be due to each type of solid tumor inducing specific biochemical changes in PBMC.

Figure 10D:
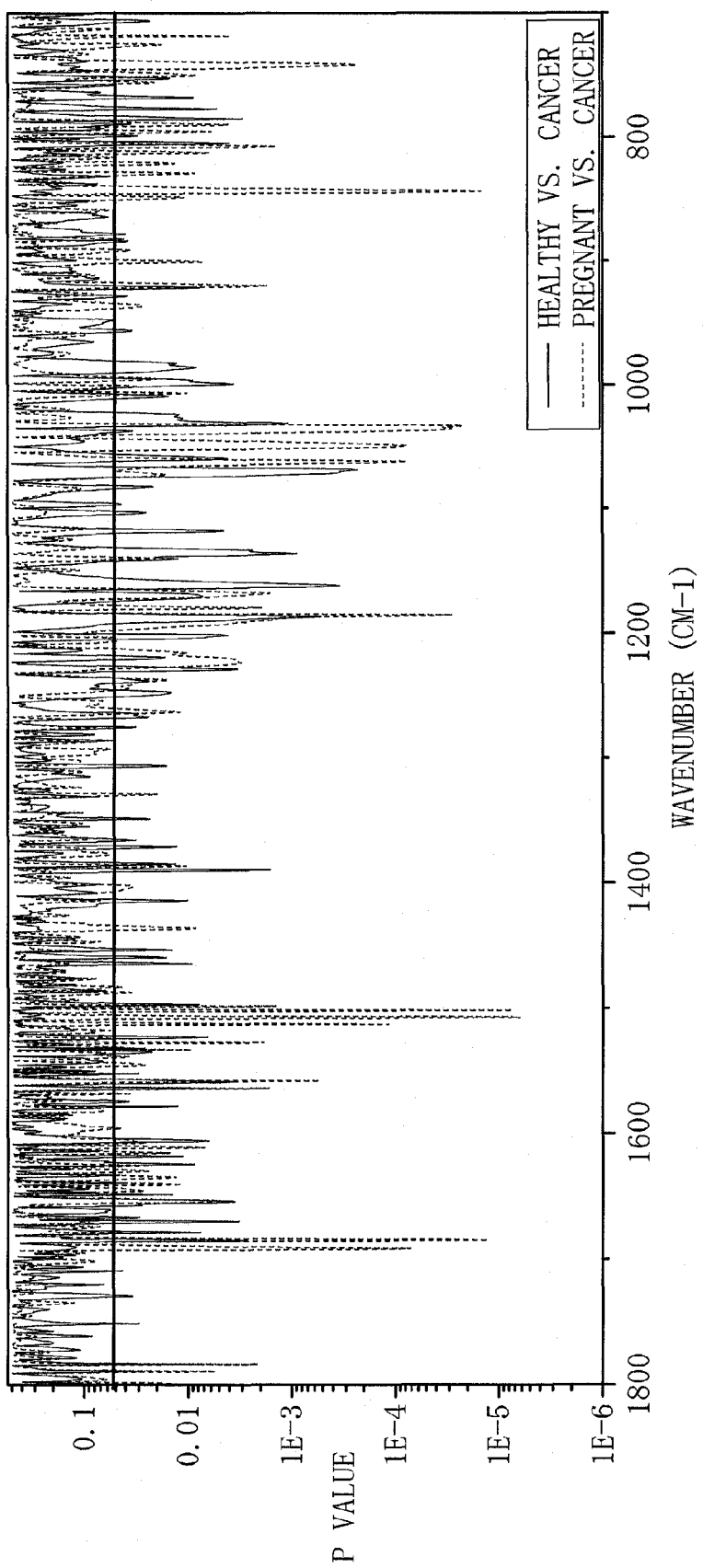
Figure 10E:
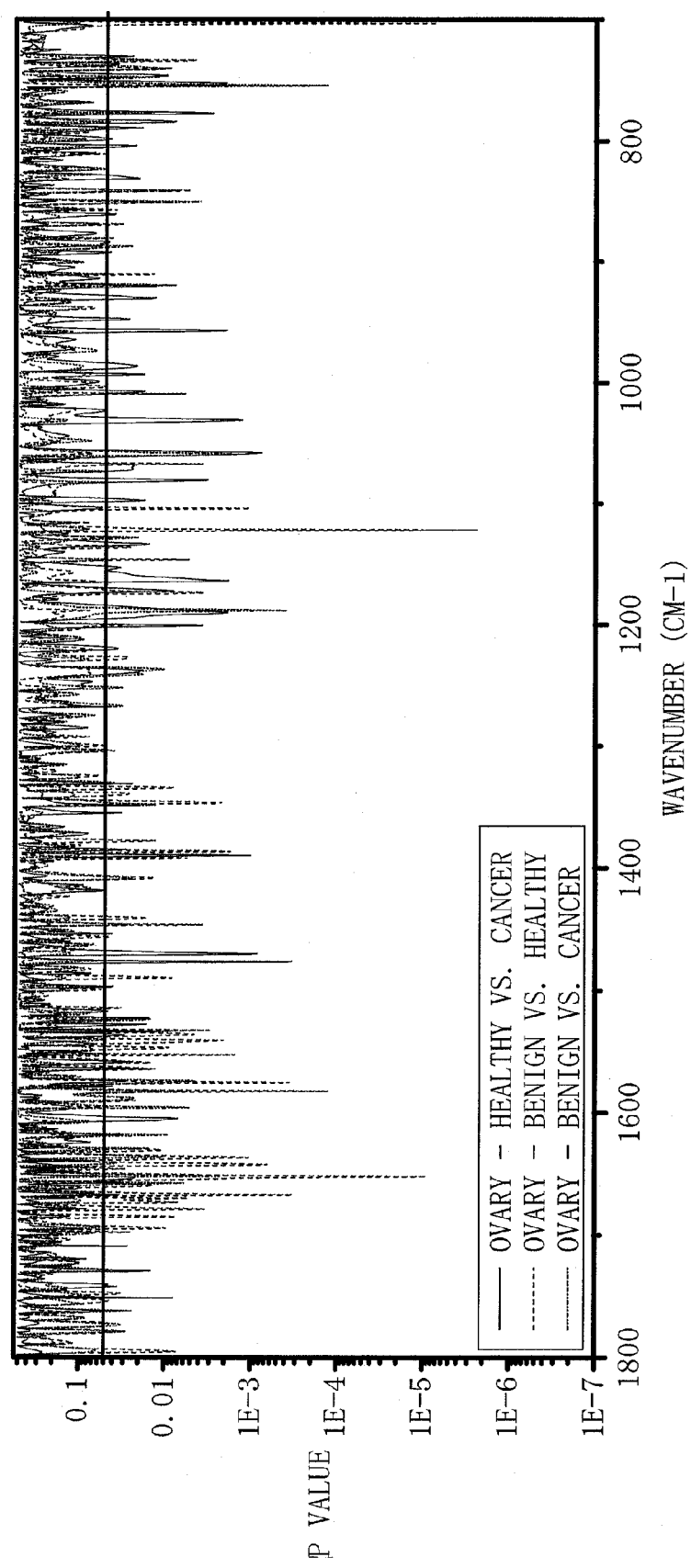

Reference is made to FIGS. 10D-E, which are graphs representing values of the second derivative of absorption spectra of PBMC samples presented in FIGS. 10B-C. Statistical analysis was performed and P-values are provided.

FIG. 10D shows statistical analysis and P-values for gynecological cancer patients compared to pregnant women and to healthy controls. As shown,
  a) The second derivative of PBMC samples from the gynecological cancer patients differed significantly from the second derivative analysis of FTIR-MSP spectra from PBMC of healthy controls, and
  b) The second derivative of PBMC samples from the pregnant women differed significantly from the second derivative analysis of FTIR-MSP spectra from the cancer patients.

Table L lists wavenumbers that were identified in the set of experiments as presented in FIG. 10D. Typically, PBMC samples were analyzed by FTIR-MSP techniques using these wavenumbers to distinguish between: a) control and gynecological cancer patients; and b) gynecological cancer patients and pregnant women. For some applications, the PBMC samples are analyzed by FTIR-MSP at at least one wavenumber selected from Table 1. Alternatively, the PBMC samples are analyzed by FTIR-MSP at at least two or three wavenumbers selected from Table L.

TABLE L

| Healthy Control vs. Cancer Wavenumber (cm-1 ± 4) | | | CS (pregnant) vs. Cancer Wavenumber (cm-1 ± 4) | | |
|---|---|---|---|---|---|
| 706.3 | 1102.6 | 1458.4 | 750.2 | 1061.1 | 1538.9 |
| 752.6 | 1117.1 | 1464.2 | 755.5 | 1139.2 | 1544.7 |
| 767.5 | 1134.9 | 1496.5 | 789.2 | 1167.7 | 1558.2 |
| 776.7 | 1161.4 | 1523.0 | 795.0 | 1178.8 | 1564.0 |
| 784.9 | 1170.1 | 1535.1 | 806.6 | 1185.0 | 1595.3 |
| 798.4 | 1186.5 | 1558.7 | 811.9 | 1221.7 | 1605.4 |
| 804.2 | 1201.0 | 1564.0 | 820.6 | 1240.0 | 1610.8 |
| 877.5 | 1219.3 | 1574.6 | 828.8 | 1261.7 | 1615.1 |
| 883.2 | 1228.4 | 1605.4 | 843.2 | 1328.7 | 1629.1 |
| 920.4 | 1237.1 | 1618.0 | 848.5 | 1385.6 | 1634.4 |
| 927.6 | 1247.7 | 1624.3 | 891.0 | 1403.4 | 1645.0 |
| 955.6 | 1265.6 | 1632.4 | 900.1 | 1436.2 | 1653.2 |
| 985.4 | 1274.7 | 1638.7 | 919.4 | 1486.8 | 1684.5 |
| 998.5 | 1305.6 | 1647.9 | 935.8 | 1497.9 | 1690.8 |
| 1008.6 | 1348.5 | 1653.7 | 994.6 | 1501.3 | 1783.4 |
| 1030.3 | 1365.4 | 1669.6 | 1000.9 | 1506.6 | 1789.1 |

TABLE L-continued

| Healthy Control vs. Cancer Wavenumber (cm-1 ± 4) | | | CS (pregnant) vs. Cancer Wavenumber (cm-1 ± 4) | |
|---|---|---|---|---|
| 1036.6 | 1370.7 | 1678.2 | 1006.2 | 1512.4 |
| 1058.2 | 1384.2 | 1684.5 | 1034.1 | 1527.3 |
| 1067.9 | 1389.5 | 1728.9 | 1048.6 | 1533.1 |
| 1081.9 | 1414.0 | 1783.4 | | |
| 1095.9 | 1452.1 | | | |

For some applications, one, two, three, or more of the following wavenumbers selected from Table L are used to differentiate between the healthy controls and gynecological cancer patients: 1030.3±4 cm-1, 1067.9±4 cm-1, 1134.9±4 cm-1, 1161.4±4 cm-1, 1186.5±4 cm-1, and 1389.5±4 cm-1.

For some applications, one, two, three, or more of the following wavenumbers selected from Table L are used to differentiate between the pregnant women and gynecological cancer patients: 750.2±4 cm-1, 843.2±4 cm-1, 1034.1±4 cm-1, 1048.6±4 cm-1, 1185.0±4 cm-1, 1506.6±4 cm-1.

FIG. 10E shows statistical analysis and p-values for ovarian cancer patients, subjects with benign ovarian tumors and healthy controls. As shown,
  a) The second derivative of PBMC samples from the ovarian cancer patients differed significantly from the second derivative analysis of FTTR-MSP spectra from PBMC of healthy controls,
  b) The second derivative of PBMC samples from healthy controls differed significantly from the second derivative analysis of FTIR-MSP spectra from the subjects with benign a ovarian tumor, and
  c) The second derivative of PBMC samples from ovarian cancer patients differed significantly from the second derivative analysis of FTIR-MSP spectra from the subjects with a benign ovarian tumor.

Table M lists wavenumbers that were identified in the set of experiments as presented in FIG. 10E. Typically, PBMC samples were analyzed by FTIR-MSP techniques using these wavenumbers to distinguish between: a) healthy control and ovarian cancer patients; and b) ovarian cancer patients and subjects with a benign ovarian tumor, and c) healthy control and subjects with a benign ovarian tumor. For some applications, the PBMC samples are analyzed by FTIR-MSP at at least one wavenumber selected from Table M. Alternatively, the PBMC samples are analyzed by FTIR-MSP at at least two or three wavenumbers selected from Table M.

TABLE M

| Healthy control vs. Cancer Wavenumber (cm-1 ± 4) | | | Healthy control vs. Benign Wavenumber (cm-1 ± 4) | | | Benign vs. Cancer Wavenumber (cm-1 ± 4) | |
|---|---|---|---|---|---|---|---|
| 745.4 | 1096.3 | 1536.0 | 702.9 | 1228.0 | 1558.2 | 733.3 | 1408.3 |
| 752.1 | 1133.0 | 1558.2 | 733.8 | 1303.6 | 1563.5 | 740.0 | 1445.9 |
| 776.2 | 1162.4 | 1564.0 | 740.5 | 1333.5 | 1575.6 | 747.3 | 1523.5 |
| 783.4 | 1171.5 | 1574.1 | 754.0 | 1338.8 | 1582.3 | 753.5 | 1540.4 |
| 788.7 | 1188.4 | 1604.5 | 840.8 | 1346.1 | 1588.6 | 840.8 | 1551.9 |
| 797.9 | 1200.5 | 1618.0 | 850.5 | 1376.9 | 1630.0 | 850.5 | 1574.1 |
| 804.2 | 1219.8 | 1653.2 | 868.3 | 1391.9 | 1635.8 | 887.1 | 1582.8 |
| 829.2 | 1238.6 | 1666.7 | 880.3 | 1407.8 | 1642.1 | 909.8 | 1588.6 |
| 919.9 | 1330.6 | 1728.9 | 909.8 | 1440.1 | 1651.7 | 918.9 | 1595.8 |
| 929.5 | 1348.5 | 1740.9 | 1002.8 | 1445.9 | 1666.7 | 1058.7 | 1618.0 |
| 946.9 | 1354.7 | 1751.0 | 1008.6 | 1456.0 | 1678.2 | 1073.7 | 1629.1 |
| 956.5 | 1384.6 | | 1066.4 | 1489.3 | 1685.0 | 1127.7 | 1635.8 |
| 985.4 | 1389.5 | | 1103.6 | 1514.3 | 1694.2 | 1146.5 | 1641.1 |
| 992.2 | 1418.4 | | 1121.4 | 1524.0 | 1747.7 | 1187.9 | 1651.7 |
| 1007.1 | 1468.5 | | 1128.2 | 1532.2 | 1753.5 | 1237.1 | 1657.5 |
| 1029.8 | 1476.2 | | 1135.5 | 1535.5 | 1771.8 | 1252.1 | 1728.4 |
| 1057.8 | 1497.0 | | 1146.0 | 1540.8 | 1778.5 | 1266.5 | 1761.7 |

TABLE M-continued

| Healthy control vs. Cancer Wavenumber (cm-1 ± 4) | | Healthy control vs. Benign Wavenumber (cm-1 ± 4) | | | Benign vs. Cancer Wavenumber (cm-1 ± 4) | |
|---|---|---|---|---|---|---|
| 1068.4 | 1522.0 | 1173.5 | 1546.6 | 1794.4 | 1329.7 | 1773.2 |
| 1080.4 | 1532.6 | 1199.5 | 1552.4 |  | 1347.5 | 1778.5 |

For some applications, one, two, three, or more of the following wavenumbers selected from Table M are used to differentiate between the healthy controls and ovarian cancer patients: 752.1±4 cm-1, 956.5±4 cm-1, 1029.8±4 cm-1, 1057.8±4 cm-1, 1162.4±4 cm-1, 1389.5±4 cm-1, and 1476.2±4 cm-1.

For some applications, one, two, three, or more of the following wavenumbers selected from Table M are used to differentiate between the healthy controls and subjects with a benign ovarian tumor: 754.0±4 cm-1, 1103.6±4 cm-1, 1121.4±4 cm-1, 1346.1±4 cm-1, and 1376.9±4 cm-1.

For some applications, one, two, three, or more of the following wavenumbers selected from Table M are used to differentiate between the subjects with a benign ovarian tumor and the ovarian cancer patients: 753.50±4 cm-1, 850.5±4 cm-1, 918.9±4 cm-1, 1058.7±4 cm-1, 1187.9±4 cm-1 and 1651.7±4 cm-1.

Example 6

In a set of experiments, differential diagnosis of various types of malignant tumors in gynecological tissue was performed based on a FTIR-MSP spectral pattern at selected wavenumbers of plasma samples. Additionally, differential diagnosis of malignant ovarian tumors and benign ovarian tumors was performed based on a FTIR-MSP spectral pattern at selected wavenumbers of plasma samples. Patient data is presented hereinabove in Table B. As mentioned hereinabove, an additional control group for this set of experiments consisted of pregnant women (n=11). Pregnancy may trigger a false positive cancer diagnosis due to physiological changes, thus acting as an appropriate control for gynecological tumors.

In accordance with applications of the present invention, plasma samples from 28 healthy controls were analyzed by FTIR-MSP, and a typical FTIR-MSP spectral pattern was established for control plasma. Additionally, plasma samples from 11 ovarian cancer patients, 15 endometrial cancer patients, 6 gynecological sarcoma patients, 7 cervical cancer patients, 4 vulvar cancer patients and 3 patients diagnosed with a borderline ovarian tumor (BOT) were subjected to FTIR-MSP analysis and compared to the control FTIR-MSP spectral pattern. Additionally, plasma samples from 8 subjects with a benign tumor in ovarian tissue were subjected to FTIR-MSP analysis and compared to the control FTIR-MSP spectral pattern and to the cancer FTIR-MSP spectral pattern. Further additionally, plasma samples from 11 pregnant women were subjected to FTIR-MSP analysis and compared to the control FTIR-MSP spectral pattern, to the cancer FTIR-MSP spectral pattern and to the benign FTIR-MSP spectral pattern.

The plasma samples were obtained by preliminary processing of the peripheral blood in accordance with the protocols described hereinabove with reference to extraction of plasma. The plasma samples were then analyzed by FTIR-MSP, in accordance with the protocols described hereinabove with reference to FTIR-MSP.

Results are presented in FIGS. 11A-E, which are graphs representing FTIR absorption spectra, the second derivative of the absorption spectra, and analysis thereof, based on plasma samples from the gynecological cancer patients, subjects with benign gynecological tumors, pregnant subjects and healthy controls, derived in accordance with some applications of the present invention.

Figure 11A:
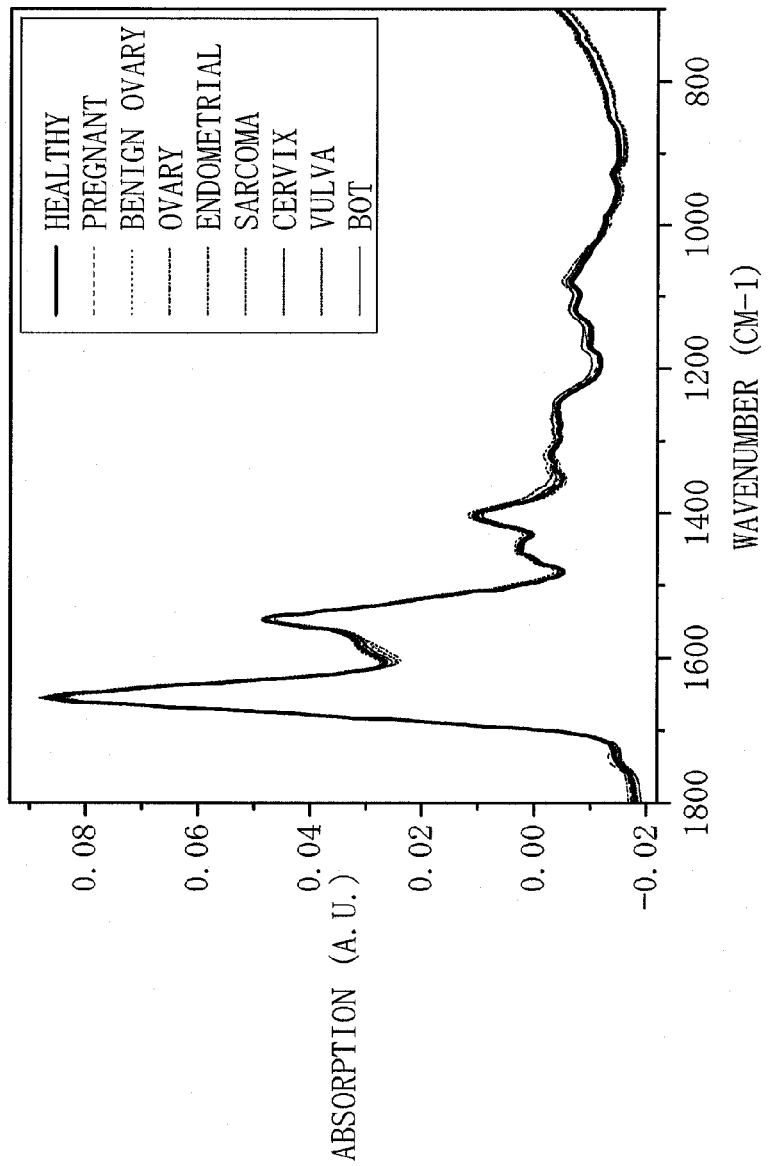
FIGS. 11A-E are graphs representing FTIR absorption spectra, the second derivative of the absorption spectra and analysis thereof, based on plasma samples from: gynecological cancer patients, subjects with benign gynecological tumors, pregnant subjects and healthy controls, derived in accordance with some applications of the present invention.

FIG. 11A shows average FTIR-MSP absorption spectra of plasma samples of healthy controls, subjects with benign ovarian tumors and gynecological cancer patients in the regions of 700-1800 cm-1, after baseline correction and vector normalization. Each spectrum represents the average of five measurements at different sites for each sample. The spectra are composed of several absorption bands, each corresponding to specific functional groups of specific macromolecules such as lipids, proteins, and carbohydrates/nucleic acids. Generally, the FTIR spectrum is typically analyzed by tracking changes in absorption (intensity and/or shift) of these macromolecules.

Figure 11B:
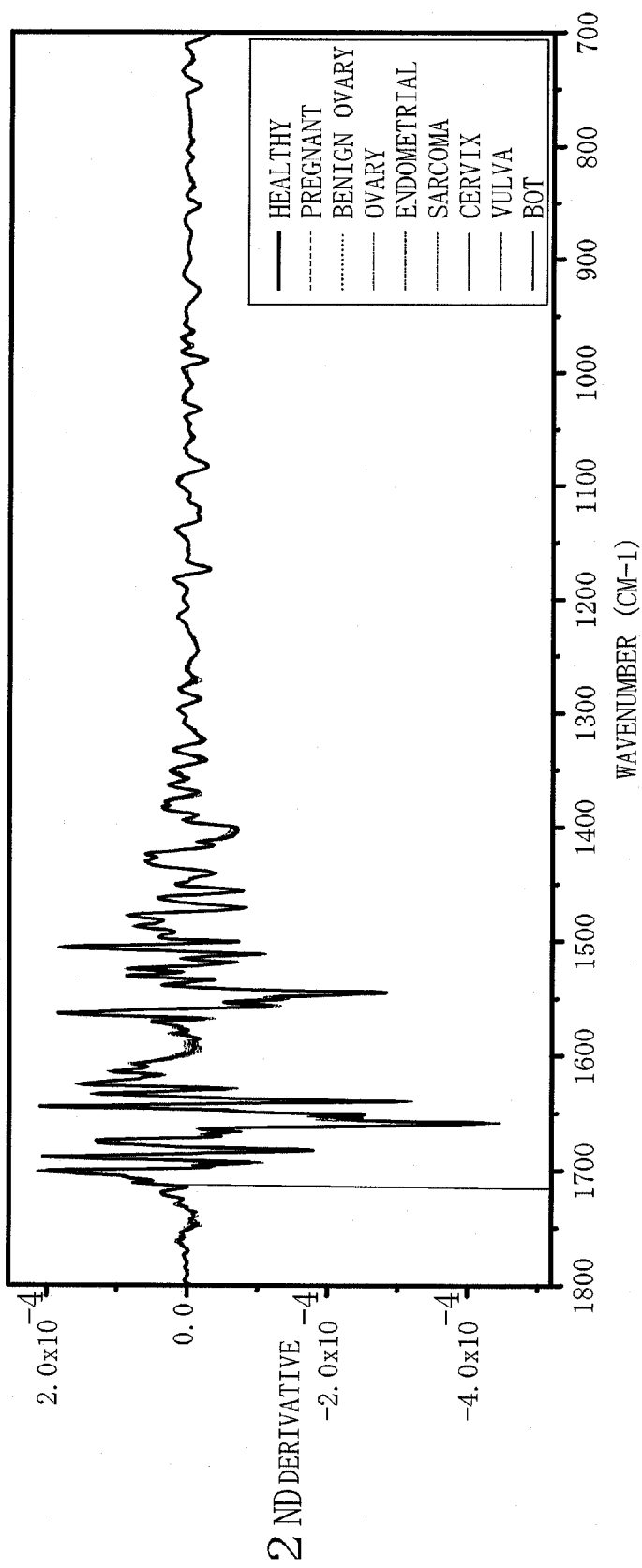
Figure 11C:
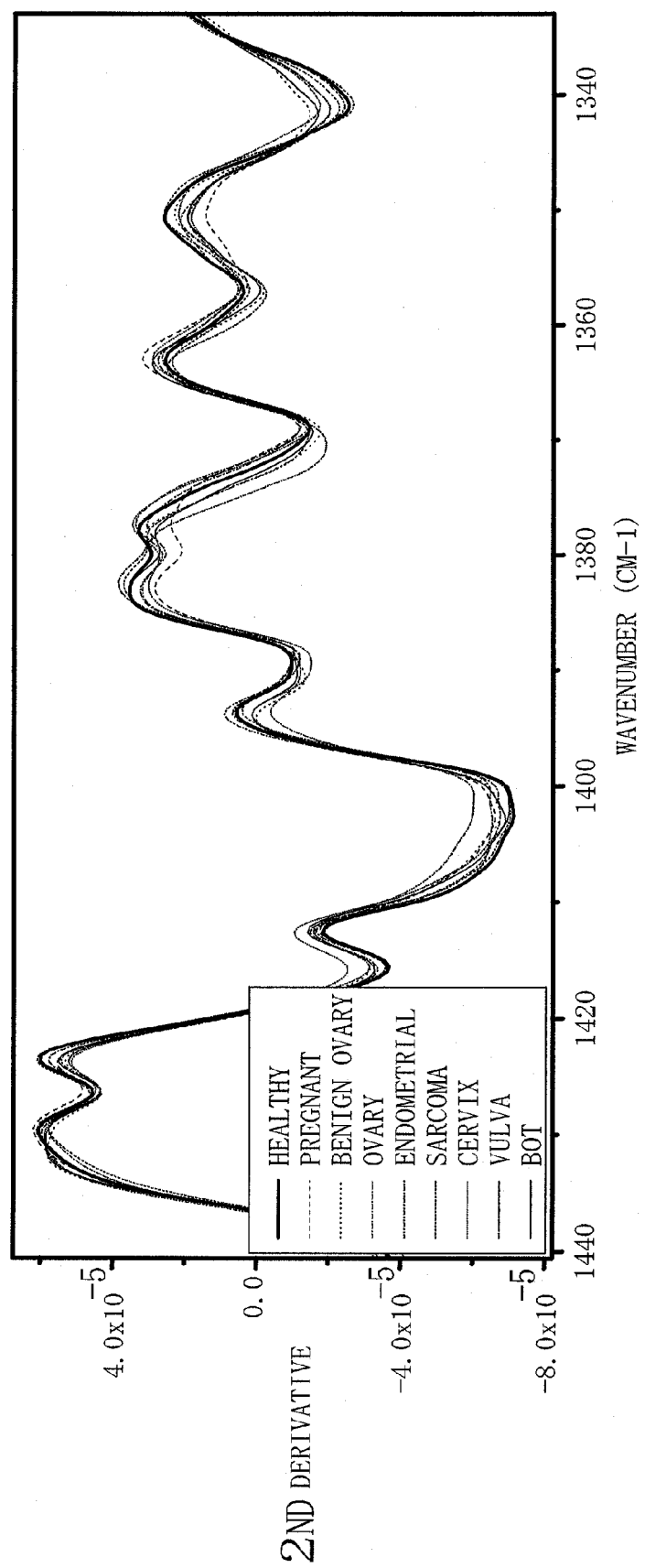

Reference is made to FIGS. 11B-C. In order to achieve effective comparison between the plasma samples of the various gynecological cancer patients, subjects with benign ovarian tumors, pregnant women and the controls, the second derivative of the baseline-corrected, vector-normalized FTIR-MSP spectra was used. Results are presented in FIGS. 11B-C. As shown from the second derivative spectra analysis, the plasma samples from the various cancer patients differed from the control and pregnant women group. Additionally, analysis of plasma by FTIR-MSP of the various cancer patients produced distinct FTIR spectra for each type of gynecological tumor. Accordingly, some applications of the present invention are used to detect a type of a gynecological solid tumor. Typically, each type of malignant gynecological solid tumor produces distinct FTIR spectra of the plasma, which are unique to the type of solid tumor. This can be due to each type of solid tumor inducing specific biochemical changes in plasma.

Figure 11D:
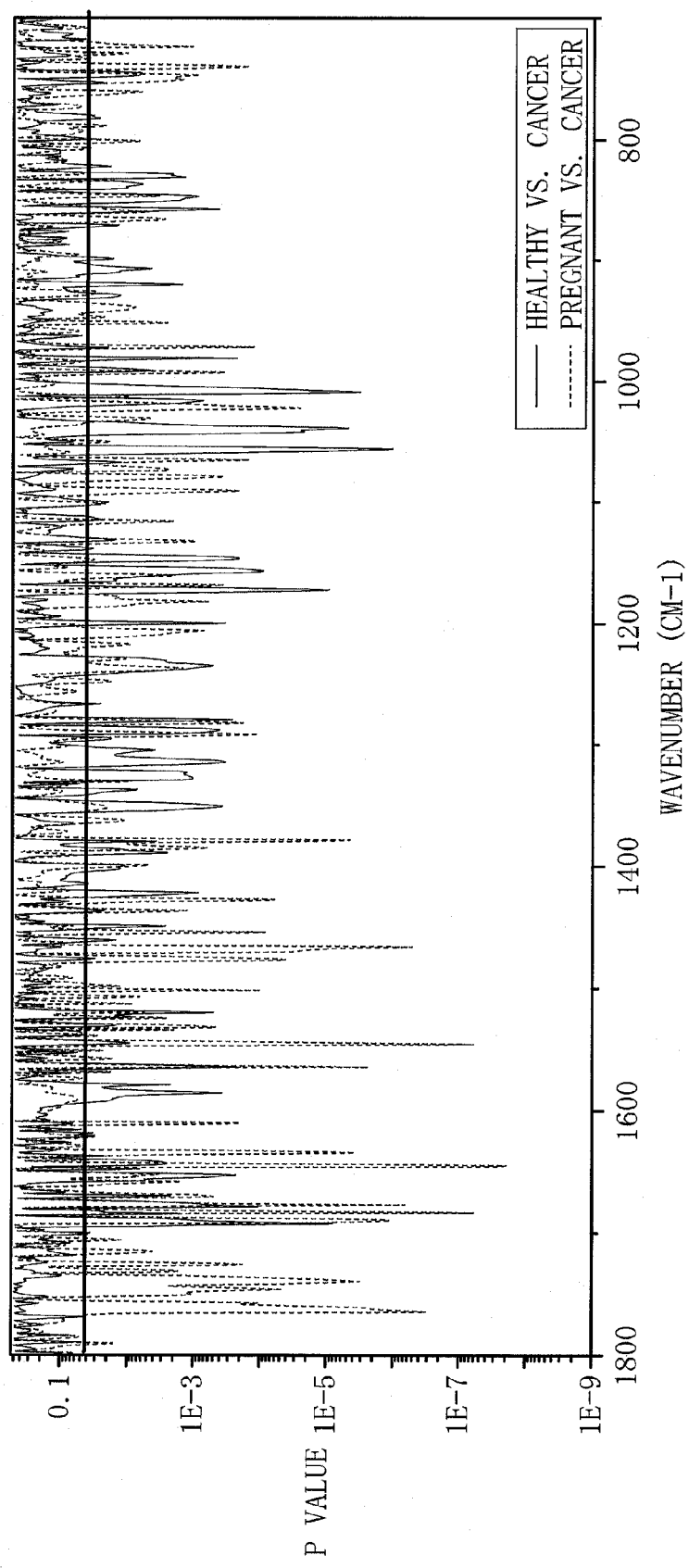
Figure 11E:
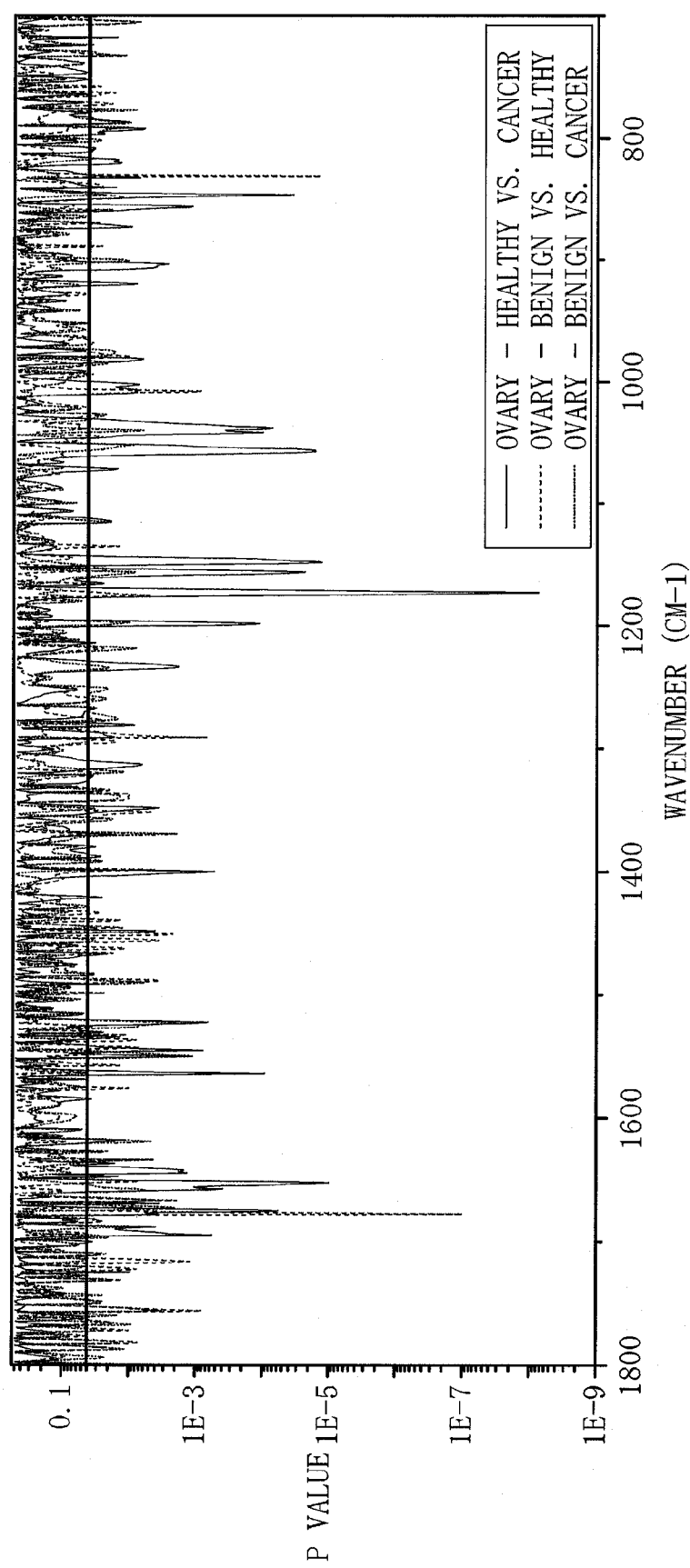

Reference is made to FIGS. 11D-E, which are graphs representing values of the second derivative of absorption spectra of plasma samples presented in FIGS. 11B-C. Statistical analysis was performed and P-values are provided.

FIG. 11D shows statistical analysis and P-values for gynecological cancer patients compared to pregnant women and to healthy controls. As shown,
 a) The second derivative of plasma samples from the gynecological cancer patients differed significantly from the second derivative analysis of FTIR-MSP spectra from plasma of healthy controls, and
 b) The second derivative of plasma samples from the pregnant women differed significantly from the second derivative analysis of FTIR-MSP spectra from the cancer patients.

Table N lists wavenumbers that were identified in the set of experiments as presented in FIG. 11D. Typically, plasma samples were analyzed by FTIR-MSP techniques using these wavenumbers to distinguish between: a) control and gynecological cancer patients; and b) gynecological cancer patients and pregnant women. For some applications, the plasma samples are analyzed by FTIR-MSP at at least one wavenumber selected from Table N. Alternatively, the plasma samples are analyzed by FTIR-MSP at at least two or three wavenumbers selected from Table N.

TABLE N

| Healthy Control vs. Cancer Wavenumber (cm-1 ± 4) | | | CS (pregnant) vs. Cancer Wavenumber (cm-1 ± 4) | | |
|---|---|---|---|---|---|
| 745.4 | 1100.2 | 1413.6 | 729.4 | 1181.2 | 1147.4 |
| 752.6 | 1112.7 | 1421.8 | 740.0 | 1205.8 | 1160.0 |
| 781.5 | 1130.1 | 1435.7 | 749.2 | 1217.3 | 1168.2 |
| 821.5 | 1137.8 | 1449.2 | 760.8 | 1237.1 | 1523.5 |
| 830.2 | 1145.5 | 1460.3 | 800.8 | 1246.8 | 1530.2 |
| 836.5 | 1156.1 | 1475.3 | 846.1 | 1281.5 | 1545.7 |
| 846.6 | 1171.5 | 1519.2 | 859.1 | 1291.1 | 1557.2 |
| 856.7 | 1199.0 | 1529.3 | 864.9 | 1329.7 | 1564.0 |
| 870.2 | 1233.7 | 1544.7 | 926.6 | 1350.9 | 1610.3 |
| 898.2 | 1266.0 | 1564.0 | 938.2 | 1362.0 | 1621.4 |
| 906.4 | 1279.5 | 1578.5 | 951.2 | 1378.4 | 1634.4 |
| 919.4 | 1287.7 | 1585.2 | 971.0 | 1399.1 | 1644.5 |
| 928.6 | 1294.5 | 1620.4 | 992.2 | 1427.5 | 1652.7 |
| 971.5 | 1304.1 | 1642.1 | 1012.0 | 1436.2 | 1658.5 |
| 980.1 | 1313.8 | 1647.4 | 1019.7 | 1453.6 | 1669.1 |
| 989.8 | 1324.9 | 1653.7 | 1030.3 | 1466.1 | 1676.8 |
| 1007.6 | 1336.4 | 1669.6 | 1049.6 | 1475.3 | 1683.1 |
| 1015.3 | 1349.9 | 1676.3 | 1064.5 | 1496.5 | 1689.3 |
| 1038.0 | 1378.9 | 1684.0 | 1071.7 | 1501.3 | 1714.9 |
| 1055.4 | 1388.0 | 1691.7 | 1079.5 | 1506.6 | 1725.5 |
| 1066.4 | 1401.5 | 1699.9 | 1091.0 | 1512.4 | 1730.8 |
| | | | 1101.2 | 1519.6 | 1739.0 |
| | | | 1115.1 | 1131.5 | 1764.1 |

For some applications, one, two, three, or more of the following wavenumbers selected from Table N are used to differentiate between the healthy controls and gynecological cancer patients: 980.1±4 cm-1, 1007.6±4 cm-1, 1038.0±4 cm-1, 1055.4±4 cm-1, 1171.5±4 cm-1, and 1279.5±4 cm-1.

For some applications, one, two, three, or more of the following wavenumbers selected from Table N are used to differentiate between the pregnant women and gynecological cancer patients: 740.0±4 cm-1, 971.0±4 cm-1, 1019.7±4 cm-1, 1064.5±4 cm-1, 1291.1±4 cm-1, 1378.4±4 cm-1.

FIG. 11E shows statistical analysis and p-values for ovarian cancer patients, subjects with benign ovarian tumors and healthy controls. As shown, a) The second derivative of the FTIR-MSP spectra of plasma samples from the ovarian cancer patients differed significantly from the second derivative of FTIR-MSP spectra from plasma of healthy controls, b) The second derivative of the FTIR-MSP spectra of plasma samples from healthy controls differed significantly from the second derivative of FTIR-MSP spectra from the subjects with benign a ovarian tumor, and c) The second derivative of the FTIR-MSP spectra of plasma samples from ovarian cancer patients differed significantly from the second derivative of FTIR-MSP spectra from the subjects with a benign ovarian tumor.

Table O lists wavenumbers that were identified in the set of experiments as presented in FIG. 11E. Typically, plasma samples were analyzed by FTIR-MSP techniques using these wavenumbers to distinguish between: a) healthy control and ovarian cancer patients; and b) ovarian cancer patients and subjects with a benign ovarian tumor, and c) healthy control and subjects with a benign ovarian tumor. For some applications, the plasma samples are analyzed by FTIR-MSP at at least one wavenumber selected from Table O. Alternatively, the plasma samples are analyzed by FTIR-MSP at at least two or three wavenumbers selected from Table O.

TABLE O

| Healthy control vs. Cancer Wavenumber (cm-1 ± 4) | | | Healthy control vs. Benign Wavenumber (cm-1 ± 4) | | Benign vs. Cancer Wavenumber (cm-1 ± 4) | |
|---|---|---|---|---|---|---|
| 717.9 | 1146.5 | 1642.1 | 732.3 | 1432.9 | 705.3 | 1339.3 |
| 724.1 | 1156.6 | 1653.2 | 763.7 | 1450.7 | 731.9 | 1357.6 |
| 746.3 | 1172.5 | 1675.4 | 771.9 | 1456.0 | 777.2 | 1369.2 |
| 751.6 | 1198.1 | 1692.2 | 777.2 | 1461.8 | 787.3 | 1391.4 |
| 764.2 | 1233.3 | 1700.4 | 830.7 | 1488.8 | 809.5 | 1456.5 |
| 786.3 | 1269.9 | 1724.5 | 838.4 | 1537.0 | 846.6 | 1490.2 |
| 792.6 | 1281.0 | 1761.2 | 849.0 | 1543.3 | 900.6 | 1522.5 |
| 809.0 | 1288.2 | | 979.2 | 1557.2 | 967.1 | 1549.0 |
| 818.2 | 1312.8 | | 1007.6 | 1576.0 | 975.8 | 1618.9 |
| 832.1 | 1323.9 | | 1026.9 | 1633.9 | 984.5 | 1634.4 |
| 839.8 | 1348.0 | | 1045.7 | 1651.7 | 1028.4 | 1658.5 |
| 846.6 | 1379.8 | | 1134.4 | 1666.7 | 1039.4 | 1666.7 |
| 856.7 | 1386.1 | | 1153.2 | 1671.0 | 1052.5 | 1673.4 |
| 873.1 | 1400.1 | | 1174.4 | 1676.8 | 1114.2 | 1688.4 |
| 904.0 | 1448.8 | | 1218.3 | 1716.3 | 1156.1 | 1696.6 |
| 919.4 | 1467.1 | | 1259.8 | 1722.1 | 1197.1 | 1710.6 |
| 981.1 | 1522.0 | | 1276.6 | 1730.8 | 1218.3 | 1731.3 |
| 1001.4 | 1529.8 | | 1290.1 | 1748.6 | 1234.2 | 1743.3 |
| 1007.1 | 1544.7 | | 1320.5 | 1754.9 | 1258.8 | 1755.4 |
| 1036.6 | 1550.5 | | 1337.4 | 1765.5 | 1274.7 | 1767.4 |
| 1056.8 | 1563.5 | | 1351.4 | 1771.8 | 1293.5 | 1771.8 |
| 1072.2 | 1584.7 | | 1391.4 | 1781.9 | 1318.6 | 1781.9 |
| 1113.7 | 1618.0 | | 1398.6 | | 1333.1 | 1786.2 |

For some applications, one, two, three, or more of the following wavenumbers selected from Table O are used to differentiate between the healthy controls and ovarian cancer patients: 846.6±4 cm-1, 1056.8±4 cm-1, 1146.5±4 cm-1, 1156.6±4 cm-1, 1172.5±4 cm-1, 1198.1±4 cm-1.

For some applications, one, two, three, or more of the following wavenumbers selected from Table O are used to differentiate between the healthy controls and subjects with a benign ovarian tumor: 830.7±4 cm-1, 1007.6±4 cm-1, 1290.1±4 cm-1, 1676.8±4 cm-1, 1716.3±4 cm-1, and 1754.9±4 cm-1.

For some applications, one, two, three, or more of the following wavenumbers selected from Table O are used to differentiate between the subjects with a benign ovarian tumor and the ovarian cancer patients: 777.2±4 cm-1, 1039.4±4 cm-1, 1052.5±4 cm-1, 1156.1±4 cm-1, 1218.3±4 cm-1 and 1369.2±4 cm-1.

Figure 12A:
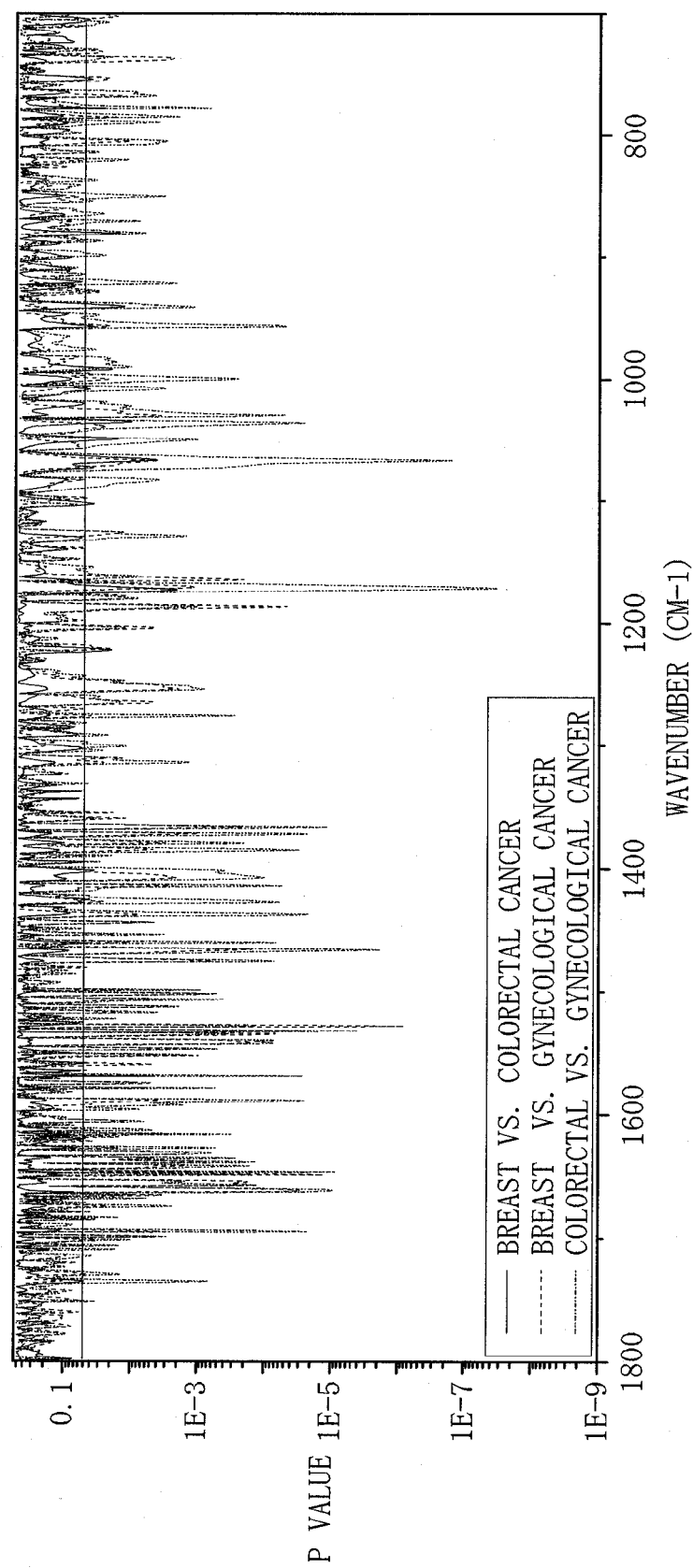
FIGS. 12A-B are graphs representing statistical analysis of FTIR spectra of PBMC and plasma samples from gynecological cancer patients, colorectal cancer patients and breast cancer patients derived in accordance with some applications of the present invention.
Figure 12B:
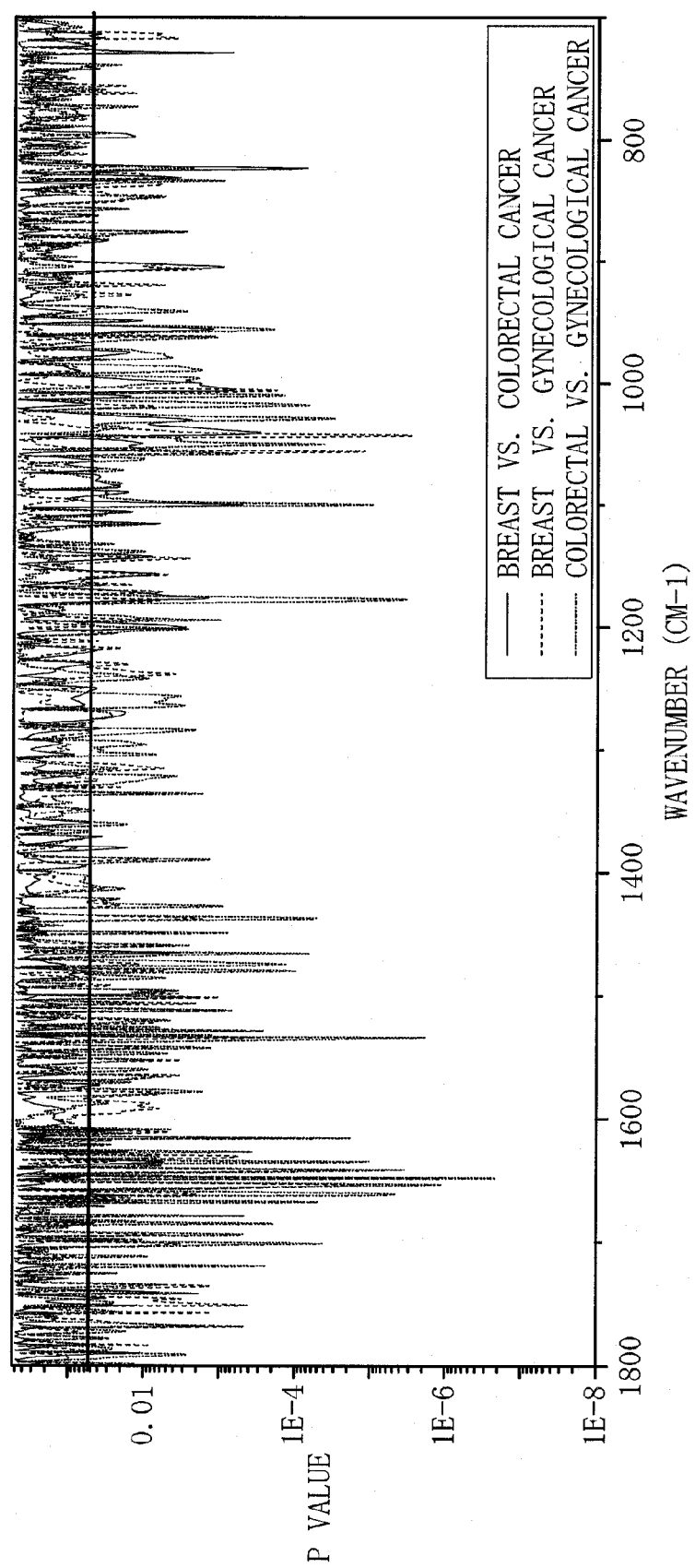

Reference is made to Examples 1-6 and to FIGS. 12A-B. In some applications of the present invention, analysis of PBMC and plasma samples by FTIR-MSP is used to detect a type of solid tumor. Typically, each type of malignant solid tumor produces distinct FTIR spectra of the PBMC and plasma, which are unique to the type of solid tumor.

FIG. 12A shows statistical analysis and p-values of FTIR-MSP spectra obtained from PBMC samples of breast cancer patients, gynecological cancer patients and colorectal cancer patients (GI). As shown, some applications of the present invention distinguish between a) Breast cancer patients and colorectal cancer patients;

b) Breast cancer patients and gynecological cancer patients; and c) Colorectal cancer patients and gynecological cancer patients.

Table P lists wavenumbers that were identified in the set of experiments as presented in FIG. 12A. Typically, PBMC samples were analyzed by FTIR-MSP techniques using these wavenumbers to distinguish between: a) breast cancer patients and colorectal cancer patients; b) breast cancer patients and gynecological cancer patients, and c) colorectal cancer patients and gynecological cancer patients. For some applications, the PBMC samples are analyzed by FTIR-MSP at at least one wavenumber selected from Table P. Alternatively, the PBMC samples are analyzed by FTIR-MSP at at least two or three wavenumbers selected from Table P.

TABLE P

| Breast vs. Colorectal Wavenumber (cm-1 ± 4) | Breast vs. Gynecological Wavenumber (cm-1 ± 4) | | | Colorectal vs. Gynecological Wavenumber (cm-1 ± 4) | | | |
|---|---|---|---|---|---|---|---|
| 704.9 | 731.4 | 1264.6 | 1546.6 | 707.7 | 954.1 | 1303.6 | 1528.3 |
| 753.1 | 737.6 | 1309.4 | 1552.4 | 736.7 | 986.9 | 1313.8 | 1534.6 |
| 879.9 | 753.5 | 1365.4 | 1559.6 | 764.6 | 999.4 | 1365.8 | 1541.3 |
| 939.2 | 767.5 | 1371.1 | 1568.3 | 776.7 | 1008.1 | 1371.6 | 1546.6 |
| 956.0 | 784.9 | 1378.4 | 1574.6 | 783.9 | 1028.4 | 1377.4 | 1551.9 |
| 990.7 | 805.1 | 1384.6 | 1589.1 | 788.7 | 1037.0 | 1384.6 | 1568.3 |
| 1008.1 | 928.1 | 1405.9 | 1605.4 | 806.1 | 1051.5 | 1403.9 | 1574.1 |
| 1035.1 | 955.6 | 1414.0 | 1615.6 | 812.8 | 1067.9 | 1414.0 | 1578.5 |
| 1049.6 | 999.4 | 1427.1 | 1631.0 | 820.1 | 1083.3 | 1425.6 | 1590.0 |
| 1066.0 | 1030.3 | 1437.2 | 1637.3 | 836.5 | 1128.2 | 1435.7 | 1605.0 |
| 1072.7 | 1039.0 | 1452.6 | 1642.1 | 850.0 | 1153.2 | 1443.5 | 1611.7 |
| 1102.6 | 1067.4 | 1458.9 | 1645.5 | 864.0 | 1161.4 | 1453.1 | 1626.7 |
| 1172.5 | 1126.2 | 1465.6 | 1648.4 | 870.2 | 1170.1 | 1459.8 | 1642.1 |
| 1221.2 | 1162.9 | 1474.3 | 1654.6 | 880.3 | 1179.3 | 1467.1 | 1648.4 |
| 1401.5 | 1170.1 | 1501.8 | 1660.9 | 887.1 | 1186.5 | 1474.8 | 1660.4 |
| 1568.8 | 1178.3 | 1506.1 | 1664.7 | 898.2 | 1202.9 | 1498.4 | 1673.9 |
| | 1186.0 | 1511.9 | 1694.6 | 920.4 | 1252.1 | 1501.8 | 1693.7 |
| | 1202.9 | 1528.3 | 1698.5 | 927.6 | 1262.7 | 1507.1 | 1700.9 |
| | 1219.8 | 1532.2 | | 939.6 | 1275.7 | 1512.4 | 1728.4 |
| | 1251.1 | 1540.8 | | 946.4 | 1299.8 | 1516.7 | 1734.7 |

For some applications, one, two, three, or more of the following wavenumbers selected from Table P are used to differentiate between breast cancer patients and colorectal cancer patients: 879.9±4 cm-1, 939.2±4 cm-1, 1035.1±4 cm-1, 1066.0±4 cm-1, 1172.5±4 cm-1, 1568.8±4 cm-1.

For some applications, one, two, three, or more of the following wavenumbers selected from Table P are used to differentiate between breast cancer patients and gynecological cancer patients: 1162.9±4 cm-1, 1186.0±4 cm-1, 1251.1±4 cm-1, 1365.4±4 cm-1, 1465.6±4 cm-1, 1528.3±4 cm-1 and 1648.4±4 cm-1.

For some applications, one, two, three, or more of the following wavenumbers selected from Table P are used to differentiate between colorectal cancer patients and gynecological cancer patients: 954.1±4 cm-1, 1037.0±4 cm-1, 1067.9±4 cm-1, 1170.1±4 cm-1, 1365.8±4 cm-1 and 1384.6±4 cm-1.

FIG. 12B shows statistical analysis and P values of FTIR-MSP spectra obtained from plasma samples of breast cancer patients, gynecological cancer patients and colorectal cancer patients (GI). As shown, some applications of the present invention distinguish between a) Breast cancer patients and colorectal cancer patients;
b) Breast cancer patients and gynecological cancer patients; and
c) Colorectal cancer patients and gynecological cancer patients.

Table Q lists wavenumbers that were identified in the set of experiments as presented in FIG. 12B. Typically, plasma samples were analyzed by FTIR-MSP techniques using these wavenumbers to distinguish between: a) breast cancer patients and colorectal cancer patients; b) breast cancer patients and gynecological cancer patients, and c) colorectal cancer patients and gynecological cancer patients. For some applications, the plasma samples are analyzed by FTIR-MSP at at least one wavenumber selected from Table Q. Alternatively, the plasma samples are analyzed by FTIR-MSP at at least two or three wavenumbers selected from Table Q.

TABLE Q

| Breast vs. Colorectal Wavenumber (cm-1 ± 4) | | Breast vs. Gynecological Wavenumber (cm-1 ± 4) | | | Colorectal vs. Gynecological Wavenumber (cm-1 ± 4) | | | |
|---|---|---|---|---|---|---|---|---|
| 716.9 | 1115.1 | 715.0 | 1164.8 | 1528.3 | 739.1 | 1116.1 | 1496.5 | 1712.0 |
| 728.5 | 1142.1 | 728.0 | 1171.1 | 1534.6 | 773.3 | 1138.3 | 1501.3 | 1719.7 |
| 742.0 | 1156.1 | 756.0 | 1177.3 | 1552.4 | 795.0 | 1175.9 | 1511.4 | 1734.7 |
| 796.5 | 1174.4 | 762.2 | 1193.7 | 1565.9 | 823.0 | 1193.2 | 1519.6 | 1740.9 |
| 823.0 | 1199.5 | 821.5 | 1204.8 | 1579.4 | 833.6 | 1201.9 | 1528.3 | 1749.1 |
| 831.2 | 1249.6 | 829.2 | 1217.3 | 1587.6 | 847.1 | 1241.9 | 1535.5 | 1756.4 |
| 883.2 | 1271.3 | 836.5 | 1229.9 | 1591.5 | 856.7 | 1257.8 | 1542.3 | 1767.4 |
| 904.5 | 1282.4 | 846.6 | 1238.1 | 1610.8 | 876.0 | 1271.8 | 1552.4 | |
| 948.3 | 1370.7 | 856.7 | 1315.2 | 1615.1 | 940.6 | 1284.8 | 1565.9 | |
| 955.6 | 1379.8 | 876.0 | 1335.9 | 1630.5 | 955.1 | 1295.9 | 1578.0 | |
| 975.3 | 1464.7 | 882.3 | 1388.5 | 1641.1 | 962.3 | 1304.1 | 1587.6 | |
| 1003.8 | 1573.1 | 904.9 | 1412.6 | 1647.9 | 976.8 | 1322.9 | 1615.1 | |
| 1010.5 | 1609.3 | 919.4 | 1421.3 | 1653.7 | 987.9 | 1336.4 | 1626.7 | |
| 1030.8 | 1634.4 | 927.1 | 1436.7 | 1660.9 | 998.5 | 1360.1 | 1631.0 | |
| 1039.0 | 1661.9 | 937.7 | 1448.8 | 1667.6 | 1009.6 | 1389.5 | 1635.3 | |
| 1050.1 | 1666.2 | 948.3 | 1459.4 | 1694.2 | 1017.3 | 1412.1 | 1642.1 | |
| 1070.8 | 1740.4 | 961.3 | 1467.1 | 1701.9 | 1028.4 | 1426.6 | 1647.9 | |
| 1080.4 | 1745.3 | 980.1 | 1473.8 | 1735.1 | 1047.6 | 1437.2 | 1654.1 | |
| 1090.5 | 1751.0 | 1005.2 | 1479.6 | 1748.2 | 1056.8 | 1448.8 | 1659.9 | |
| 1099.7 | 1790.1 | 1018.7 | 1497.0 | 1756.8 | 1062.1 | 1458.9 | 1667.2 | |

TABLE Q-continued

| Breast vs. Colorectal Wavenumber (cm-1 ± 4) | Breast vs. Gynecological Wavenumber (cm-1 ± 4) | | | Colorectal vs. Gynecological Wavenumber (cm-1 ± 4) | | |
|---|---|---|---|---|---|---|
| 1106.0 | 1039.9 | 1501.3 | 1778.0 | 1071.3 | 1466.1 | 1678.7 |
|  | 1055.8 | 1506.1 | 1783.4 | 1082.8 | 1473.3 | 1685.0 |
|  | 1144.1 | 1511.9 |  | 1098.7 | 1479.6 | 1693.7 |
|  | 1157.1 | 1521.1 |  | 1107.4 | 1484.9 | 1701.9 |

For some applications, one, two, three, or more of the following wavenumbers selected from Table Q are used to differentiate between breast cancer patients and colorectal cancer patients: 823.0±4 cm-1, 904.5±4 cm-1, 955.6±4 cm-1, 1003.8±4 cm-1, 1039.0±4 cm-1, 1099.7±4 cm-1, and 1174.4±4 cm-1.

For some applications, one, two, three, or more of the following wavenumbers selected from Table Q are used to differentiate between breast cancer patients and gynecological cancer patients: 961.3±4 cm-1, 1005.2±4 cm-1, 1039.9±4 cm-1, 1055.8±4 cm-1, 1528.3±4 cm-1, and 1647.9±4 cm-1.

For some applications, one, two, three, or more of the following wavenumbers selected from Table Q are used to differentiate between colorectal cancer patients and gynecological cancer patients: 955.1±4 cm-1, 1028.4±4 cm-1, 1047.6±4 cm-1, 1098.7±4 cm-1, 1175.9±4 cm-1 1535.5±4 cm-1, and 1647.9±4 cm-1.

Figure 13A:
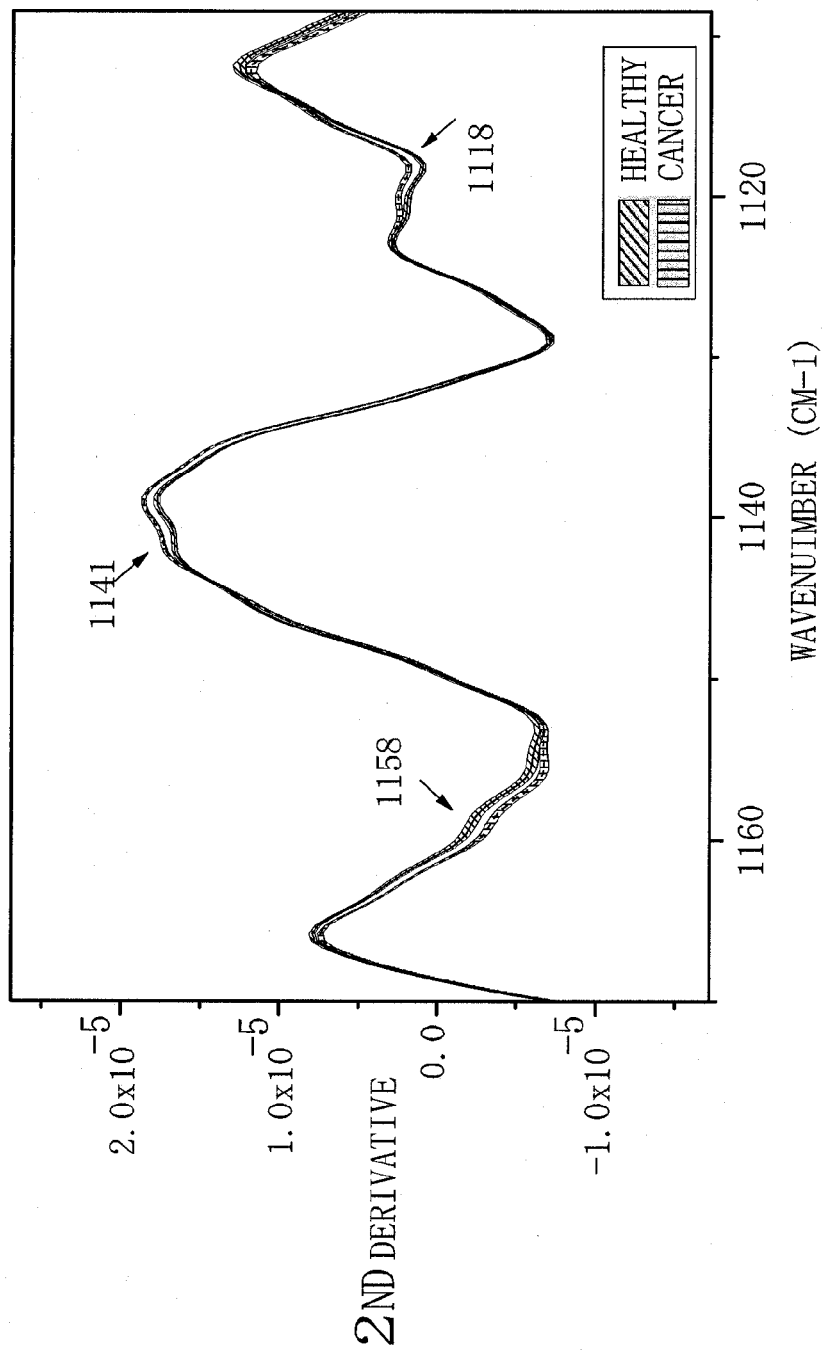
FIGS. 13A-D are graphs representing the second derivative of FTIR absorption spectra, and analysis thereof, based on PBMC and plasma samples from cancer patients and healthy controls, derived in accordance with some applications of the present invention.
Figure 13B:
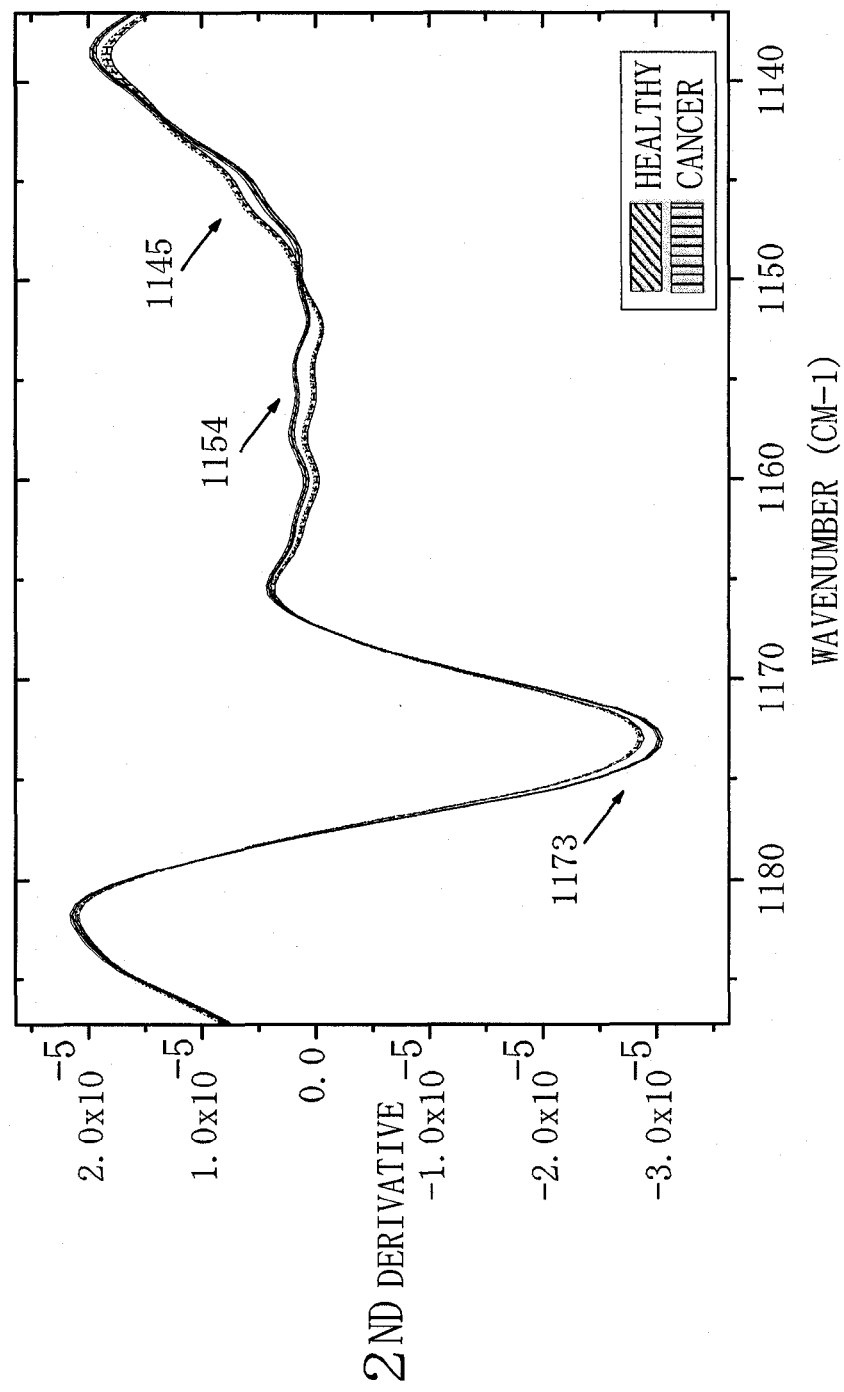
Figure 13C:
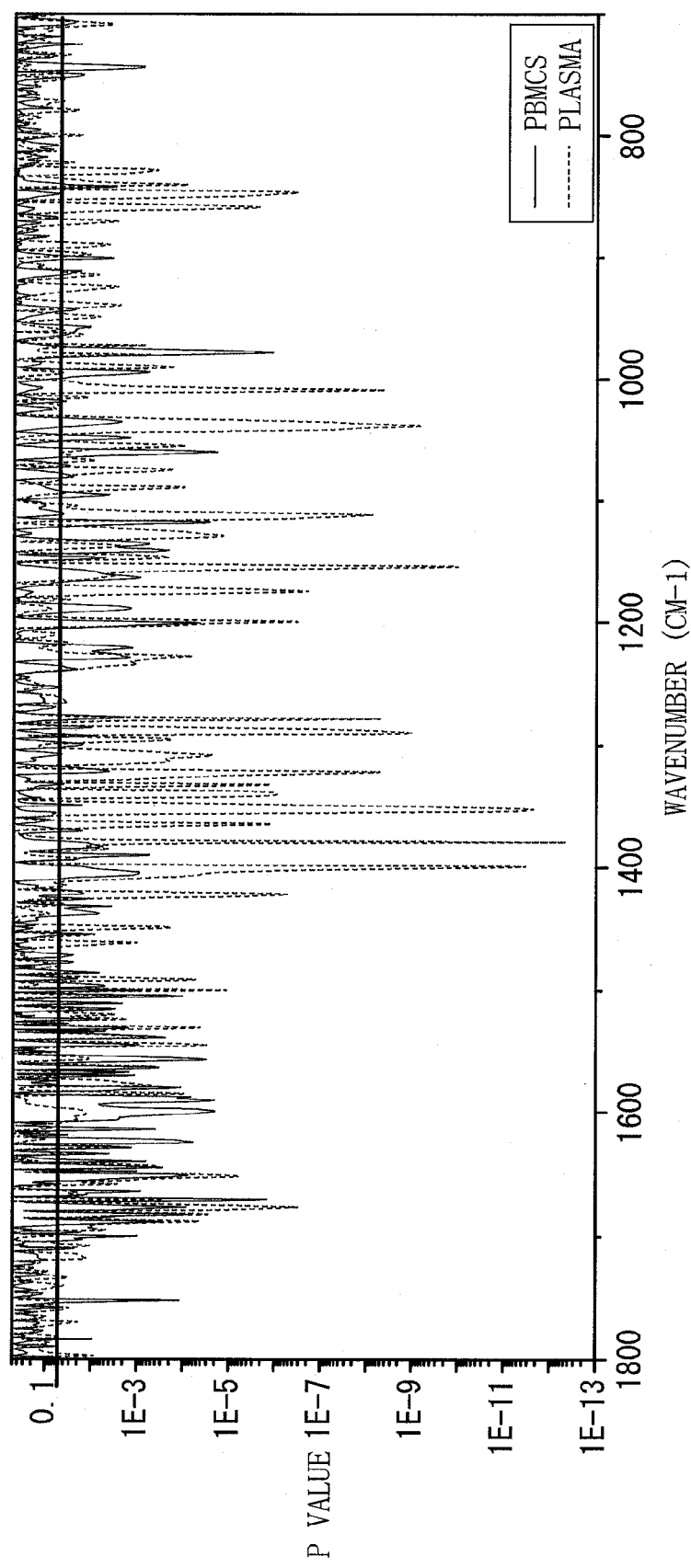
Figure 13D:
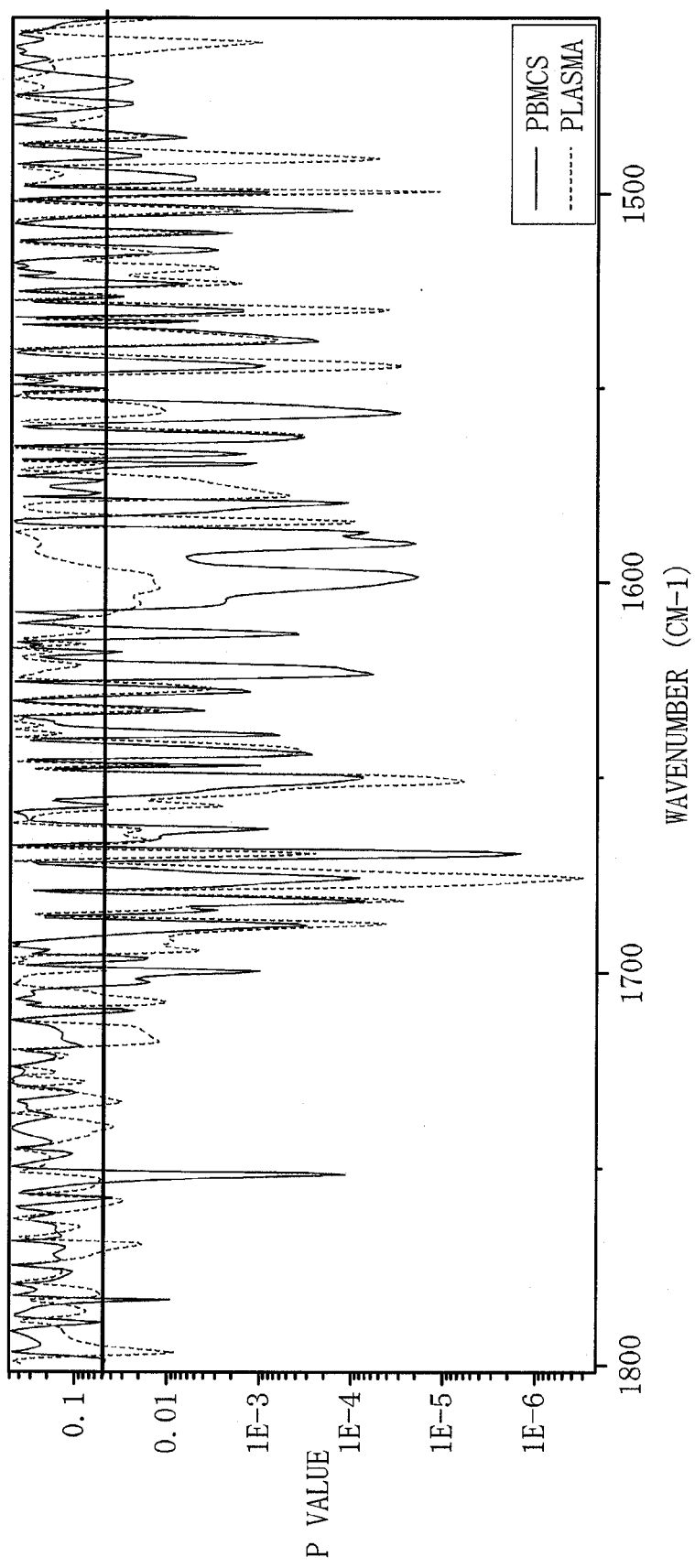

Reference is made to FIGS. 13A-D, which are graphs representing the second derivative of FTIR absorption spectra, and analysis thereof, based on PBMC (FIG. 13A) and plasma (FIG. 13B) samples from cancer patients and healthy controls, derived in accordance with some applications of the present invention. As shown in FIGS. 13A-B, the second derivative spectral analysis shows that PBMC and plasma samples from cancer patients differed from the spectra of healthy control. Main spectral regions are marked.

Table R lists wavenumbers that were identified for diagnosis of cancer using PBMC samples with reference to the set of experiments as presented in FIG. 13A-D.

TABLE R

| Wavenumber (cm-1 ± 4) | | | |
|---|---|---|---|
| 706.3 | 1117.1 | 1420.8 | 1562.5 |
| 742.9 | 1134.9 | 1431.4 | 1566.9 |
| 749.7 | 1146.5 | 1437.2 | 1569.3 |
| 841.8 | 1162.4 | 1453.6 | 1579.4 |
| 900.1 | 1188.4 | 1470.9 | 1587.1 |
| 910.7 | 1200.5 | 1476.7 | 1598.7 |
| 942.5 | 1220.7 | 1485.4 | 1613.6 |
| 956.5 | 1228.1 | 1496.0 | 1623.3 |
| 977.7 | 1276.6 | 1499.4 | 1628.1 |
| 993.6 | 1285.3 | 1504.2 | 1643.1 |
| 1034.1 | 1292.1 | 1510.0 | 1649.8 |
| 1048.1 | 1298.8 | 1514.3 | 1663.3 |
| 1059.7 | 1321.0 | 1523.0 | 1669.6 |
| 1071.3 | 1369.2 | 1529.8 | 1675.8 |
| 1079.0 | 1382.2 | 1538.0 | 1681.6 |
| 1094.9 | 1389.5 | 1544.2 | 1699.5 |
| 1110.3 | 1403.9 | 1555.8 | 1709.6 |

For some applications, one, two, three, or more of the following wavenumbers selected from Table R are used to diagnose cancer using PBMC samples: 749.70±4 cm-1, 841.8±4 cm-1, 993.6±4 cm-1, 1034.1±4 cm-1, 1117.1±4 cm-1, 1146.5±4 cm-1, 1228.1±4 cm-1 and 1276.6±4 cm-1.

Table S lists wavenumbers that were identified for diagnosis of cancer using plasma samples with reference to the set of experiments as presented in FIG. 13A-D.

TABLE S

| 733.3 | 959.4 | 1174.0 | 1399.1 | 1562.5 |
|---|---|---|---|---|
| 748.2 | 963.8 | 1180.7 | 1414.5 | 1577.5 |
| 753.5 | 971.9 | 1199.5 | 1421.3 | 1584.2 |
| 771.4 | 979.7 | 1217.3 | 1429.5 | 1601.6 |
| 779.1 | 989.8 | 1227.5 | 1448.8 | 1627.1 |
| 799.3 | 994.6 | 1233.7 | 1454.1 | 1643.1 |
| 821.5 | 1008.1 | 1263.6 | 1460.8 | 1651.3 |
| 821.5 | 1014.4 | 1278.1 | 1484.9 | 1666.2 |
| 827.8 | 1038.0 | 1289.7 | 1490.7 | 1675.8 |
| 840.3 | 1054.9 | 1295.0 | 1499.4 | 1681.6 |
| 846.6 | 1066.9 | 1307.5 | 1504.2 | 1687.4 |
| 858.6 | 1074.6 | 1321.5 | 1510.0 | 1694.2 |
| 870.2 | 1088.6 | 1331.6 | 1515.3 | 1707.2 |
| 889.0 | 1111.3 | 1339.8 | 1519.2 | 1717.8 |
| 897.2 | 1128.6 | 1352.3 | 1523.0 | 1733.2 |
| 913.6 | 1136.8 | 1364.4 | 1529.8 | 1739.5 |
| 923.7 | 1146.0 | 1378.9 | 1537.5 | 1758.3 |
| 938.7 | 1153.7 | 1384.6 | 1544.2 | 1769.4 |
| 948.3 | 1160.9 | 1392.4 | 1555.8 | |

For some applications, one, two, three, or more of the following wavenumbers selected from Table S are used to diagnose cancer using plasma samples: 846.6±4 cm-1, 1008.1±4 cm-1, 1038.0±4 cm-1, 1111.3±4 cm-1, 1153.7±4 cm-1, 1278.1±4 cm-1, and 1289.7±4 cm-1.

Figure 14A:
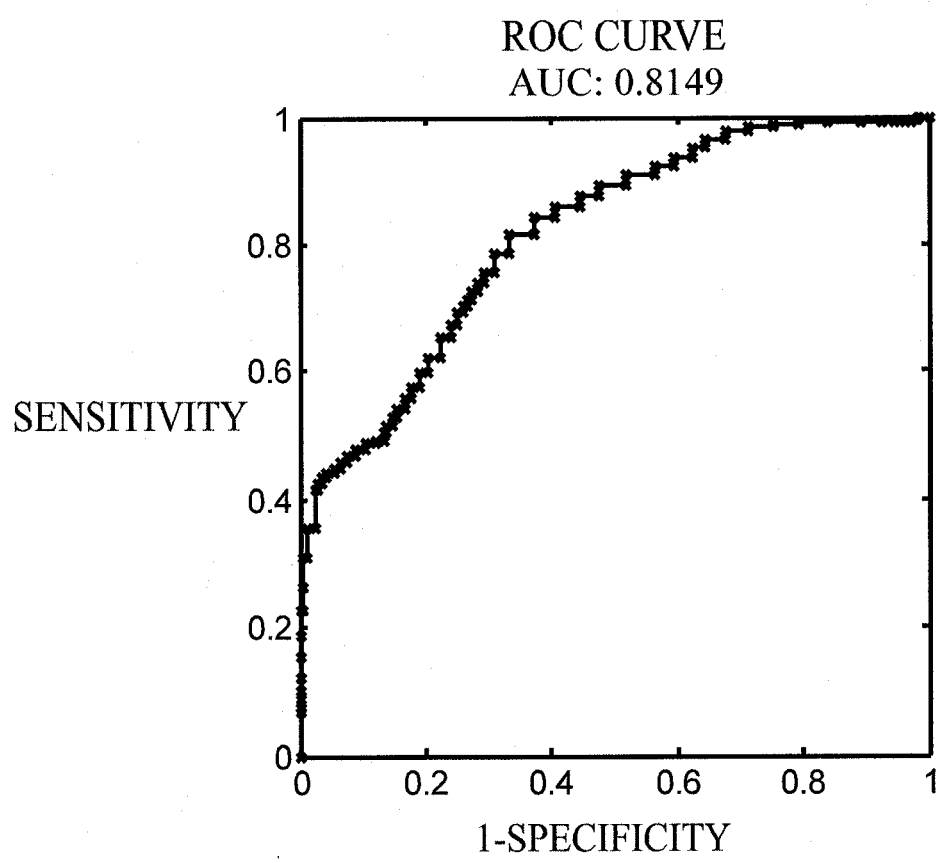
FIGS. 14A-C are graphs representing statistical analysis including receiver operating characteristic (ROC) curve analysis of the FTIR spectra, based on analysis of PBMC and plasma samples from cancer patients and healthy controls, derived in accordance with some applications of the present invention.
Figure 14B:
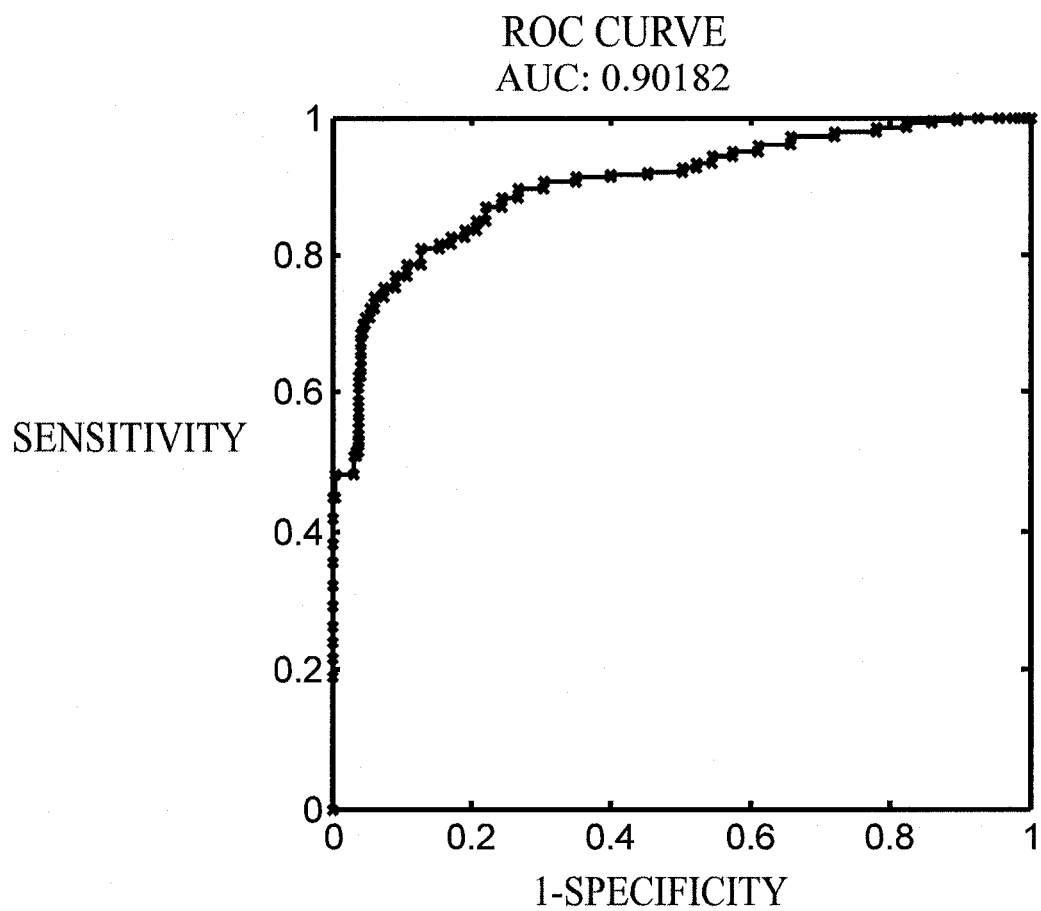
Figure 14C:
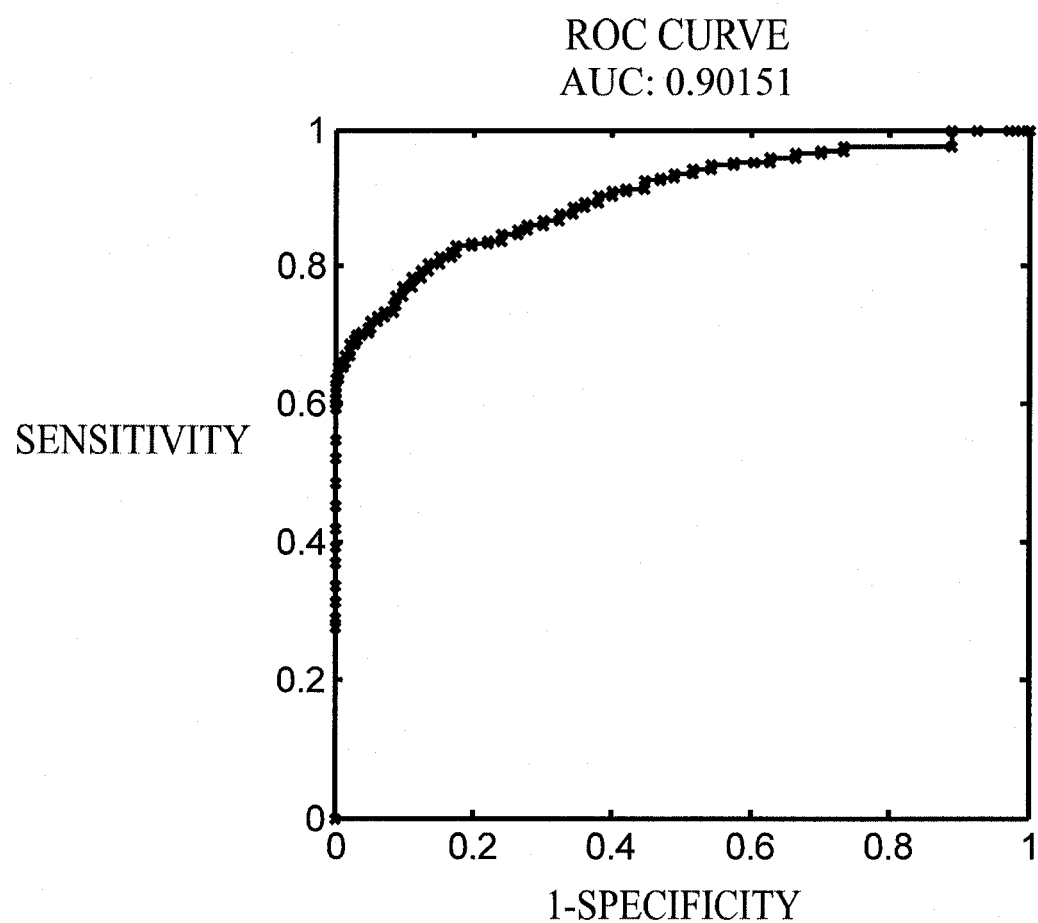

FIGS. 14A-C show receiver operating characteristic (ROC) curve analysis, including the area under the curve (AUC), of PBMC (FIG. 14A) and plasma (FIG. 14B) of healthy controls, compared to the subjects with malignant tumors (cancer patients). As shown, combined use of both the plasma and PBMC samples (FIG. 14C) increased sensitivity and specificity for the diagnosis of cancer.

Figure 15A:
FIGS. 15A-D are schematic illustrations of slides containing a biological sample that was air dried for 0.5 h under laminar flow at a temperature of 30±4 C to remove water in accordance with some applications of the present invention, compared to slides containing a biological sample that was air dried for 0.5 h under laminar flow at a temperature of 21 C to remove water.
Figure 15A:
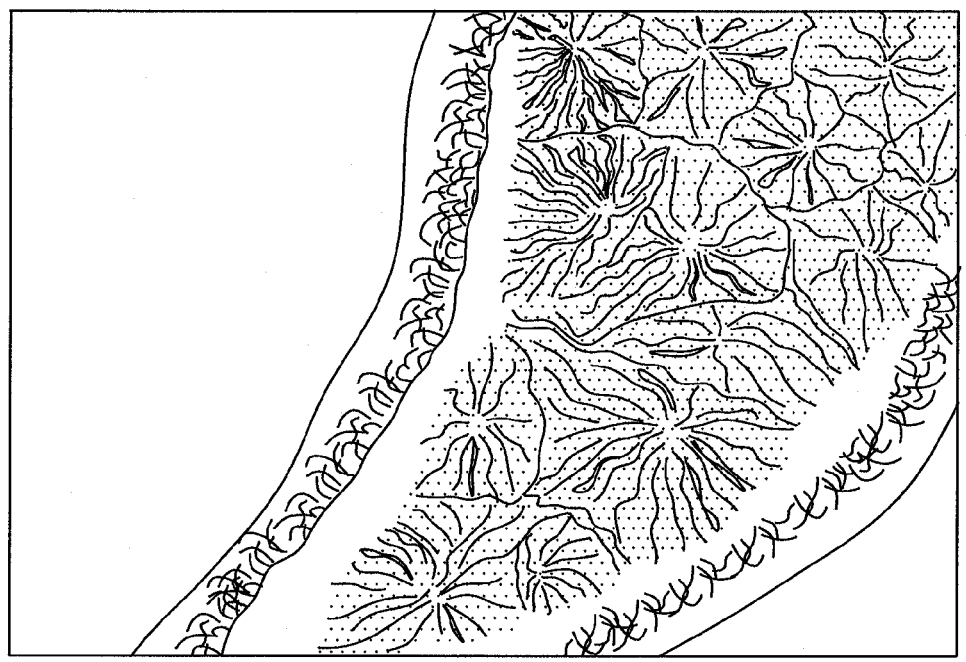
Figure 15B:
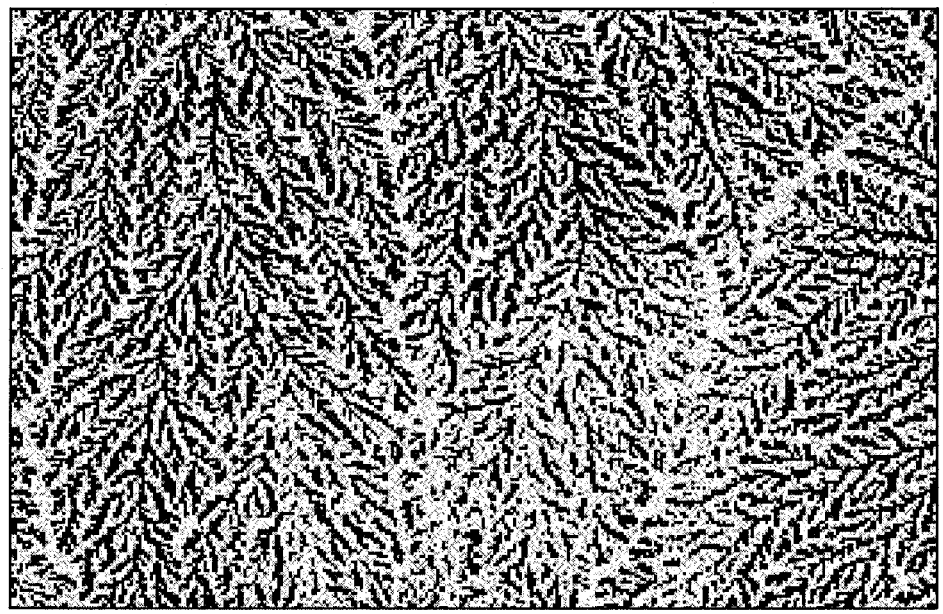
Figure 15C:
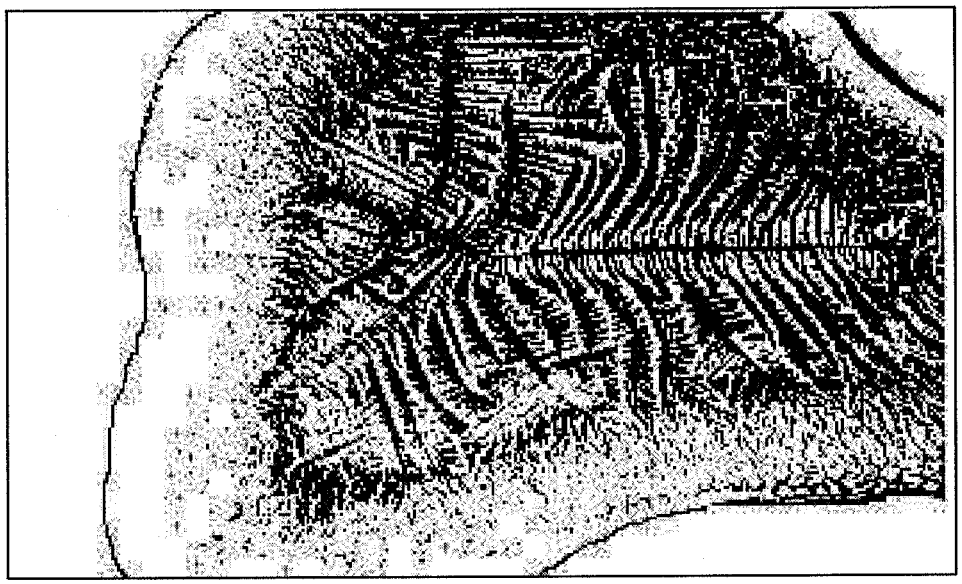
Figure 15D:

FIGS. 15A-D are schematic illustrations of slides containing a biological plasma sample that was air dried for 0.5 h under laminar flow at a temperature of 30±4 C (FIGS. 15A-B) to remove water in accordance with some applications of the present invention, compared to slides containing a biological plasma sample that was air dried for 0.5 h under laminar flow at a temperature of 21 C to remove water (FIG. 15C-D). Results show that drying at a temperature of 30±4 C produces improved slides, for use in applications of the present invention. It is noted that FIGS. 15B and 15D are at the same microscopic zoom level and are an enlarged view of FIGS. 15A and 15C respectively.

It is noted that the scope of the present invention includes the use of only one wavenumber biomarker for differential diagnosis of benign and malignant solid tumors, as well as the use of two, three, four, or more wavenumbers.

Embodiments of the present invention described herein can take the form of an entirely hardware embodiment, an entirely software embodiment or an embodiment including both hardware and software elements. In an embodiment, the invention is implemented in software, which includes but is not limited to firmware, resident software, microcode, etc.

Furthermore, the embodiments of the invention can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Reference is made to FIG. 16. Typically, the operations described herein are performed by a system 30 which transforms the physical state of a memory 26, which is a real physical article, to have a different magnetic polarity, electrical charge, or the like depending on the technology of the memory that is used. A processor 22 of system 30 performs the analysis described herein, based on inputs from an FTIR system 20, and outputs the results of the analysis to an output device 24 (e.g., a screen, a printer, or a long-term storage medium). System 30 may thus be used to perform analysis that includes any of the wavenumbers described herein.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that the operations described herein can be implemented by computer program instructions. These computer program instructions may be provided to a processor (e.g., processor 22) of a general purpose computer, special purpose computer, or other programmable data processing apparatus to produce a machine, such that the instructions, which execute via the processor of the computer or other programmable data processing apparatus, create means for implementing the functions/acts described herein. These computer program instructions may also be stored in a computer-readable medium that can direct a computer or other programmable data processing apparatus to function in a particular manner, such that the instructions stored in the computer-readable medium produce an article of manufacture including instruction means which implement the functions/acts described herein. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
    identifying a subject as possibly having a benign tumor in breast tissue of the subject;
    obtaining an infrared (IR) spectrum of a Peripheral Blood Mononuclear Cells (PBMC) sample of the subject by analyzing the sample by infrared spectroscopy;
    assessing a characteristic of the sample at at least one wavenumber selected from the group consisting of: 837.4±4 cm-1, 1027.9±4 cm-1, 1182.6±4 cm-1, 1213.0±4 cm-1, 1278.1±4 cm-1, 1544.2±4 cm-1, 1011.0±4 cm-1, 1071.7 cm-1, 1141.7±4 cm-1, 1158.0±4 cm-1, 1181.7±4 cm-1, and 1502.3±4 cm-1; and
    using a processor comparing, at the at least one wavenumber, the infrared spectrum to an infrared spectrum obtained from a PBMC sample from a person without a benign tumor, to detect a difference between the infrared spectrum of the PBMC sample of the subject and the infrared spectrum obtained from the PBMC sample from the person without a benign tumor.

2. The method according to claim 1, further comprising:
    obtaining an infrared (IR) spectrum of a plasma sample of the subject by analyzing the plasma sample by infrared spectroscopy;
    assessing a characteristic of the plasma sample at at least one plasma wavenumber selected from the group consisting of: 1402.5±4 cm-1, 1466.6±4 cm-1, 1587.1±4 cm-1, 1169.6±4 cm-1, 1674.9±4 cm-1, 1512.4±4 cm-1, and 1267.0±4 cm-1; and
    comparing, at the at least one plasma wavenumber, the infrared spectrum of the plasma sample to an infrared spectrum obtained from a plasma sample from a person without a benign tumor, to detect a difference between the infrared spectrum of the plasma sample of the subject and the infrared spectrum obtained from the plasma sample from the person without a benign tumor.

3. The method according to claim 1, wherein analyzing comprises assessing the characteristic at at least two wavenumbers selected from the group.

4. The method according to claim 1, wherein analyzing comprises assessing the characteristic at at least three wavenumbers selected from the group.

5. The method according to claim 1, wherein assessing the characteristic of the sample at at least one wavenumber comprises assessing the characteristic of the sample at at least one wavenumber selected from the group consisting of: 837.4±4 cm-1, 1027.9±4 cm-1, 1182.6±4 cm-1, 1213.0±4 cm-1, 1278.1±4 cm-1, and 1544.2±4 cm-1, and wherein the person without a benign tumor is a person without a tumor.

6. The method according to claim 1, wherein assessing the characteristic of the sample at at least one wavenumber comprises assessing the characteristic of the sample at at least one wavenumber selected from the group consisting of: 1011.0±4 cm-1, 1071.7 cm-1, 1141.7±4 cm-1, 1158.0±4 cm-1, 1181.7±4 cm-1, and 1502.3±4 cm-1, and wherein the person without a benign tumor is a person with a malignant tumor.

7. The method according to claim 1, wherein analyzing the sample comprises obtaining a second derivative of the infrared (IR) spectrum of the sample.

8. A method comprising:
obtaining an infrared (IR) spectrum of a plasma blood sample of a subject by analyzing the sample by infrared spectroscopy;
assessing a characteristic of the sample at at least one wavenumber selected from the group consisting of: 1402.5±4 cm-1, 1466.6±4 cm-1, 1587.1±4 cm-1, 1169.6±4 cm-1, 1674.9±4 cm-1, 1512.4±4 cm-1, 1267.0±4 cm-1, 1378.9±4 cm-1, 1404.9±4 cm-1, 774.3±4 cm-1, 1153.2±4 cm-1, and 992.7±4 cm-1; and
using a processor comparing, at the at least one wavenumber, the infrared spectrum to an infrared spectrum obtained from a plasma sample from a person without a benign tumor, to detect a difference between the infrared spectrum of the plasma sample of the subject and the infrared spectrum obtained from the plasma sample from the person without a benign tumor.

9. The method according to claim 8, further comprising:
identifying the subject as possibly having a benign tumor in breast tissue of the subject,
wherein assessing the characteristic of the sample at at least one wavenumber comprises assessing the characteristic of the sample at at least one wavenumber selected from the group consisting of: 1402.5±4 cm-1, 1466.6±4 cm-1, 1587.1±4 cm-1, 1169.6±4 cm-1, 1674.9±4 cm-1, 1512.4±4 cm-1, and 1267.0±4 cm-1.

10. The method according to claim 8, further comprising:
identifying the subject as possibly having a benign tumor in gastrointestinal tract tissue of the subject,
wherein assessing the characteristic of the sample at at least one wavenumber comprises assessing the characteristic of the sample at at least one wavenumber selected from the group consisting of: 1378.9±4 cm-1, 1404.9±4 cm-1, 774.3±4 cm-1, 1153.2±4 cm-1, and 992.7±4 cm-1.

11. A method comprising:
identifying a subject as possibly having a benign tumor in gastrointestinal tract tissue of the subject;
obtaining an infrared (IR) spectrum of a Peripheral Blood Mononuclear Cells (PBMC) sample of the subject by analyzing the sample by infrared spectroscopy;
assessing a characteristic of the sample at at least one wavenumber selected from the group consisting of: 785.4±4 cm-1, 811.9±4 cm-1, 879.9±4 cm-1, 1253.0±4 cm-1, 1485.4±4 cm-1, 1526.9±4 cm-1, 760.8±4 cm-1, 870.7±4 cm-1, and 1485.9±4 cm-1; and
using a processor comparing, at the at least one wavenumber, the infrared spectrum to an infrared spectrum obtained from a PBMC sample from a person without a benign tumor, to detect a difference between the infrared spectrum of the PBMC sample of the subject and the infrared spectrum obtained from the PBMC sample from the person without a benign tumor.

12. The method according to claim 11, further comprising:
obtaining an infrared (IR) spectrum of a plasma sample of the subject by analyzing the plasma sample by infrared spectroscopy;
assessing a characteristic of the plasma sample at at least one plasma wavenumber selected from the group consisting of: 1378.9±4 cm-1, 1404.9±4 cm-1, 774.3±4 cm-1, 1153.2±4 cm-1, and 992.7±4 cm-1; and
comparing, at the at least one plasma wavenumber, the infrared spectrum of the plasma sample to an infrared spectrum obtained from a plasma sample from a person without a benign tumor, to detect a difference between the infrared spectrum of the plasma sample of the subject and the infrared spectrum obtained from the plasma sample from the person without a benign tumor.

13. The method according to claim 11, wherein analyzing comprises assessing the characteristic at at least two wavenumbers selected from the group.

14. The method according to claim 11, wherein analyzing comprises assessing the characteristic at at least three wavenumbers selected from the group.

15. The method according to claim 11, wherein assessing the characteristic of the sample at at least one wavenumber comprises assessing the characteristic of the sample at at least one wavenumber selected from the group consisting of: 785.4±4 cm-1, 811.9±4 cm-1, 879.9±4 cm-1, 1253.0±4 cm-1, 1485.4±4 cm-1, and 1526.9±4 cm-1, and the person without a benign tumor is a person without a tumor.

16. The method according to claim 11, wherein assessing the characteristic of the sample at at least one wavenumber comprises assessing the characteristic of the sample at at least one wavenumber selected from the group consisting of: 760.8±4 cm-1, 870.7±4 cm-1, 1485.9±4 cm-1, and 1526.9±4 cm-1, and wherein the person without a benign tumor is a person with a malignant tumor.

* * * * *